US010947281B2

(12) United States Patent
Pan

(10) Patent No.: US 10,947,281 B2
(45) Date of Patent: Mar. 16, 2021

(54) IDENTIFICATION OF CHANNELRHODOPSIN-2 (CHR2) MUTATIONS AND METHODS OF USE

(71) Applicant: Wayne State University, Detroit, MI (US)

(72) Inventor: Zhuo-hua Pan, Troy, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 14/383,211

(22) PCT Filed: Mar. 5, 2013

(86) PCT No.: PCT/US2013/029171
§ 371 (c)(1),
(2) Date: Sep. 5, 2014

(87) PCT Pub. No.: WO2013/134295
PCT Pub. Date: Sep. 12, 2013

(65) Prior Publication Data
US 2015/0044181 A1    Feb. 12, 2015

Related U.S. Application Data

(60) Provisional application No. 61/606,663, filed on Mar. 5, 2012.

(51) Int. Cl.
| | | |
|---|---|---|
| *A61K 38/16* | (2006.01) | |
| *A61K 38/00* | (2006.01) | |
| *A61P 9/10* | (2006.01) | |
| *A61P 27/02* | (2006.01) | |
| *C07K 1/00* | (2006.01) | |
| *C07K 14/00* | (2006.01) | |
| *C07K 17/00* | (2006.01) | |
| *C07K 14/405* | (2006.01) | |
| *A61K 48/00* | (2006.01) | |

(52) U.S. Cl.
CPC ............ *C07K 14/405* (2013.01); *A61K 38/16* (2013.01); *A61P 27/02* (2018.01); *C07K 14/00* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 4,498,919 A | 2/1985 | Mann | |
| 4,554,101 A | 11/1985 | Hopp | |
| 5,827,702 A | 10/1998 | Cuthbertson | |
| 6,610,287 B1 | 8/2003 | Breakefield et al. | |
| 7,144,733 B2 | 12/2006 | Miesenbook et al. | |
| 7,186,699 B2 | 3/2007 | Harding et al. | |
| 7,427,138 B2 | 9/2008 | Ellenbogen | |
| 7,824,869 B2 | 11/2010 | Hegemann et al. | |
| 8,470,790 B2 | 6/2013 | Pan et al. | |
| 2004/0022766 A1 | 2/2004 | Acland et al. | |
| 2005/0202398 A1 | 9/2005 | Hegemann et al. | |
| 2005/0208022 A1 | 9/2005 | Masland | |
| 2010/0015095 A1 | 1/2010 | Pan et al. | |
| 2013/0259833 A1 | 10/2013 | Pan | |
| 2014/0121265 A1 | 5/2014 | Pan et al. | |

FOREIGN PATENT DOCUMENTS

| | | |
|---|---|---|
| WO | WO 1998/048027 | 10/1998 |
| WO | WO 0015822 | 3/2000 |
| WO | WO0183692 | 11/2001 |
| WO | WO 2005/044096 | 5/2005 |
| WO | WO 07024391 A2 | 3/2007 |
| WO | WO 2007/131180 | 11/2007 |
| WO | WO 2011/140279 | 11/2011 |
| WO | WO 2012/032103 | 3/2012 |
| WO | WO 2013/134295 | 9/2013 |

OTHER PUBLICATIONS

NCBI Blast Protein Comparison between WO2012/032103 SEQ ID No. 1 and claimed SEQ ID No. 26, 2 pages (conducted on May 12, 2016).*
Vimont, C., https://www.aao.org/eye-health/tips-prevention/what-does-20-20-vision-mean, 5 pages (2020) (Year: 2020).*
International Search Report for International Patent Application No. PCT/US2013/029171, dated Aug. 27, 2013.
Berndt, A. et al., "High-efficiency channelrhodopsins for fast neuronal stimulation at low light levels", Proceedings of the National Academy of Sciences, vol. 108, No. 18, May 3, 2011, pp. 7595-7600.
Ivanova, E., et al., "Evaluation of AAV-Mediated Expression of Chop2-GFP in the Marmoset Retina", Investigative Opthamology & Visual Science, vol. 51, No. 10, Oct. 1, 2010, pp. 5288-5296.
Kleinlogel, S., et al., "Ultra light-sensitive and fast neuronal activation with the Ca2+-permeable channelrhodopsin CatCh", Nature Neuroscience, vol. 14, No. 4, Mar. 13, 2011, pp. 513-518.
Prigge et al., "Color-tuned Channelrhodopsins for Multiwavelength Optogenetics", Journal of Biological Chemistry, vol. 287, No. 38, Jul. 27, 2012, pp. 31804-31812.

(Continued)

*Primary Examiner* — James H Alstrum-Acevedo
*Assistant Examiner* — Thea D'Ambrosio
(74) *Attorney, Agent, or Firm* — Mintz, Levin, Cohn, Ferris, Glovsky and Popeo, P.C.

(57) ABSTRACT

The invention provides compositions and kits including at least one nucleic acid or polypeptide molecule encoding for a mutant ChR2 protein. Methods of the invention include administering a composition comprising a mutant ChR2 to a subject to preserve, improve, or restore phototransduction. Preferably, the compositions and methods of the invention are provided to a subject having impaired vision, thereby restoring vision to normal levels.

7 Claims, 5 Drawing Sheets

Specification includes a Sequence Listing.

(56) References Cited

OTHER PUBLICATIONS

Rein, M.L., et al., "The optogenetic (r)evolution", Molecular Genetics and Genomics, vol. 287, No. 2, Dec. 20, 2011, pp. 95-109, Springer, Berlin, Germany.
Ullrich, S., et al., "Degradation of channelopsin-2 in the absence of retinal and degradation resistance in certain mutants", Biological Chemistry, vol. 394, No. 2, Feb. 1, 2013, pp. 271-280, Walter de Gruvter GmbH & Co., Berlin, Germany.
Zhang, F., et al., "The Microbial Opsin Family of Optogenetic Tools", Cell, vol. 147, No. 7. Nov. 23, 2011, pp. 1446-1457.
Acland, G.M. et al., "Gene Therapyy Restores Vision in a Canine Model of Childhood Blindness," Nat. Genet., vol. 28, pp. 92-95 (2001). Abstract.
Ali, R.R. et al., "Restoration of Photoreceptor Ultrastructure and Function in Retinal Degeneration Slow Mice by Gene Therapy," Nat. Genet., vol. 25, pp. 306-310 (2000). Abstract.
Banghart, M. et al., "Light-activated ion channels for remote control of neuronal firing," Nat. Neurosci., vol. 7, pp. 1381-1386 (2004).
Baylor, D., "How Photons Start Vision," Proc. Natl. Acad. Sci. USA, vol. 93, pp. 560-565 (1996).
Bennett, J et al., "Stable transgene expression in rod photoreceptors afterrecombinant adeno-associated virus-mediated gene transfer to monkey retina," Proc. Natl. Acad. Sci. USA, vol. 96, pp. 9920-9925 (1999).
Bennett, J. et al., Adenovirus-mediated delivery of rhodopsin-promoted bcl-2 results in a delay in photoreceptor cell death in the rd/rd mouse, Gene Therapy vol. 5, pp. 1156-1164 (1998).
Bennett, J. et al., "Photoreceptor cell rescue in retinal degeneration (rd) mice by in vivo gene therapy," Nat. Med., vol. 2, pp. 649-654 (1996). Abstract.
Berson, D. M. "Phototransduction in Ganglion-Cell Photoreceptors." Eur. J. Physiol. 454:849-855 (2007).
Bi, A. et al., "Ectopic expression of a microbial-type rhodopsin restores visual responses in mice with photoreceptor degeneration," Neuron, vol. 50, pp. 23-33 (2006). Abstract.
Borras, T. "Recent Developments in Ocular Gene Therapy." Exp. Eye Res., vol. 76, pp. 643-652 (2003). Abstract.
Casini et al., "Developmental Expression of Neurokinin-1 and Neurokinin-3 Receptors in the Rat Retina." J. Comp. Neurol., vol. 421, pp. 275-287 (2001). Abstract.
Chang, B. et al., "Retinal degeneration mutants in the mouse," Vision Res., vol. 42, 2002, pp. 517-525.
Communication Pursuant to Article 94(3) EPC issued by the European Patent Office for Application No. EP07797340.2, dated Sep. 25, 2014, 5 pages.
Flannery, J.G. et al., "Looking Within for Vision." Neuron, vol. 50(1):1-3 (2006). Abstract.
Flannery, J.G.et al., "Efficient photoreceptor-targeted gene expression in vivo by recombinant adeno-associated virus," Proc. Natl. Acad. Sci. USA, vol. 94, 1997, pp. 6916-6921.
Greenberg, K.P. et al., "In vivo Transgene Expression in ON-Type Retinal Ganglion Cells: Applications to Retinal Disease," Arvo Abstract (2007).
Hankins, M. W. et al., "Melanopsin: An Exciting Photopigment." Trends Neurosci., vol. 31(1):27-36 (2007). Abstract.
Hauswirth, W. W. et al., "Ocular Gene Therapy: Quo Vadis?" Invest. Ophthal. Vis. Sci., vol. 41 (10): 2821-2826 (2000).
Hauswirth, W.W., "The Consortium Project to Treat RPE65 Deficiency in Humans," Retina, vol. 25, p. 60 (2005).
Haverkamp, S. et al., "Immunocytochemical Description of Five Bipolar Cell Types of the Mouse Retina," J Comp. Neurol., vol. 455(4):463-76 (2003).
Hossain, P. et al., "Artificial Means for Restoring Vision." Brit. Med. J., vol. 330:30-33 (2005).
Humphries, P et al., "On the molecular genetics of retinitis pigmentosa," Science, vol. 256, 1992, pp. 804-808. Abstract.
International Preliminary Report on Patentability and Written Opinion of the International Searching Authority for PCT/US2007/068263, dated May 15, 2008, 6 pages.
International Search Report issued by the International Searching Authority for PCT/US2007/068263, dated May 15, 2008, 4 pages.
International Preliminary Report on Patentability and Written Opinion of the International Searching Authority for PCT/US2011/035266, dated Nov. 6, 2012, 5 pages.
International Search Report of the International Searching Authority for PCT/US2011/035266, dated Jul. 27, 2011, 4 pages.
International Preliminary Report on Patentability and Written Opinion of the International Searching Authority for PCT/US2013/029171, dated Sep. 9, 2014, 12 pages.
Ishizuka et al., "Kinetic Evaluation of Photosensitivity in Genetically Engineered Neurons Expressing Green Algae Light-Gated Channels," Neurosci. Res., vol. 54:85-94, online Nov. 17, 2005.
Jacobson, S.G., "Discussion of Human Gene Transfer Protocol #0410-677: Phase I Trial of Ocular Subretinal Injection of a Recombinant Adeno-Associated Virus (rAAV-RPE65) Gene Vector in Patients with Retinal Disease due to RPE65 Mutations," National Institutes of Health Recombinant DNA Advisory Committee (RAC) Meeting Jun. 15-16, 2005, 47 pages.
Kay, M.A. et al., Viral Vectors for Gene Therapy: The Art of Turning Infectious Agents into Vehicles of Therapeutics, Nat. Med., vol. 7, pp. 33-40 (2001). Abstract.
Kumar-Singh, R. et al., "Encapsidated adenovirus mini-chromosome-mediated delivery of genes to the retina: application to the rescue of photoreceptor degeneration," Hum. Mol. Genet., vol. 7, pp. 1893-1900 (1998).
Lanyi, J.K., "Bacteriorhodopsin." Ann. Rev. Physiol., vol. 66, 2004, pp. 665-688. Abstract.
Lanyi, J.K., "Halorhodopsin, a Light-Driven Electrogenic Chloride-Transport System," Physiol. Rev., vol. 70(2):319-30 (1990).
Lau, D. et al., "Retinal Degeneration Is Slowed in Transgenic Rats by AAV-Mediated Delivery of FGF-2," Invest. Ophthalmol. Vis. Sci., vol. 41, pp. 3622-3633 92000).
Lavail, M.M. et al., "Ribozyme rescue of photoreceptor cells in P23H transgenic rats: Long-term survival and late-stage therapy," Proc. Natl. Acad. Sci. USA, vol. 97, pp. 11488-11493 (2000).
Lavail, MM et al., "Multiple growth factors, cytokines, and neurotrophins rescue photoreceptors from the damaging effects of constant light," Proc. Natl. Acad. Sci. USA, vol. 89, pp. 11249-11253 (1992).
Lewin, AS et al., "Ribozyme Rescue of Photoreceptor Cells in a Transgenic Rat Model of Autosomal Dominant Retinitis Pigmentosa," Nat. Med., vol. 4, pp. 967-971 (1998).
Lin et al.,"Restoration of Visual Function in Retinal Degeneration Mice by Ectopic Expression of Melanopsin," Proc. Natl. Acad. Sci. USA, vol. 105:16009-14 (2008).
McFarland et al., "Gene Therapy for Proliferative Ocular Diseases." Exp. Opin. Bioi. Ther., vol. 4(7):1053-1058 (2004).
Medeiros et al., "Preservation of Ganglion Cell Layer Neurons in Age-Related Macular Degeneration." Invest. Ophthal. Vis. Sci., vol. 42(3):795-803 (2001).
Melyan, Z. et al., "Addition of human melanopsin renders mammalian cells photoresponsive," Nature, vol. 433, pp. 741-745 (2005).
Milam, AH et al., "Histopathology of the Human Retina in Retinitis Pigmentosa," Prog. Retin. Eye Res., vol. 17, pp. 175-205 (1998).
Nagel et al., "Channelrhodopsin-2, a Directly Light-Gated Cation-Selective Membrane Channel." Proc. Natl. Acad. Sci. USA, vol. 100(24):13940-13945 (2003). Abstract.
Nagel, G. et al., "Channelrhodopsin-1: A Light-Gated Proton Channel in Green Algae," Science vol. 296, pp. 2395-2398 (2002).
Nakajima, Y. et al., "Molecular Characterization of a Novel Retinal Metabotropic Glutamate Receptor mGluR6 with a High Agonist Selectivity for L-2-Amino-4-phosphonobutyrate," J. Biol. Chem., vol. 268, pp. 11868-11873 (1993).
Oesterhelt, D et al., "Functions of a New Photoreceptor Membrane," Proc. Natl. Acad. Sci. USA, vol. 70, pp. 2853-2857 (1973).
Oesterhelt, D., "The structure and mechanism of the family of retinal proteins from halophilic archaea," Curr. Opin. Struct. Biol., vol. 8, 1998, pp. 489-500.
Office Action issued by the United States Patent and Trademark Office for U.S. Appl. No. 12/299,574, dated Aug. 28, 2012, 15 pages.
Office Action issued by the United States Patent and Trademark Office for U.S. Appl. No. 12/299,574, dated Jan. 12, 2012, 10 pages.

(56) References Cited

OTHER PUBLICATIONS

Office Action issued by the United States Patent and Trademark Office for U.S. Appl. No. 13/899,198, dated Jul. 21, 2014, 20 pages.
Office Action issued by the United States Patent and Trademark Office for U.S. Appl. No. 13/696,252, dated Sep. 22, 2014, 13 pages.
Olshevskaya, EV et al., "The Y99C Mutation in Guanylyl Cyclase-Activating Protein 1 Increases Intracellular $Ca^{2+}$ and Causes Photoreceptor Degeneration in Transgenic Mice," J. Neurosci., vol. 24, pp. 6078-6085 (2004).
Pan et al., "Functional expression of a directly light-gated membrane channel in mammalian retinal neurons: A potential strategy for restoring light sensitivity to the retina after photoreceptor degeneration," Ophthalmol. & Vis. Sci., vol. 46:E-Abstract 4631 (2005). Abstract.
Panda, S. et al., "Illumination of the Melanopsin Signaling Pathway," Science, vol. 307, pp. 600-604 (2005).
Qiu, X. et al.,"Induction of photosensitivity by heterologous expression of melanopsin," Nature, vol. 433, pp. 745-749 (2005).
Reutsky et al., "Patterned Optical Activation of Channelrhodopsin II Expressing Retinal Ganglion Cells." Proc. 3rd Int. IEEE EMBS Conference on Neural Engineering, pp. 50-52 (2007).
Santos, AH et al., "Preservation of the Inner Retina in Retinitis Pigmentosa," Arch. Ophthalmol., vol. 115, pp. 511-515 (1997).
Sineshchekov, OA et al., "Two rhodopsins mediate phototaxis to low- and high-intensity light in Chlamydomonas reinhardtii," Proc. Natl. Acad. Sci. USA, vol. 99, pp. 8689-8694 (2002).
Sung, Ch et al., "Rhodopsin mutations in autosomal dominant retinitis pigmentosa," Proc. Natl. Acad. Sci. USA, vol. 88, pp. 6481-6485 (1991).
Supplementary European Search Repor issued by the European Patent Office for Application No. EP07797340.2, dated Oct. 27, 2010, 7 pages.
Takahashi, M. et al., "Rescue from Photoreceptor Degeneration in the rd Mouse by Human Immunodeficiency Virus Vector-Mediated Gene Transfer," J. Virol., vol. 73, pp. 7812-7816 (1999).
Tomita, H. et al., "Channelrhodopsins provide a breakthrough insight into strategies for curing blindness," Journal of Genetics, vol. 88:409-415 (2009).
Thyagarajan et al., "Visual Function in Mice with Photoreceptor Degeneration and Transgenic Expression of Channelrhodopsin 2 in Ganglion Cells," J. Neurosci., vol. 30:8745-5 (2010).
Tomomura, M et al.,"Puri® cation of Purkinje cells by fluorescence-activated cell sorting from transgenic mice that express green fluorescent protein," Eur. J. Neurosci., vol. 14, pp. 57-63 (2001).
Ueda et al., "The mGluR6 5' upstream transgene sequence directs a cell-specific and developmentally regulated expression in retinal rod and ON-type cone bipolar cells," J. Neurosci ., vol. 17(9):3014-23 (1997).
Veraart et al., "Vision Rehabilitation in the case of Blindness," Expert Rev. Medical Devices, vol. 1(1):139-153 (2004). Abstract.
Walther et al., "Viral Vectors for Gene Transfer a Review of Their Use in the Treatment of Human Diseases," Drugs, vol. 60, pp. 249-271 (2000).
Wässle, H., "Parallel Processing in the Mammalian Retina," Nat. Rev. Neurosci., vol. 5, pp. 747-757 (2004).
Han, X. et al., "Multiple-color optical activation, silencing, and desynchronization of neural activity, with single-spike temporal resolution," PLOS ONE 2007 LNKD-PUBMED:17375185, vol. 2(3): e299 (2007).
Zemelman, B.V. et al., "Selective Photostimulation of Genetically ChARGed Neurons," Neuron, vol. 33, pp. 15-22 (2002).
Zhang, F. et al., "Multimodal fast optical interrogation of neural circuitry," Nature, vol. 446, pp. 633-639 (2007).
Zrenner, E., "Will Retinal Implants Restore Vision?" Science, vol. 295:1022-5 (2002).
Zhuo-Hua Pan et al: "ChR2 Mutants at L 132 and T159 with Improved Operational Light Sensitivity for Vision Restoration", PLoS ONE, vol. 9, No. 6, Jun. 5, 2014, p. e98924 (12 pages).

\* cited by examiner

```
                        SEQUENCE LISTING

<160> NUMBER OF SEQ ID NOS: 26

<210> SEQ ID NO 1
<211> LENGTH: 3585
<212> TYPE: DNA
<213> ORGANISM: Chlamydomonas reinhardtii

<400> SEQUENCE: 1
gcagcaccat acttgacatc tgtcgccaag caagcattaa acatggatta tggaggcgcc      60
ctgagtgccg ttgggcgcga gctgctattt gtaacgaacc cagtagtcgt caatggctct     120
gtacttgtgc ctgaggacca gtgttactgc gcgggctgga ttgagtcgcg tggcacaaac     180
ggtgcccaaa cggcgtcgaa cgtgctgcaa tggcttgctg ctggcttctc catcctactg     240
cttatgtttt acgcctacca aacatggaag tcaacctgcg gctgggagga gatctatgtg     300
tgcgctatcg agatggtcaa ggtgattctc gagttcttct tcgagtttaa gaacccgtcc     360
atgctgtatc tagccacagg ccaccgcgtc cagtggttgc gttacgccga gtggcttctc     420
acctgcccgg tcattctcat tcacctgtca aacctgacgg gcttgtccaa cgactacagc     480
aggcgcacca tgggtctgct tgtgtctgat attggcacaa ttgtgtgggg cgccacttcc     540
gccatggcca ccggatacgt caaggtcatc ttcttctgcc tgggtctgtg ttatggtgct     600
aacacgttct ttcacgctgc caaggcctac atcgagggtt accacaccgt gccgaagggc     660
cggtgtcgcc aggtggtgac tggcatggct tggctcttct tcgtatcatg gggtatgttc     720
cccatcctgt tcatcctcgg ccccgagggc ttcggcgtcc tgagcgtgta cggctccacc     780
gtcggccaca ccatcattga cctgatgtcg aagaactgct ggggtctgct cggccactac     840
ctgcgcgtgc tgatccacga gcatatcctc atccacgccg acattcgcaa gaccaccaaa     900
ttgaacattg gtgcactga gattgaggtc gagacgctgg tggaggacga ggccgaggct     960
ggcgcggtca acaagggcac cggcaagtac gcctcccgcg agtccttcct ggtcatgcgc    1020
gacaagatga aggagaaggg cattgacgtg cgcgcctctc tggacaacag caaggaggtg    1080
```

```
gagcaggagc aggccgccag ggctgccatg atgatgatga acggcaatgg catgggtatg   1140
ggaatgggaa tgaacggcat gaacggaatg ggcggtatga acgggatggc tggcggcgcc   1200
aagcccggcc tggagctcac tccgcagcta cagcccggcc gcgtcatcct ggcggtgccg   1260
gacatcagca tggttgactt cttccgcgag cagtttgctc agctatcggt gacgtacgag   1320
ctggtgccgg ccctgggcgc tgacaacaca ctggcgctgg ttacgcaggc gcagaacctg   1380
ggcggcgtgg actttgtgtt gattcacccc gagttcctgc gcgaccgctc tagcaccagc   1440
atcctgagcc gcctgcgcgg cgcgggccag cgtgtggctg cgttcggctg ggcgcagctg   1500
gggcccatgc gtgacctgat cgagtccgca aacctggacg gctggctgga gggcccctcg   1560
ttcggacagg gcatcctgcc ggcccacatc gttgccctgg tggccaagat gcagcagatg   1620
cgcaagatgc agcagatgca gcagattggc atgatgaccg gcggcatgaa cggcatgggc   1680
ggcggtatgg gcggcggcat gaacggcatg ggcggcggca acggcatgaa caacatgggc   1740
aacggcatgg gcggcggcat gggcaacggc atgggcggca atggcatgaa cggaatgggt   1800
ggcggcaacg gcatgaacaa catgggcggc aacggaatgg ccggcaacgg aatgggcggc   1860
ggcatgggcg gcaacggtat gggtggctcc atgaacggca tgagctccgg cgtggtggcc   1920
aacgtgacgc cctccgccgc cggcggcatg ggcggcatga tgaacggcgg catggctgcg   1980
ccccagtcgc ccggcatgaa cggcggccgc ctgggtacca acccgctctt caacgccgcg   2040
ccctcaccgc tcagctcgca gctcggtgcc gaggcaggca tgggcagcat gggaggcatg   2100
ggcggaatga gcggaatggg aggcatgggt ggaatgggggg gcatgggcgg cgccggcgcc   2160
gccacgacgc aggctgcggg cggcaacgcg gaggcggaga tgctgcagaa tctcatgaac   2220
gagatcaatc gcctgaagcg cgagcttggc gagtaaaagg ctggaggccg gtactgcgat   2280
acctgcgagc tcgcgcgcct gactcgtcgt acacacggct caggagcacg cgcgcgtgga   2340
cttctcaacc tgtgtgcaac gtatctagag cggcctgtgc gcgaccgtcc gtgagcattc   2400
cggtgcgatc ttcccgcctt cgcaccgcaa gttcccttcc tggccctgct gcgcctgacg   2460
catcgtccga acgaagggc ggcttgatca gtaaagcatt gaagactgaa gtcgtgcgac   2520
cgtagtgcta tggctctgca cgtaagtggg cgctgccctg cttactacgc attgcccaag   2580
actgcttcct tttggtggcc gaggccctgg tcccacatca ttcatttgca taacgtactg   2640
tttagttaca tacgctttgc ttaacctcga caattgcaac atgggctgag agtccgtacg   2700
gcggctatgg acgaaggtgt tatcggatgt gattaggaat ctcggttgaa aggcttcgag   2760
aaagtgagct tcatctgtgg cttctgttgg ggtcatcaag aagaacgacg gtaaggcaaa   2820
cgaggtaaaa gtggcacgtc tttgtgcaca acgggcccgt ggagagtggg ggagtgcatg   2880
tgtgcggtcc taacacgcga gtgcaaagcg ggcttttctg gagctgggtt acggtctggc   2940
tcggcaactg ctctgtgttt taaccacagc ttcggaagtc tgggtatgtt ttgttggcag   3000
aaacatttgg gtaacttgag ggtgattcgt ctggagtcgg acaacatggc tgccgtccgt   3060
gtgcagggac ggtaatcaat gagctggagc tgtgatgctc accacacgtt gcataccct   3120 gcttacaaaa acactttgat gtcgtggcca aactatgcgt gagcaaagag ttaaagaggc   3180
atgagtgcat ggttgcggac gtgcgcaaca attgcatcaa gtatttgacg ccttcaagcc   3240
aacaagtgcg cgcgcggcaa cttgattaac acgccggacg cagtggtggg ggcgtgtaca   3300
gtgtttatga gctgccattc tgcgatccgt agtgttaggt tgcgtgtgac gccgcgcggc   3360
tgtgggccct tacatggaga gttgggtgct tcaccacacg gttggcgccg ctgaagggtg   3420
```

-continued

```
tgctatgttt tggtaaagcc ggggccctga agaccgcaac cgtagaaccg tactgaaagg    3480
gtgtcagccc ggggtaactg gatgccctgg gacatagcta ttaatgttga agtgaagccg    3540
tcaagccgag tgccgtgcgc cgctgtatca ccaaggcccg tccta                   3585
```

<210> SEQ ID NO 2
<211> LENGTH: 737
<212> TYPE: PRT
<213> ORGANISM: Chlamydomonas reinhardtii

<400> SEQUENCE: 2

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335

Arg Ala Ser Leu Asp Asn Ser Lys Glu Val Glu Gln Glu Gln Ala Ala
            340                 345                 350
```

```
Arg Ala Ala Met Met Met Met Asn Gly Asn Gly Met Gly Met Gly Met
        355                 360                 365

Gly Met Asn Gly Met Asn Gly Met Gly Gly Met Asn Gly Met Ala Gly
    370                 375                 380

Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                405                 410                 415

Gln Phe Ala Gln Leu Ser Val Thr Tyr Glu Leu Val Pro Ala Leu Gly
            420                 425                 430

Ala Asp Asn Thr Leu Ala Leu Val Thr Gln Ala Gln Asn Leu Gly Gly
        435                 440                 445

Val Asp Phe Val Leu Ile His Pro Glu Phe Leu Arg Asp Arg Ser Ser
    450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
                485                 490                 495

Asn Leu Asp Gly Trp Leu Glu Gly Pro Ser Phe Gly Gln Gly Ile Leu
            500                 505                 510

Pro Ala His Ile Val Ala Leu Val Ala Lys Met Gln Gln Met Arg Lys
        515                 520                 525

Met Gln Gln Met Gln Gln Ile Gly Met Met Thr Gly Gly Met Asn Gly
    530                 535                 540

Met Gly Gly Gly Met Gly Gly Gly Met Asn Gly Met Gly Gly Gly Asn
545                 550                 555                 560

Gly Met Asn Asn Met Gly Asn Gly Met Gly Gly Gly Met Gly Asn Gly
                565                 570                 575

Met Gly Gly Asn Gly Met Asn Gly Met Gly Gly Asn Gly Met Asn
            580                 585                 590

Asn Met Gly Gly Asn Gly Met Ala Gly Asn Gly Met Gly Gly Gly Met
        595                 600                 605

Gly Gly Asn Gly Met Gly Gly Ser Met Asn Gly Met Ser Ser Gly Val
    610                 615                 620

Val Ala Asn Val Thr Pro Ser Ala Ala Gly Met Gly Gly Met Met
625                 630                 635                 640

Asn Gly Gly Met Ala Ala Pro Gln Ser Pro Gly Met Asn Gly Gly Arg
                645                 650                 655

Leu Gly Thr Asn Pro Leu Phe Asn Ala Ala Pro Ser Pro Leu Ser Ser
            660                 665                 670

Gln Leu Gly Ala Glu Ala Gly Met Gly Ser Met Gly Gly Met Gly Gly
        675                 680                 685

Met Ser Gly Met Gly Gly Met Gly Gly Met Gly Gly Met Gly Gly Ala
    690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 3
<211> LENGTH: 2241
<212> TYPE: DNA
```

<213> ORGANISM: Chlamydomonas reinhardtii

<400> SEQUENCE: 3

```
gcatctgtcg ccaagcaagc attaaacatg gattatggag gcgccctgag tgccgttggg      60
cgcgagctgc tatttgtaac gaacccagta gtcgtcaatg gctctgtact tgtgcctgag     120
gaccagtgtt actgcgcggg ctggattgag tcgcgtggca caaacggtgc ccaaacggcg     180
tcgaacgtgc tgcaatggct tgctgctggc ttctccatcc tactgcttat gttttacgcc     240
taccaaacat ggaagtcaac ctgcggctgg gaggagatct atgtgtgcgc tatcgagatg     300
gtcaaggtga ttctcgagtt cttcttcgag tttaagaacc cgtccatgct gtatctagcc     360
acaggccacc gcgtccagtg gttgcgttac gccgagtggc ttctcacctg cccggtcatt     420
ctcattcacc tgtcaaacct gacgggcttg tccaacgact acagcaggcg caccatgggt     480
ctgcttgtgt ctgatattgg cacaattgtg tggggcgcca cttccgccat ggccaccgga     540
tacgtcaagg tcatcttctt ctgcctgggt ctgtgttatg gtgctaacac gttctttcac     600
gctgccaagg cctacatcga gggttaccac accgtgccga agggccggtg tcgccaggtg     660
gtgactggca tggcttggct cttcttcgta tcatgggta tgttccccat cctgttcatc     720
ctcggccccg agggcttcgg cgtcctgagc gtgtacggct ccaccgtcgg ccacaccatc     780
attgacctga tgtcgaagaa ctgctggggt ctgctcggcc actacctgcg cgtgctgatc     840
cacgagcata tcctcatcca cggcgacatt cgcaagacca ccaaattgaa cattggtggc     900
actgagattg aggtcgagac gctggtggag gacgaggccg aggctggcgc ggtcaacaag     960
ggcaccggca agtacgcctc ccgcgagtcc ttcctggtca tgcgcgacaa gatgaaggag    1020
aagggcattg acgtgcgcgc ctctctggac aacagcaagg aggtggagca ggagcaggcc    1080
gccagggctg ccatgatgat gatgaacggc aatggcatgg gtatgggaat gggaatgaac    1140
ggcatgaacg gaatgggcgg tatgaacggg atggctggcg gcgccaagcc cggcctggag    1200
ctcactccgc agctacagcc cggccgcgtc atcctggcgg tgccggacat cagcatggtt    1260
gacttcttcc gcgagcagtt tgctcagcta tcggtgacgt acgagctggt gccggccctg    1320
ggcgctgaca cacactggc gctggttacg caggcgcaga acctgggcgg cgtggacttt    1380
gtgttgattc accccgagtt cctgcgcgac cgctctagca ccagcatcct gagccgcctg    1440
cgcggcgcgg ccagcgtgt ggctgcgttc ggctgggcgc agctggggcc catgcgtgac    1500
ctgatcgagt ccgcaaacct ggacggctgg ctggagggcc cctcgttcgg acagggcatc    1560
ctgccggccc acatcgttgc cctggtggcc aagatgcagc agatgcgcaa gatgcagcag    1620
atgcagcaga ttggcatgat gaccggcggc atgaacggca tgggcggcgg tatgggcggc    1680
ggcatgaacg gcatgggcgg cggcaacggc atgaacaaca tggcaacgg catgggcggc    1740
ggcatgggca acggcatggg cggcaatggc atgaacggaa tgggtggcgg caacggcatg    1800
aacaacatgg gcggcaacgg aatgccggcc aacggaatgg gcggcggcat gggcggcaac    1860
ggtatgggtg gctccatgaa cggcatgagc tccggcgtgg tggccaacgt gacgccctcc    1920
gccgccggcg gcatgggcgg catgatgaac ggcggcatgg ctgcgcccca gtcgcccggc    1980
atgaacggcg gccgcctggg taccaacccg ctccttcaacg ccgcgccctc accgctcagc    2040
tcgcagctcg gtgccgaggc aggcatgggc agcatgggag gcatgggcgg aatgagcgga    2100
atgggaggca tgggtggaat gggggggcatg ggcggcgccg cgccgccac gacgcaggct    2160
gcgggcggca acgcggaggc ggagatgctg cagaatctca tgaacgagat caatcgcctg    2220
aagcgcgagc ttggcgagta a                                              2241
```

<210> SEQ ID NO 4
<211> LENGTH: 737
<212> TYPE: PRT
<213> ORGANISM: Chlamydomonas reinhardtii

<400> SEQUENCE: 4

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335

Arg Ala Ser Leu Asp Asn Ser Lys Glu Val Glu Gln Glu Gln Ala Ala
            340                 345                 350

Arg Ala Ala Met Met Met Met Asn Gly Asn Gly Met Gly Met Gly Met
        355                 360                 365

Gly Met Asn Gly Met Asn Gly Met Gly Gly Met Asn Gly Met Ala Gly

```
                    370                 375                 380
Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                405                 410                 415

Gln Phe Ala Gln Leu Ser Val Thr Tyr Glu Leu Val Pro Ala Leu Gly
            420                 425                 430

Ala Asp Asn Thr Leu Ala Leu Val Thr Gln Ala Gln Asn Leu Gly Gly
        435                 440                 445

Val Asp Phe Val Leu Ile His Pro Glu Phe Leu Arg Asp Arg Ser Ser
    450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
                485                 490                 495

Asn Leu Asp Gly Trp Leu Glu Gly Pro Ser Phe Gly Gln Gly Ile Leu
            500                 505                 510

Pro Ala His Ile Val Ala Leu Val Ala Lys Met Gln Gln Met Arg Lys
        515                 520                 525

Met Gln Gln Met Gln Gln Ile Gly Met Met Thr Gly Gly Met Asn Gly
    530                 535                 540

Met Gly Gly Gly Met Gly Gly Met Asn Gly Met Gly Gly Asn
545                 550                 555                 560

Gly Met Asn Asn Met Gly Asn Gly Met Gly Gly Met Gly Asn Gly
                565                 570                 575

Met Gly Gly Asn Gly Met Asn Gly Met Gly Gly Asn Gly Met Asn
            580                 585                 590

Asn Met Gly Gly Asn Gly Met Ala Gly Asn Gly Met Gly Gly Met
        595                 600                 605

Gly Gly Asn Gly Met Gly Gly Ser Met Asn Gly Met Ser Ser Gly Val
    610                 615                 620

Val Ala Asn Val Thr Pro Ser Ala Ala Gly Met Gly Gly Met Met
625                 630                 635                 640

Asn Gly Gly Met Ala Ala Pro Gln Ser Pro Gly Met Asn Gly Arg
                645                 650                 655

Leu Gly Thr Asn Pro Leu Phe Asn Ala Ala Pro Ser Pro Leu Ser Ser
            660                 665                 670

Gln Leu Gly Ala Glu Ala Gly Met Gly Ser Met Gly Gly Met Gly Gly
        675                 680                 685

Met Ser Gly Met Gly Gly Met Gly Gly Met Gly Gly Met Gly Gly Ala
    690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 5
<211> LENGTH: 3599
<212> TYPE: DNA
<213> ORGANISM: Chlamydomonas reinhardtii

<400> SEQUENCE: 5
ttgacatctg tcgccaagca agcattaaac atggattatg gaggcgccct gagtgccgtt    60
```

```
gggcgcgagc tgctatttgt aacgaaccca gtagtcgtca atggctctgt acttgtgcct    120
gaggaccagt gttactgcgc gggctggatt gagtcgcgtg gcacaaacgg tgcccaaacg    180
gcgtcgaacg tgctgcaatg gcttgctgct ggcttctcca tcctactgct tatgttttac    240
gcctaccaaa catggaagtc aacctgcggc tgggaggaga tctatgtgtg cgctatcgag    300
atggtcaagg tgattctcga gttcttcttc gagtttaaga acccgtccat gctgtatcta    360
gccacaggcc accgcgtcca gtggttgcgt tacgccgagt ggcttctcac ctgcccggtc    420
attctcattc acctgtcaaa cctgacgggc ttgtccaacg actacagcag gcgcaccatg    480
ggtctgcttg tgtctgatat tggcacaatt gtgtggggcg ccacttccgc catggccacc    540
ggatacgtca aggtcatctt cttctgcctg gtctgtgtt atggtgctaa cacgttcttt    600
cacgctgcca aggcctacat cgagggttac cacaccgtgc cgaagggccg tgtcgccag    660 gtggtgactg gcatggcttg gctcttcttc gtatcatggg gtatgttccc catcctgttc    720
atcctcggcc ccgagggctt cggcgtcctg agcgtgtacg gctccaccgt cggccacacc    780
atcattgacc tgatgtcgaa gaactgctgg ggtctgctcg gccactacct gcgcgtgctg    840
atccacgagc atatcctcat ccacggcgac attcgcaaga ccaccaaatt gaacattggt    900
ggcactgaga ttgaggtcga gacgctggtg gaggacgagg ccgaggctgg cgcggtcaac    960
aagggcaccg gcaagtacgc ctcccgcgag tccttcctgg tcatgcgcga caagatgaag    1020
gagaagggca ttgacgtgcg cgcctctctg gacaacagca aggaggtgga gcaggagcag    1080
gccgccaggg ctgccatgat gatgatgaac ggcaatggca tgggtatggg aatgggaatg    1140
aacggcatga acggaatggg cggtatgaac gggatggctg gcggcgccaa gcccggcctg    1200
gagctcactc cgcagctaca gcccggccgc gtcatcctgg cggtgccgga catcagcatg    1260
gttgacttct tccgcgagca gtttgctcag ctatcggtga cgtacgagct ggtgccggcc    1320
ctgggcgctg acaacacact ggcgctggtt acgcaggcgc agaacctggg cggcgtggac    1380
tttgtgttga ttcaccccga gttcctgcgc gaccgctcta gcaccagcat cctgagccgc    1440
ctgcgcggcg cgggccagcg tgtggctgcg ttcggctggg cgcagctggg gcccatgcgt    1500
gacctgatcg agtccgcaaa cctggacggc tggctggagg gccctcgtt cggacagggc    1560 atcctgccgg cccacatcgt tgccctggtg gccaagatgc agcagatgcg caagatgcag    1620
cagatgcagc agattggcat gatgaccggc ggcatgaacg gcatgggcgg cggtatgggc    1680
ggcggcatga acggcatggg cggcggcaac ggcatgaaca acatgggcaa cggcatgggc    1740
ggcggcatgg gcaacggcat gggcggcaat ggcatgaacg gaatgggtgg cggcaacggc    1800
atgaacaaca tgggcggcaa cggaatggcc ggcaacggaa tgggcggcgg catgggcggc    1860
aacggtatgg gtggctccat gaacggcatg agctccggcg tggtggccaa cgtgacgccc    1920
tccgccgccg gcggcatggg cggcatgatg aacggcggca tggctgcgcc ccagtcgccc    1980
ggcatgaacg gcgccgcct gggtaccaac ccgctcttca cgccgcgcc ctcaccgctc    2040 agctcgcagc tcggtgccga ggcaggcatg ggcagcatgg gaggcatggg cggaatgagc    2100
ggaatgggag gcatgggtgg aatgggggc atgggcggcg ccggcgccgc cacgacgcag    2160
gctgcgggcg gcaacgcgga ggcggagatg ctgcagaatc tcatgaacga gatcaatcgc    2220
ctgaagcgcg agcttggcga gtaaaaggct ggaggccggt actgcgatac ctgcgagctc    2280
gcgcgcctga ctcgtcgtac acacggctca ggagcacgcg cgcgtggact tctcaacctg    2340
tgtgcaacgt atctagagcg gcctgtgcgc gaccgtccgt gagcattccg gtgcgatctt    2400
```

-continued

```
cccgccttcg caccgcaagt tcccttcctg gccctgctgc gcctgacgca tcgtccgaac    2460
ggaagggcgg cttgatcagt aaagcattga agactgaagt cgtgcgaccg tagtgctatg    2520
gctctgcacg taagtgggcg ctgccctgct tactacgcat tgcccaagac tgcttccttt    2580
tggtggccga ggcctggtc ccacatcatt catttgcata acgtactgtt tagttacata    2640
cgctttgctt aacctcgaca attgcaacat gggctgagag tccgtacggc ggctatggac    2700
gaaggtgtta tcggatgtga ttaggaatct cggttgaaag gcttcgagaa agtgagcttc    2760
ttctgtggct tctgttgggg tcatcaagaa gaacgacggt aaggcaaacg aggtaaaagt    2820
ggcacgtctt tgtgcacaac gggcccgtgg agagtggggg agtgcatgtg tgcggtccta    2880
acacgcgagt gcaaagcggg ctttctgga gctgggttac ggtctggctc ggcaactgct    2940
ctgtgtttta accacagctt cggaagtctg ggtatgtttt gttggcagaa catttgggt    3000
aacttgaggg tgattcgtct ggagtcggac aacatggctg ccgtccgtgt gcagggacgg    3060
taatcaatga agctgaagct gtgatgctca ccacacgttg catacccctg cttacaaaaa    3120
cactttgatg tcgtggccaa actatgcgtg agcaaagagt taaagaggca tgagtgcatg    3180
gttgcggacg tgcgcaacaa ttgcatcaag tatttgacgc cttcaagcca acaagtgcgc    3240
gcgcggcaac ttgattaaca cgccggacgc agtggtgggg gcgtgtacag tgtttatgag    3300
ctgccattct gcgatccgta gtgttaggtt gcgtgtgacg ccgcgcggct gtgggccctt    3360
acatggagag ttgggtgctt caccacacgg ttggcgccgc tgaagggtgt gctatgtttt    3420
ggtaaagccg gggccctgaa gaccgcaacc gtagaaccgt actgaaaggg tgtcagcccg    3480
gggtaactgg atgccctggg acatagctat taatgttgaa gtgaagccgt caagccgagt    3540
gccgtgcgcc gctgtatcac caaggcccgt ccaaaaaaaa aaaaaaaaa aaaaaaaaa    3599
```

<210> SEQ ID NO 6
<211> LENGTH: 737
<212> TYPE: PRT
<213> ORGANISM: Chlamydomonas reinhardtii
<400> SEQUENCE: 6

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
```

```
                    165                 170                 175
Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
            290                 295                 300

Glu Ala Gly Ala Val Asn Lys Gly Thr Gly Lys Tyr Ala Ser Arg Glu
305                 310                 315                 320

Ser Phe Leu Val Met Arg Asp Lys Met Lys Glu Lys Gly Ile Asp Val
                325                 330                 335

Arg Ala Ser Leu Asp Asn Ser Lys Glu Val Glu Gln Glu Gln Ala Ala
                340                 345                 350

Arg Ala Ala Met Met Met Met Asn Gly Asn Gly Met Gly Met Gly Met
                355                 360                 365

Gly Met Asn Gly Met Asn Gly Met Gly Gly Met Asn Gly Met Ala Gly
            370                 375                 380

Gly Ala Lys Pro Gly Leu Glu Leu Thr Pro Gln Leu Gln Pro Gly Arg
385                 390                 395                 400

Val Ile Leu Ala Val Pro Asp Ile Ser Met Val Asp Phe Phe Arg Glu
                405                 410                 415

Gln Phe Ala Gln Leu Ser Val Thr Tyr Glu Leu Val Pro Ala Leu Gly
                420                 425                 430

Ala Asp Asn Thr Leu Ala Leu Val Thr Gln Ala Gln Asn Leu Gly Gly
                435                 440                 445

Val Asp Phe Val Leu Ile His Pro Glu Phe Leu Arg Asp Arg Ser Ser
            450                 455                 460

Thr Ser Ile Leu Ser Arg Leu Arg Gly Ala Gly Gln Arg Val Ala Ala
465                 470                 475                 480

Phe Gly Trp Ala Gln Leu Gly Pro Met Arg Asp Leu Ile Glu Ser Ala
                485                 490                 495

Asn Leu Asp Gly Trp Leu Glu Gly Pro Ser Phe Gly Gln Gly Ile Leu
                500                 505                 510

Pro Ala His Ile Val Ala Leu Val Ala Lys Met Gln Gln Met Arg Lys
            515                 520                 525

Met Gln Gln Met Gln Gln Ile Gly Met Met Thr Gly Met Asn Gly
        530                 535                 540

Met Gly Gly Gly Met Gly Gly Met Asn Gly Met Gly Gly Asn
545                 550                 555                 560

Gly Met Asn Asn Met Gly Asn Gly Met Gly Gly Met Gly Asn Gly
                565                 570                 575

Met Gly Gly Asn Gly Met Asn Gly Met Gly Gly Asn Gly Met Asn
                580                 585                 590
```

```
        Asn Met Gly Gly Asn Gly Met Ala Gly Asn Gly Met Gly Gly Gly Met
            595                 600                 605

Gly Gly Asn Gly Met Gly Gly Ser Met Asn Gly Met Ser Ser Gly Val
            610                 615                 620

Val Ala Asn Val Thr Pro Ser Ala Ala Gly Met Gly Gly Met Met
        625                 630                 635                 640

Asn Gly Gly Met Ala Ala Pro Gln Ser Pro Gly Met Asn Gly Arg
                        645                 650                 655

Leu Gly Thr Asn Pro Leu Phe Asn Ala Ala Pro Ser Pro Leu Ser Ser
                        660                 665                 670

Gln Leu Gly Ala Glu Ala Gly Met Gly Ser Met Gly Gly Met Gly Gly
                        675                 680                 685

Met Ser Gly Met Gly Gly Met Gly Gly Met Gly Gly Met Gly Gly Ala
                690                 695                 700

Gly Ala Ala Thr Thr Gln Ala Ala Gly Gly Asn Ala Glu Ala Glu Met
        705                 710                 715                 720

Leu Gln Asn Leu Met Asn Glu Ile Asn Arg Leu Lys Arg Glu Leu Gly
                        725                 730                 735

Glu

<210> SEQ ID NO 7
<211> LENGTH: 2448
<212> TYPE: DNA
<213> ORGANISM: Chlamydomonas reinhardtii

<400> SEQUENCE: 7
catctgtcgc caagcaagca ttaaacatgg attatggagg cgccctgagt gccgttgggc       60
gcgagctgct atttgtaacg aacccagtag tcgtcaatgg ctctgtactt gtgcctgagg      120
accagtgtta ctgcgcgggc tggattgagt cgcgtggcac aaacggtgcc caaacggcgt      180
cgaacgtgct gcaatggctt gctgctggct tctccatcct actgcttatg ttttacgcct      240
accaaacatg gaagtcaacc tgcggctggg aggagatcta tgtgtgcgct atcgagatgg      300
tcaaggtgat tctcgagttc ttcttcgagt ttaagaaccc gtccatgctg tatctagcca      360
caggccaccg cgtccagtgg ttgcgttacg ccgagtggct tctcacctgc ccggtcattc      420
tcattcacct gtcaaacctg acgggcttgt ccaacgacta cagcaggcgc accatgggtc      480
tgcttgtgtc tgatattggc acaattgtgt ggggcgccac ttccgccatg gccaccggat      540
acgtcaaggt catcttcttc tgcctgggtc tgtgttatgg tgctaacacg ttctttcacg      600
ctgccaaggc ctacatcgag ggttaccaca ccgtgccgaa gggccggtgt cgccaggtgg      660
tgactggcat ggcttggctc ttcttcgtat catgggggtat gttccccatc ctgttcatcc      720
tcggccccga gggcttcggc gtcctgagcg tgtacggctc accgtcggc cacaccatca      780 ttgacctgat gtcgaagaac tgctgggggtc tgctcggcca ctacctgcgc gtgctgatcc      840
acgagcatat cctcatccac ggcgacattc gcaagaccac caaattgaac attggtggca      900
ctgagattga ggtcgagacg ctggtggagg acgaggccga ggctggcgcg gtcaacaagg      960
gcaccggcaa gtacgcctcc cgcgagtcct tcctggtcat gcgcgacaag atgaaggaga     1020
agggcattga cgtgcgcgcc tctctggaca acagcaagga ggtggagcag agcaggccg     1080 ccagggctgc catgatgatg atgaacggca atggcatggg tatgggaatg ggaatgaacg     1140
gcatgaacgg aatgggcggt atgaacggga tggctggcgg cgccaagccc ggcctggagc     1200
tcactccgca gctacagccc ggccgcgtca tcctggcggt gccggacatc agcatggttg     1260
```

-continued

```
acttcttccg cgagcagttt gctcagctat cggtgacgta cgagctggtg ccggccctgg   1320
gcgctgacaa cacactggcg ctggttacgc aggcgcagaa cctgggcggc gtggactttg   1380
tgttgattca ccccgagttc ctgcgcgacc gctctagcac cagcatcctg agccgcctgc   1440
gcggcgcggg ccagcgtgtg gctgcgttcg gctgggcgca gctggggccc atgcgtgacc   1500
tgatcgagtc cgcaaacctg gacggctggc tggagggccc ctcgttcgga cagggcatcc   1560
tgccggccca tcgttgcc ctggtggcca agatgcagca gatgcgcaag atgcagcaga   1620
tgcagcagat tggcatgatg accggcggca tgaacggcat gggcggcggt atgggcggcg   1680
gcatgaacgg catgggcggc ggcaacggca tgaacaacat gggcaacggc atgggcggcg   1740
gcatgggcaa cggcatgggc ggcaatggca tgaacggaat gggtggcggc aacggcatga   1800
acaacatggg cggcaacgga atggccggca acggaatggg cggcggcatg gcggcaacg   1860
gtatgggtgg ctccatgaac ggcatgagct ccggcgtggt ggccaacgtg acgccctccg   1920
ccgccggcgg catgggcggc atgatgaacg cggcatggc tgcgccccag tcgcccggca   1980
tgaacggcgg ccgcctgggt accaacccgc tcttcaacgc cgcgccctca ccgctcagct   2040
cgcagctcgg tgccgaggca ggcatgggca gcatgggagg catgggcgga atgagcggaa   2100
tgggaggcat gggtggaatg ggggcatgg gcggcgccgg cgccgccacg acgcaggctg   2160
cgggcggcaa cgcggaggcg gagatgctgc agaatctcat gaacgagatc aatcgcctga   2220
agcgcgagct tggcgagtaa aaggctggag gccggtactg cgatacctgc gagctcgcgc   2280
gcctgactcg tcgtacacac ggctcaggag cacgcgcgcg tggacttctc aacctgtgtg   2340
caacgtatct agagcggcct gtgcgcgacc gtccgtgagc attccggtgc gatcttcccg   2400
ccttcgcacc gcaagttccc ttcctggccc tgctgcgcct gacgcatc                 2448
```

<210> SEQ ID NO 8
<211> LENGTH: 737
<212> TYPE: PRT
<213> ORGANISM: Chlamydomonas reinhardtii

<400> SEQUENCE: 8

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160
```

-continued

Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
        195                 200                 205
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
            260                 265                 270
Glu His Ile Leu Ile His Gly Asp Ile Arg Lys Thr Thr Lys Leu Asn
        275                 280                 285
Ile Gly Gly Thr Glu Ile Glu Val Glu Thr Leu Val Glu Asp Glu Ala
    290                 295                 300
Glu Ala Gly Ala Val Asn Lys Gly Thr Gly Lys Tyr Ala Ser Arg Glu
305                 310                 315                 320
Ser Phe Leu Val Met Arg Asp Lys Met Lys Glu Lys Gly Ile Asp Val
                325                 330                 335
Arg Ala Ser Leu Asp Asn Ser Lys Glu Val Glu Gln Glu Gln Ala Ala
            340                 345                 350
Arg Ala Ala Met Met Met Met Asn Gly Asn Gly Met Gly Met Gly Met
        355                 360                 365
Gly Met Asn Gly Met Asn Gly Met Gly Met Asn Gly Met Ala Gly
    370                 375                 380
Gly Ala Lys Pro Gly Leu Glu Leu Thr Pro Gln Leu Gln Pro Gly Arg
385                 390                 395                 400
Val Ile Leu Ala Val Pro Asp Ile Ser Met Val Asp Phe Phe Arg Glu
                405                 410                 415
Gln Phe Ala Gln Leu Ser Val Thr Tyr Glu Leu Val Pro Ala Leu Gly
            420                 425                 430
Ala Asp Asn Thr Leu Ala Leu Val Thr Gln Ala Gln Asn Leu Gly Gly
        435                 440                 445
Val Asp Phe Val Leu Ile His Pro Glu Phe Leu Arg Asp Arg Ser Ser
    450                 455                 460
Thr Ser Ile Leu Ser Arg Leu Arg Gly Ala Gly Gln Arg Val Ala Ala
465                 470                 475                 480
Phe Gly Trp Ala Gln Leu Gly Pro Met Arg Asp Leu Ile Glu Ser Ala
                485                 490                 495
Asn Leu Asp Gly Trp Leu Glu Gly Pro Ser Phe Gly Gln Gly Ile Leu
            500                 505                 510
Pro Ala His Ile Val Ala Leu Val Ala Lys Met Gln Gln Met Arg Lys
        515                 520                 525
Met Gln Gln Met Gln Gln Ile Gly Met Met Thr Gly Gly Met Asn Gly
    530                 535                 540
Met Gly Gly Gly Met Gly Gly Gly Met Asn Gly Met Gly Gly Gly Asn
545                 550                 555                 560
Gly Met Asn Asn Met Gly Asn Gly Met Gly Gly Gly Met Gly Asn Gly
                565                 570                 575
Met Gly Gly Asn Gly Met Asn Gly Met Gly Gly Gly Asn Gly Met Asn

```
                      580              585              590
Asn Met Gly Gly Asn Gly Met Ala Gly Asn Gly Met Gly Gly Gly Met
                595              600              605
Gly Gly Asn Gly Met Gly Gly Ser Met Asn Gly Met Ser Ser Gly Val
            610              615              620
Val Ala Asn Val Thr Pro Ser Ala Ala Gly Met Gly Gly Met Met
625              630              635              640
Asn Gly Gly Met Ala Ala Pro Gln Ser Pro Gly Met Asn Gly Arg
                645              650              655
Leu Gly Thr Asn Pro Leu Phe Asn Ala Ala Pro Ser Pro Leu Ser Ser
            660              665              670
Gln Leu Gly Ala Glu Ala Gly Met Gly Ser Met Gly Gly Met Gly Gly
                675              680              685
Met Ser Gly Met Gly Gly Met Gly Gly Met Gly Gly Met Gly Gly Ala
            690              695              700
Gly Ala Ala Thr Thr Gln Ala Ala Gly Gly Asn Ala Glu Ala Glu Met
705              710              715              720
Leu Gln Asn Leu Met Asn Glu Ile Asn Arg Leu Lys Arg Glu Leu Gly
                725              730              735
Glu

<210> SEQ ID NO 9
<211> LENGTH: 3033
<212> TYPE: DNA
<213> ORGANISM: Artificial Sequence
<220> FEATURE:
<223> OTHER INFORMATION: ChR2 mutant

<400> SEQUENCE: 9
atggattacc ctgtggcccg gtccctgatt gtaagatacc ccaccgatct gggcaatgga     60
accgtgtgca tgcccagagg acaatgctac tgcgaggggt ggctgaggag ccggggcact    120
agtatcgaaa aaccatcgc tatcaccctc cagtgggtag tgttcgctct gtccgtagcc    180
tgtctcggct ggtatgcata ccaagcctgg agggctacct gtgggtggga ggaagtatac    240
gtggccctga tcgagatgat gaagtccatc atcgaggctt ccatgagtt cgactcccca    300
gccacactct ggctcagcag tgggaatggc gtagtgtgga tgagatatgg agagtggctg    360
ctgacctgtc ccgtcctgct cattcatctg tccaatctga ccgggctgaa agatgactac    420
tccaagagaa caatgggact gctggtgagt gacgtggggt gtattgtgtg gggagccacc    480
tccgccatgt gcactggatg gaccaagatc ctcttttttcc tgatttccct ctcctatggg    540
atgtatacat acttccacgc cgctaaggtg tatattgagg ccttccacac tgtacctaaa    600
ggcatctgta gggagctcgt gcgggtgatg gcatggacct tctttgtggc ctggggggatg    660
ttccccgtgc tgttcctcct cggcactgag ggatttggcc acattagtcc ttacgggtcc    720
gcaattggac actccatcct ggatctgatt gccaagaata tgggggggt gctgggaaat    780
tatctgcggg taaagatcca cgagcatatc ctgctgtatg gcgatatcag aagaagcag    840
aaatcacca ttgctggaca ggaaatggag gtggagacac tggtagcaga ggaggaggac    900
gggaccgcgg tcgccaccat ggtgtctaag gcgaagagc tgattaagga aacatgcac    960
atgaagctgt acatggaggg caccgtgaac aaccaccact caagtgcac atccgagggc    1020
gaaggcaagc cctacgaggg cacccagacc atgagaatca aggtggtcga gggcggcct    1080
ctcccttcg ccttcgacat cctggctacc agcttcatgt acggcagcaa aaccttcatc    1140
```

| | |
|---|---|
| aaccacaccc agggcatccc cgacttcttt aagcagtcct ccctgaggg cttcacatgg | 1200 |
| gagagagtca ccacatacga agacgggggc gtgctgaccg ctacccagga caccagcctc | 1260 |
| caggacggct gcctcatcta caacgtcaag atcagagggg tgaacttccc atccaacggc | 1320 |
| cctgtgatgc agaagaaaac actcggctgg gaggcctcca ccgagatgct gtaccccgct | 1380 |
| gacggcggcc tggaaggcag agccgacatg ccctgaagc tcgtgggcgg gggccacctg | 1440 |
| atctgcaact tgaagaccac atacagatcc aagaaacccg ctaagaacct caagatgccc | 1500 |
| ggcgtctact atgtggacag aagactggaa agaatcaagg aggccgacaa agagacctac | 1560 |
| gtcgagcagc acgaggtggc tgtggccaga tactgcgacc tccctagcaa actggggcac | 1620 |
| aaacttaatt gcctgcagga agaagtca tgcagccagc gcatggccga attccggcaa | 1680 |
| tactgttgga acccggacac tgggcagatg ctgggccgca ccccagcccg gtgggtgtgg | 1740 |
| atcagcctgt actatgcagc tttctacgtg gtcatgactg ggctctttgc cttgtgcatc | 1800 |
| tatgtgctga tgcagaccat tgatccctac accccgact accaggacca gttaaagtca | 1860 |
| ccgggggtaa ccttgagacc ggatgtgtat ggggaaagag ggctgcagat tcctacaac | 1920 |
| atctctgaaa acagctctag acaggcccag atcaccggac gtccggagac tgagacattg | 1980 |
| ccaccggtgg actacggggg ggccctgagc gctgtgggca gagaactcct gttcgtgaca | 2040 |
| aatccagtcg tggtgaacgg ctccgtactc gtacccgagg atcagtgcta ttgcgcagga | 2100 |
| tggatcgaga gcagaggcac aaacggcgca cagactgcat ccaacgtgct ccagtggttg | 2160 |
| gccgcaggct tttccattct cctgctcatg ttttacgcct accagacttg gaagtccaca | 2220 |
| tgtggctggg aggaaatcta cgtgtgtgca atcgaaatgg tgaaggtgat cctggagttt | 2280 |
| ttcttcgaat ttaaaaaccc aagcatgctg tacctggcta ctggccacag agtgcagtgg | 2340 |
| ctgcggtatg ccgaatggct gctgacttgc ccagtgattt gcatccacct gtccaacctg | 2400 |
| actgggctgt ctaacgatta cagtaggaga acaatgggac tgctcgtatc cgacatcggc | 2460 |
| actatcgtat ggggcgcaac tagtgccatg gccactggat acgtgaaagt gatcttcttc | 2520 |
| tgcctgggac tctgctacgg agcaaacaca ttttttcatg ccgcaaaagc atatatcgag | 2580 |
| gggtatcata ccgtcccaaa gggccggtgt agacaagtgg tgactggcat ggcttggctg | 2640 |
| ttcttcgtgt cctgggggat gtttcccatc ctctttatcc tgggcccaga aggcttcggg | 2700 |
| gtgctgagtg tgtatggcag taccgtagga cacactatca ttgacctgat gagcaaaaac | 2760 |
| tgctgggggc tgctcggcca ctacctgaga gtactcatcc acgagcatat cctgattcat | 2820 |
| ggcgatatcc ggaaaactac caagctcaat atcgggggca ccgagattga agtggagaca | 2880 |
| ctcgtggagg acgaggccga ggccggagca gtgaacaaag gcactggcaa gtatgcctcc | 2940 |
| agagaatcct ttctggtgat gcgggacaaa atgaaggaga aaggcattga tgtacggtgc | 3000 |
| agtaatgcca aagccgtcga gactgatgtg tag | 3033 |

```
<210> SEQ ID NO 10
<211> LENGTH: 1010
<212> TYPE: PRT
<213> ORGANISM: Artificial Sequence
<220> FEATURE:
<223> OTHER INFORMATION: ChR2 mutant

<400> SEQUENCE: 10

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30
```

```
Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
 50                  55                  60

Tyr Ala Tyr Gln Ala Trp Arg Ala Thr Cys Gly Trp Glu Glu Val Tyr
 65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
 130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
                180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
 210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
                260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Asp Gly Thr Ala Val
 290                 295                 300

Ala Thr Met Val Ser Lys Gly Glu Glu Leu Ile Lys Glu Asn Met His
305                 310                 315                 320

Met Lys Leu Tyr Met Glu Gly Thr Val Asn Asn His His Phe Lys Cys
                325                 330                 335

Thr Ser Glu Gly Glu Gly Lys Pro Tyr Glu Gly Thr Gln Thr Met Arg
            340                 345                 350

Ile Lys Val Val Glu Gly Gly Pro Leu Pro Phe Ala Phe Asp Ile Leu
            355                 360                 365

Ala Thr Ser Phe Met Tyr Gly Ser Lys Thr Phe Ile Asn His Thr Gln
370                 375                 380

Gly Ile Pro Asp Phe Phe Lys Gln Ser Phe Pro Glu Gly Phe Thr Trp
385                 390                 395                 400

Glu Arg Val Thr Thr Tyr Glu Asp Gly Gly Val Leu Thr Ala Thr Gln
            405                 410                 415

Asp Thr Ser Leu Gln Asp Gly Cys Leu Ile Tyr Asn Val Lys Ile Arg
            420                 425                 430

Gly Val Asn Phe Pro Ser Asn Gly Pro Val Met Gln Lys Lys Thr Leu
            435                 440                 445
```

-continued

```
Gly Trp Glu Ala Ser Thr Glu Met Leu Tyr Pro Ala Asp Gly Gly Leu
    450                 455                 460
Glu Gly Arg Ala Asp Met Ala Leu Lys Leu Val Gly Gly Gly His Leu
465                 470                 475                 480
Ile Cys Asn Leu Lys Thr Thr Tyr Arg Ser Lys Lys Pro Ala Lys Asn
                    485                 490                 495
Leu Lys Met Pro Gly Val Tyr Val Asp Arg Arg Leu Glu Arg Ile
                500                 505                 510
Lys Glu Ala Asp Lys Glu Thr Tyr Val Glu Gln His Glu Val Ala Val
                515                 520                 525
Ala Arg Tyr Cys Asp Leu Pro Ser Lys Leu Gly His Lys Leu Asn Cys
530                 535                 540
Leu Gln Glu Lys Lys Ser Cys Ser Gln Arg Met Ala Glu Phe Arg Gln
545                 550                 555                 560
Tyr Cys Trp Asn Pro Asp Thr Gly Gln Met Leu Gly Arg Thr Pro Ala
                565                 570                 575
Arg Trp Val Trp Ile Ser Leu Tyr Tyr Ala Ala Phe Tyr Val Val Met
                580                 585                 590
Thr Gly Leu Phe Ala Leu Cys Ile Tyr Val Leu Met Gln Thr Ile Asp
                595                 600                 605
Pro Tyr Thr Pro Asp Tyr Gln Asp Gln Leu Lys Ser Pro Gly Val Thr
                610                 615                 620
Leu Arg Pro Asp Val Tyr Gly Glu Arg Gly Leu Gln Ile Ser Tyr Asn
625                 630                 635                 640
Ile Ser Glu Asn Ser Ser Arg Gln Ala Gln Ile Thr Gly Arg Pro Glu
                645                 650                 655
Thr Glu Thr Leu Pro Pro Val Asp Tyr Gly Gly Ala Leu Ser Ala Val
                660                 665                 670
Gly Arg Glu Leu Leu Phe Val Thr Asn Pro Val Val Asn Gly Ser
                675                 680                 685
Val Leu Val Pro Glu Asp Gln Cys Tyr Cys Ala Gly Trp Ile Glu Ser
            690                 695                 700
Arg Gly Thr Asn Gly Ala Gln Thr Ala Ser Asn Val Leu Gln Trp Leu
705                 710                 715                 720
Ala Ala Gly Phe Ser Ile Leu Leu Met Phe Tyr Ala Tyr Gln Thr
                725                 730                 735
Trp Lys Ser Thr Cys Gly Trp Glu Glu Ile Tyr Val Cys Ala Ile Glu
                740                 745                 750
Met Val Lys Val Ile Leu Glu Phe Phe Phe Glu Phe Lys Asn Pro Ser
            755                 760                 765
Met Leu Tyr Leu Ala Thr Gly His Arg Val Gln Trp Leu Arg Tyr Ala
770                 775                 780
Glu Trp Leu Leu Thr Cys Pro Val Ile Cys Ile His Leu Ser Asn Leu
785                 790                 795                 800
Thr Gly Leu Ser Asn Asp Tyr Ser Arg Arg Thr Met Gly Leu Leu Val
                805                 810                 815
Ser Asp Ile Gly Thr Ile Val Trp Gly Ala Thr Ser Ala Met Ala Thr
                820                 825                 830
Gly Tyr Val Lys Val Ile Phe Phe Cys Leu Gly Leu Cys Tyr Gly Ala
                835                 840                 845
Asn Thr Phe Phe His Ala Ala Lys Ala Tyr Ile Glu Gly Tyr His Thr
850                 855                 860
Val Pro Lys Gly Arg Cys Arg Gln Val Val Thr Gly Met Ala Trp Leu
```

```
                865                 870                 875                 880
        Phe Phe Val Ser Trp Gly Met Phe Pro Ile Leu Phe Ile Leu Gly Pro
                        885                 890                 895

Glu Gly Phe Gly Val Leu Ser Val Tyr Gly Ser Thr Val Gly His Thr
                    900                 905                 910

Ile Ile Asp Leu Met Ser Lys Asn Cys Trp Gly Leu Leu Gly His Tyr
                915                 920                 925

Leu Arg Val Leu Ile His Glu His Ile Leu Ile His Gly Asp Ile Arg
            930                 935                 940

Lys Thr Thr Lys Leu Asn Ile Gly Gly Thr Glu Ile Glu Val Glu Thr
        945                 950                 955                 960

Leu Val Glu Asp Glu Ala Glu Ala Gly Ala Val Asn Lys Gly Thr Gly
                        965                 970                 975

Lys Tyr Ala Ser Arg Glu Ser Phe Leu Val Met Arg Asp Lys Met Lys
                    980                 985                 990

Glu Lys Gly Ile Asp Val Arg Cys Ser Asn Ala Lys Ala Val Glu Thr
                995                 1000                1005

Asp Val
            1010

<210> SEQ ID NO 11
<211> LENGTH: 3033
<212> TYPE: DNA
<213> ORGANISM: Artificial Sequence
<220> FEATURE:
<223> OTHER INFORMATION: ChR2 mutant

<400> SEQUENCE: 11
atggattacc ctgtggcccg gtccctgatt gtaagatacc ccaccgatct gggcaatgga      60
accgtgtgca tgcccagagg acaatgctac tgcgaggggt ggctgaggag ccggggcact     120
agtatcgaaa aaaccatcgc tatcaccctc cagtgggtag tgttcgctct gtccgtagcc     180
tgtctcggct ggtatgcata ccaagcctgg agggctacct gtgggtggga ggaagtatac     240
gtggccctga tcgagatgat gaagtccatc atcgaggctt ccatgagtt cgactcccca     300 gccacactct ggctcagcag tgggaatggc gtagtgtgga tgagatatgg agagtggctg     360
ctgacctgtc ccgtcctgct cattcatctg tccaatctga ccgggctgaa agatgactac     420
tccaagagaa caatgggact gctggtgagt gacgtgggt gtattgtgtg gggagccacc     480
tccgccatgt gcactggatg gaccaagatc ctcttttttcc tgatttccct ctcctatggg     540
atgtatacat acttccacgc cgctaaggtg tatattgagg ccttccacac tgtacctaaa     600
ggcatctgta gggagctcgt gcgggtgatg gcatggacct tctttgtggc ctggggatg     660 ttccccgtgc tgttcctcct cggcactgag ggatttggcc acattagtcc ttacgggtcc     720
gcaattggac actccatcct ggatctgatt gccaagaata tgtgggggt gctgggaaat     780 tatctgcggg taaagatcca cgagcatatc ctgctgtatg cgatatcag aaagaagcag     840 aaaatcacca ttgctggaca ggaaatggag gtggagacac tggtagcaga ggaggaggac     900
gggaccgcgg tcgccaccat ggtgtctaag ggcgaagagc tgattaagga gaacatgcac     960
atgaagctgt acatggaggg caccgtgaac aaccaccact caagtgcac atccgagggc    1020 gaaggcaagc cctacgaggg cacccagacc atgagaatca aggtggtcga gggcggccct    1080
ctccccttcg cctttgacat cctggctacc agcttcatgt acggcagcaa aaccttcatc    1140
aaccacaccc agggcatccc cgacttcttt aagcagtcct ccctgaggg cttcacatgg    1200
```

| | |
|---|---|
| gagagagtca ccacatacga agacgggggc gtgctgaccg ctacccagga caccagcctc | 1260 |
| caggacggct gcctcatcta caacgtcaag atcagagggg tgaacttccc atccaacggc | 1320 |
| cctgtgatgc agaagaaaac actcggctgg gaggcctcca ccgagatgct gtaccccgct | 1380 |
| gacgcggcc tggaaggcag agccgacatg gccctgaagc tcgtgggcgg gggccacctg | 1440 |
| atctgcaact tgaagaccac atacagatcc aagaaacccg ctaagaacct caagatgccc | 1500 |
| ggcgtctact atgtggacag aagactggaa agaatcaagg aggccgacaa agagacctac | 1560 |
| gtcgagcagc acgaggtggc tgtggccaga tactgcgacc tccctagcaa actggggcac | 1620 |
| aaacttaatt gcctgcagga gaagaagtca tgcagccagc gcatggccga attccggcaa | 1680 |
| tactgttgga acccggacac tgggcagatg ctgggccgca ccccagcccg gtgggtgtgg | 1740 |
| atcagcctgt actatgcagc tttctacgtg gtcatgactg gctcttttgc cttgtgcatc | 1800 |
| tatgtgctga tgcagaccat tgatccctac acccccgact accaggacca gttaaagtca | 1860 |
| ccggggta ccttgagacc ggatgtgtat ggggaaagag ggctgcagat ttcctacaac | 1920 |
| atctctgaaa acagctctag acaggcccag atcaccggac gtccggagac tgagacattg | 1980 |
| ccaccggtgg actacggggg ggccctgagc gctgtgggca gagaactcct gttcgtgaca | 2040 |
| aatccagtcg tggtgaacgg ctccgtactc gtacccgagg atcagtgcta ttgcgcagga | 2100 |
| tggatcgaga gcagaggcac aaacggcgca cagactgcat ccaacgtgct ccagtggttg | 2160 |
| gccgcaggct tttccattct cctgctcatg ttttacgcct accagacttg gaagtccaca | 2220 |
| tgtggctggg aggaaatcta cgtgtgtgca atcgaaatgg tgaaggtgat cctggagttt | 2280 |
| ttcttcgaat ttaaaaaccc aagcatgctg tacctggcta ctggccacag agtgcagtgg | 2340 |
| ctgcggtatg ccgaatggct gctgacttgc ccagtgattc tgatccacct gtccaacctg | 2400 |
| actgggctgt ctaacgatta cagtaggaga acaatgggac tgctcgtatc cgacatcggc | 2460 |
| actatcgtat ggggcgcaac tagtgccatg gccactggat acgtgaaagt gatcttcttc | 2520 |
| tgcctgggac tctgctacgg agcaaacaca ttttttcatg ccgcaaaagc atatatcgag | 2580 |
| gggtatcata ccgtcccaaa gggccggtgt agacaagtgg tgactggcat ggcttggctg | 2640 |
| ttcttcgtgt cctgggggat gtttcccatc ctctttatcc tgggcccaga aggcttcggg | 2700 |
| gtgctgagtg tgtatggcag taccgtagga cacactatca ttgacctgat gagcaaaaac | 2760 |
| tgctgggggc tgctcggcca ctacctgaga gtactcatcc acgagcatat cctgattcat | 2820 |
| ggcgatatcc ggaaaactac caagctcaat atcggggca ccgagattga agtggagaca | 2880 |
| ctcgtggagg acgaggccga ggccggagca gtgaacaaag cactggcaa gtatgcctcc | 2940 |
| agagaatcct ttctggtgat gcgggacaaa atgaaggaga aaggcattga tgtacggtgc | 3000 |
| agtaatgcca aagccgtcga gactgatgtg tag | 3033 |

<210> SEQ ID NO 12
<211> LENGTH: 1010
<212> TYPE: PRT
<213> ORGANISM: Artificial Sequence
<220> FEATURE:
<223> OTHER INFORMATION: ChR2 mutant construct

<400> SEQUENCE: 12

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile

```
                35                  40                  45
Thr Leu Gln Trp Val Val Phe Ala Leu Ser Val Ala Cys Leu Gly Trp
 50                  55                  60

Tyr Ala Tyr Gln Ala Trp Arg Ala Thr Cys Gly Trp Glu Glu Val Tyr
 65                  70                  75                  80

Val Ala Leu Ile Glu Met Met Lys Ser Ile Glu Ala Phe His Glu
                 85                  90                  95

Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
            130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
            275                 280                 285

Met Glu Val Glu Thr Leu Val Ala Glu Glu Asp Gly Thr Ala Val
290                 295                 300

Ala Thr Met Val Ser Lys Gly Glu Glu Leu Ile Lys Glu Asn Met His
305                 310                 315                 320

Met Lys Leu Tyr Met Glu Gly Thr Val Asn Asn His His Phe Lys Cys
                325                 330                 335

Thr Ser Glu Gly Glu Gly Lys Pro Tyr Glu Gly Thr Gln Thr Met Arg
            340                 345                 350

Ile Lys Val Val Glu Gly Gly Pro Leu Pro Phe Ala Phe Asp Ile Leu
            355                 360                 365

Ala Thr Ser Phe Met Tyr Gly Ser Lys Thr Phe Ile Asn His Thr Gln
            370                 375                 380

Gly Ile Pro Asp Phe Phe Lys Gln Ser Phe Pro Glu Gly Phe Thr Trp
385                 390                 395                 400

Glu Arg Val Thr Thr Tyr Glu Asp Gly Gly Val Leu Thr Ala Thr Gln
                405                 410                 415

Asp Thr Ser Leu Gln Asp Gly Cys Leu Ile Tyr Asn Val Lys Ile Arg
            420                 425                 430

Gly Val Asn Phe Pro Ser Asn Gly Pro Val Met Gln Lys Lys Thr Leu
            435                 440                 445

Gly Trp Glu Ala Ser Thr Glu Met Leu Tyr Pro Ala Asp Gly Gly Leu
450                 455                 460
```

```
Glu Gly Arg Ala Asp Met Ala Leu Lys Leu Val Gly Gly His Leu
465                 470                 475                 480

Ile Cys Asn Leu Lys Thr Thr Tyr Arg Ser Lys Lys Pro Ala Lys Asn
                485                 490                 495

Leu Lys Met Pro Gly Val Tyr Tyr Val Asp Arg Arg Leu Glu Arg Ile
            500                 505                 510

Lys Glu Ala Asp Lys Glu Thr Tyr Val Glu Gln His Glu Val Ala Val
                515                 520                 525

Ala Arg Tyr Cys Asp Leu Pro Ser Lys Leu Gly His Lys Leu Asn Cys
        530                 535                 540

Leu Gln Glu Lys Lys Ser Cys Ser Gln Arg Met Ala Glu Phe Arg Gln
545                 550                 555                 560

Tyr Cys Trp Asn Pro Asp Thr Gly Gln Met Leu Gly Arg Thr Pro Ala
                565                 570                 575

Arg Trp Val Trp Ile Ser Leu Tyr Tyr Ala Ala Phe Tyr Val Val Met
            580                 585                 590

Thr Gly Leu Phe Ala Leu Cys Ile Tyr Val Leu Met Gln Thr Ile Asp
        595                 600                 605

Pro Tyr Thr Pro Asp Tyr Gln Asp Gln Leu Lys Ser Pro Gly Val Thr
            610                 615                 620

Leu Arg Pro Asp Val Tyr Gly Glu Arg Gly Leu Gln Ile Ser Tyr Asn
625                 630                 635                 640

Ile Ser Glu Asn Ser Ser Arg Gln Ala Gln Ile Thr Gly Arg Pro Glu
                645                 650                 655

Thr Glu Thr Leu Pro Pro Val Asp Tyr Gly Gly Ala Leu Ser Ala Val
            660                 665                 670

Gly Arg Glu Leu Leu Phe Val Thr Asn Pro Val Val Val Asn Gly Ser
        675                 680                 685

Val Leu Val Pro Glu Asp Gln Cys Tyr Cys Ala Gly Trp Ile Glu Ser
        690                 695                 700

Arg Gly Thr Asn Gly Ala Gln Thr Ala Ser Asn Val Leu Gln Trp Leu
705                 710                 715                 720

Ala Ala Gly Phe Ser Ile Leu Leu Leu Met Phe Tyr Ala Tyr Gln Thr
            725                 730                 735

Trp Lys Ser Thr Cys Gly Trp Glu Glu Ile Tyr Val Cys Ala Ile Glu
            740                 745                 750

Met Val Lys Val Ile Leu Glu Phe Phe Phe Glu Phe Lys Asn Pro Ser
        755                 760                 765

Met Leu Tyr Leu Ala Thr Gly His Arg Val Gln Trp Leu Arg Tyr Ala
        770                 775                 780

Glu Trp Leu Leu Thr Cys Pro Val Ile Leu Ile His Leu Ser Asn Leu
785                 790                 795                 800

Thr Gly Leu Ser Asn Asp Tyr Ser Arg Arg Thr Met Gly Leu Leu Val
                805                 810                 815

Ser Asp Ile Gly Thr Ile Val Trp Gly Ala Thr Ser Ala Met Ala Thr
            820                 825                 830

Gly Tyr Val Lys Val Ile Phe Phe Cys Leu Gly Leu Cys Tyr Gly Ala
            835                 840                 845

Asn Thr Phe Phe His Ala Ala Lys Ala Tyr Ile Glu Gly Tyr His Thr
        850                 855                 860

Val Pro Lys Gly Arg Cys Arg Gln Val Val Thr Gly Met Ala Trp Leu
865                 870                 875                 880
```

```
Phe Phe Val Ser Trp Gly Met Phe Pro Ile Leu Phe Ile Leu Gly Pro
                885                 890                 895
Glu Gly Phe Gly Val Leu Ser Val Tyr Gly Ser Thr Val Gly His Thr
            900                 905                 910
Ile Ile Asp Leu Met Ser Lys Asn Cys Trp Gly Leu Leu Gly His Tyr
            915                 920                 925
Leu Arg Val Leu Ile His Glu His Ile Leu Ile His Gly Asp Ile Arg
930                 935                 940
Lys Thr Thr Lys Leu Asn Ile Gly Gly Thr Glu Ile Glu Val Glu Thr
945                 950                 955                 960
Leu Val Glu Asp Glu Ala Glu Ala Gly Ala Val Asn Lys Gly Thr Gly
            965                 970                 975
Lys Tyr Ala Ser Arg Glu Ser Phe Leu Val Met Arg Asp Lys Met Lys
            980                 985                 990
Glu Lys Gly Ile Asp Val Arg Cys Ser Asn Ala Lys Ala Val Glu Thr
            995                 1000                1005
Asp Val
    1010

<210> SEQ ID NO 13
<211> LENGTH: 315
<212> TYPE: PRT
<213> ORGANISM: Artificial Sequence
<220> FEATURE:
<223> OTHER INFORMATION: ChR2 mutant construct

<400> SEQUENCE: 13

Met Asp Tyr Gly Gly Ala Leu Ser Ala Val Gly Arg Glu Leu Leu Phe
1               5                   10                  15
Val Thr Asn Pro Val Val Asn Gly Ser Val Leu Val Pro Glu Asp
            20                  25                  30
Gln Cys Tyr Cys Ala Gly Trp Ile Glu Ser Arg Gly Thr Asn Gly Ala
        35                  40                  45
Gln Thr Ala Ser Asn Val Leu Gln Trp Leu Ala Ala Gly Phe Ser Ile
    50                  55                  60
Leu Leu Leu Met Phe Tyr Ala Tyr Gln Thr Trp Lys Ser Thr Cys Gly
65                  70                  75                  80
Trp Glu Glu Ile Tyr Val Cys Ala Ile Glu Met Val Lys Val Ile Leu
                85                  90                  95
Glu Phe Phe Phe Glu Phe Lys Asn Pro Ser Met Leu Tyr Leu Ala Thr
            100                 105                 110
Gly His Arg Val Gln Trp Leu Arg Tyr Ala Glu Trp Leu Leu Thr Cys
        115                 120                 125
Pro Val Ile Cys Ile His Leu Ser Asn Leu Thr Gly Leu Ser Asn Asp
    130                 135                 140
Tyr Ser Arg Arg Thr Met Gly Leu Leu Val Ser Asp Ile Gly Thr Ile
145                 150                 155                 160
Val Trp Gly Ala Thr Ser Ala Met Ala Thr Gly Tyr Val Lys Val Ile
                165                 170                 175
Phe Phe Cys Leu Gly Leu Cys Tyr Gly Ala Asn Thr Phe Phe His Ala
            180                 185                 190
Ala Lys Ala Tyr Ile Glu Gly Tyr His Thr Val Pro Lys Gly Arg Cys
        195                 200                 205
Arg Gln Val Val Thr Gly Met Ala Trp Leu Phe Phe Val Ser Trp Gly
    210                 215                 220
```

```
Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
        260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
        290                 295                 300

Glu Ala Gly Ala Val Asn Lys Gly Thr Gly Lys
305                 310                 315
```

<210> SEQ ID NO 14
<211> LENGTH: 315
<212> TYPE: PRT
<213> ORGANISM: Artificial Sequence
<220> FEATURE:
<223> OTHER INFORMATION: ChR2 mutant construct

<400> SEQUENCE: 14

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Cys Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270
```

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys
305                 310                 315

<210> SEQ ID NO 15
<211> LENGTH: 945
<212> TYPE: DNA
<213> ORGANISM: Artificial Sequence
<220> FEATURE:
<223> OTHER INFORMATION: ChR2 mutant construct

<400> SEQUENCE: 15

| | | | | | |
|---|---|---|---|---|---|
| atggactacg | gggggctct | gtctgctgtc | gggagggaac | tgctgtttgt | gactaaccct | 60 |
| gtcgtcgtga | acgggagtgt | gctggtccct | gaggaccagt | gctactgtgc | cggctggatc | 120 |
| gaatcacgcg | gaaccaacgg | ggcccagaca | gctagcaatg | tgctgcagtg | gctggccgct | 180 |
| gggtttagta | tcctgctgct | gatgttctac | gcctatcaga | cttggaagtc | aacctgcggc | 240 |
| tgggaggaaa | tctacgtgtg | cgctattgag | atggtgaaag | tgatcctgga | gttcttcttc | 300 |
| gagttcaaga | acccaagcat | gctgtacctg | gctactggac | accgagtgca | gtggctgaga | 360 |
| tatgcagaat | ggctgctgac | atgccccgtc | atctgcattc | acctgtccaa | cctgacaggc | 420 |
| ctgagcaatg | actactccag | agaactatgg | gactgctgg | tgtccgacat | cggctgcatt | 480 |
| gtctggggag | caacttctgc | tatggcaacc | ggatacgtga | aggtcatctt | tttctgcctg | 540 |
| gggctgtgct | atggcgcaaa | tacctttttc | cacgcagcca | aggcctacat | tgaggggtat | 600 |
| cataccgtgc | caaaaggccg | gtgccgacag | gtggtcacag | gaatggcttg | gctgtttttc | 660 |
| gtctcttggg | gaatgtttcc | catcctgttc | attctggggc | ctgaagggtt | cggcgtgctg | 720 |
| tctgtctacg | gaagtacagt | ggggcatact | atcattgacc | tgatgtccaa | aaactgttgg | 780 |
| ggcctgctgg | gacactatct | gagagtgctg | atccacgagc | atatcctgat | tcatggcgat | 840 |
| attcggaaga | ccacaaaact | gaatatcggc | ggaaccgaga | ttgaagtgga | aacactggtg | 900 |
| gaagacgagg | ctgaggctgg | ggctgtgaac | aaggggactg | gcaaa | | 945 |

<210> SEQ ID NO 16
<211> LENGTH: 315
<212> TYPE: PRT
<213> ORGANISM: Artificial Sequence
<220> FEATURE:
<223> OTHER INFORMATION: mutated Chop2

<400> SEQUENCE: 16

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

```
Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
            115                 120                 125

Pro Val Ile Cys Ile His Leu Ser Asn Leu Thr Gly Leu Ser Asn Asp
        130                 135                 140

Tyr Ser Arg Arg Thr Met Gly Leu Leu Val Ser Asp Ile Gly Cys Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val Asn Lys Gly Thr Gly Lys
305                 310                 315

<210> SEQ ID NO 17
<211> LENGTH: 315
<212> TYPE: PRT
<213> ORGANISM: Artificial Sequence
<220> FEATURE:
<223> OTHER INFORMATION: mutated Chop2

<400> SEQUENCE: 17

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
        130                 135                 140
```

Tyr Ser Arg Arg Thr Met Gly Leu Leu Val Ser Asp Ile Gly Ser Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys
305                 310                 315

<210> SEQ ID NO 18
<211> LENGTH: 945
<212> TYPE: DNA
<213> ORGANISM: Artificial Sequence
<220> FEATURE:
<223> OTHER INFORMATION: mutated Chop2

<400> SEQUENCE: 18
atggactacg gggggctct gtctgctgtc gggagggaac tgctgtttgt gactaaccct      60
gtcgtcgtga acgggagtgt gctggtccct gaggaccagt gctactgtgc cggctggatc     120
gaatcacgcg gaaccaacgg ggcccagaca gctagcaatg tgctgcagtg gctggccgct    180
gggtttagta tcctgctgct gatgttctac gcctatcaga cttggaagtc aacctgcggc    240
tgggaggaaa tctacgtgtg cgctattgag atggtgaaag tgatcctgga gttcttcttc    300
gagttcaaga acccaagcat gctgtacctg gctactggac accgagtgca gtggctgaga    360
tatgcagaat ggctgctgac atgccccgtc atctgcattc acctgtccaa cctgacaggc    420
ctgagcaatg actactccag gagaactatg ggactgctgg tgtccgacat cggcagcatt    480
gtctggggag caacttctgc tatggcaacc ggatacgtga aggtcatctt tttctgcctg    540
gggctgtgct atggcgcaaa tacctttttc cacgcagcca aggcctacat tgagggtat    600 cataccgtgc caaaaggccg tgccgacag gtggtcacag aatggcttg ctgttttc     660 gtctcttggg aatgtttcc catcctgttc attctgggc ctgaagggtt cggcgtgctg    720
tctgtctacg gaagtacagt ggggcatact atcattgacc tgatgtccaa aaactgttgg    780
ggcctgctgg gacactatct gagagtgctg atccacgagc atatcctgat tcatggcgat    840
attcggaaga ccacaaaact gaatatcggc ggaaccgaga ttgaagtgga aacactggtg    900
gaagacgagg ctgaggctgg ggctgtgaac aagggggactg gcaaa              945

<210> SEQ ID NO 19
<211> LENGTH: 315
<212> TYPE: PRT

<213> ORGANISM: Artificial Sequence
<220> FEATURE:
<223> OTHER INFORMATION: mutated Chop2

<400> SEQUENCE: 19

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Cys Ile His Leu Ser Asn Leu Thr Gly Leu Ser Asn Asp
        130                 135                 140

Tyr Ser Arg Arg Thr Met Gly Leu Leu Val Ser Asp Ile Gly Ser Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val Asn Lys Gly Thr Gly Lys
305                 310                 315
```

<210> SEQ ID NO 20
<211> LENGTH: 315
<212> TYPE: PRT
<213> ORGANISM: Artificial Sequence
<220> FEATURE:
<223> OTHER INFORMATION: mutated Chop2

<400> SEQUENCE: 20

```
Met Asp Tyr Gly Gly Ala Leu Ser Ala Val Gly Arg Glu Leu Leu Phe
1               5                   10                  15
```

```
Val Thr Asn Pro Val Val Asn Gly Ser Val Leu Val Pro Glu Asp
         20                  25                  30

Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Ala Gly Phe Ser Ile
         50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
            115                 120                 125

Pro Val Ile Ala Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
290                 295                 300

Glu Ala Gly Ala Val Asn Lys Gly Thr Gly Lys
305                 310                 315

<210> SEQ ID NO 21
<211> LENGTH: 945
<212> TYPE: DNA
<213> ORGANISM: Artificial Sequence
<220> FEATURE:
<223> OTHER INFORMATION: mutated Chop2

<400> SEQUENCE: 21
atggactacg ggggggctct gtctgctgtc gggagggaac tgctgtttgt gactaaccct      60
gtcgtcgtga acgggagtgt gctggtccct gaggaccagt gctactgtgc cggctggatc     120
gaatcacgcg gaaccaacgg ggcccagaca gctagcaatg tgctgcagtg gctggccgct     180
gggtttagta tcctgctgct gatgttctac gcctatcaga cttggaagtc aacctgcggc     240
tgggaggaaa tctacgtgtg cgctattgag atggtgaaag tgatcctgga gttcttcttc     300
gagttcaaga acccaagcat gctgtacctg gctactggac accgagtgca gtggctgaga     360
```

```
tatgcagaat ggctgctgac atgccccgtc atcgccattc acctgtccaa cctgacaggc    420
ctgagcaatg actactccag gagaactatg ggactgctgg tgtccgacat cggctgcatt    480
gtctggggag caacttctgc tatggcaacc ggatacgtga aggtcatctt tttctgcctg    540
gggctgtgct atggcgcaaa tacctttttc cacgcagcca aggcctacat tgaggggtat    600
cataccgtgc caaaaggccg tgtccgacag gtggtcacag gaatggcttg gctgtttttc    660
gtctcttggg gaatgtttcc catcctgttc attctggggc ctgaagggtt cggcgtgctg    720
tctgtctacg gaagtacagt ggggcatact atcattgacc tgatgtccaa aaactgttgg    780
ggcctgctgg gacactatct gagagtgctg atccacgagc atatcctgat tcatggcgat    840
attcggaaga ccacaaaact gaatatcggc ggaaccgaga ttgaagtgga aacactggtg    900
gaagacgagg ctgaggctgg ggctgtgaac aaggggactg gcaaa                    945
```

<210> SEQ ID NO 22
<211> LENGTH: 315
<212> TYPE: PRT
<213> ORGANISM: Artificial Sequence
<220> FEATURE:
<223> OTHER INFORMATION: mutated Chop2

<400> SEQUENCE: 22

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Ala Ile His Leu Ser Asn Leu Thr Gly Leu Ser Asn Asp
    130                 135                 140

Tyr Ser Arg Arg Thr Met Gly Leu Leu Val Ser Asp Ile Gly Cys Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
```

260                 265                 270
Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Asn Lys Gly Thr Gly Lys
305                 310                 315

<210> SEQ ID NO 23
<211> LENGTH: 315
<212> TYPE: PRT
<213> ORGANISM: Artificial Sequence
<220> FEATURE:
<223> OTHER INFORMATION: mutated Chop2

<400> SEQUENCE: 23

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Ala Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys 305                310                315

<210> SEQ ID NO 24
<211> LENGTH: 945
<212> TYPE: DNA
<213> ORGANISM: Artificial Sequence
<220> FEATURE:
<223> OTHER INFORMATION: mutated Chop2

<400> SEQUENCE: 24

```
atggactacg gggggctct gtctgctgtc gggagggaac tgctgtttgt gactaaccct      60
gtcgtcgtga acgggagtgt gctggtccct gaggaccagt gctactgtgc cggctggatc     120
gaatcacgcg gaaccaacgg ggcccagaca gctagcaatg tgctgcagtg gctggccgct    180
gggtttagta tcctgctgct gatgttctac gcctatcaga cttggaagtc aacctgcggc    240
tgggaggaaa tctacgtgtg cgctattgag atggtgaaag tgatcctgga gttcttcttc    300
gagttcaaga acccaagcat gctgtacctg ctactggac accgagtgca gtggctgaga    360
tatgcagaat ggctgctgac atgccccgtc atctgcattc acctgtccaa cctgacaggc    420
ctgagcaatg actactccag agaactatg ggactgctgg tgtccgacat cggcgccatt    480
gtctggggag caacttctgc tatggcaacc ggatacgtga aggtcatctt tttctgcctg    540
gggctgtgct atggcgcaaa tacctttttc cacgcagcca aggcctacat tgaggggtat    600
cataccgtgc aaaaggccg tgccgacag tggtcacag aatggcttg ctgtttttc    660
gtctcttggg aatgtttcc catcctgttc attctgggc ctgaagggt cggcgtgctg    720
tctgtctacg aagtacagt ggggcatact atcattgacc tgatgtccaa aaactgttgg    780
ggcctgctgg acactatct gagagtgctg atccacgagc atatcctgat tcatggcgat    840
attcggaaga ccacaaaact gaatatcggc ggaaccgaga ttgaagtgga aacactggtg    900
gaagacgagg ctgaggctgg ggctgtgaac aaggggactg gcaaa                    945
```

<210> SEQ ID NO 25
<211> LENGTH: 315
<212> TYPE: PRT
<213> ORGANISM: Artificial Sequence
<220> FEATURE:
<223> OTHER INFORMATION: mutated Chop2

<400> SEQUENCE: 25

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Cys Ile His Leu Ser Asn Leu Thr Gly Leu Ser Asn Asp
```

```
                130                 135                 140
Tyr Ser Arg Arg Thr Met Gly Leu Leu Val Ser Asp Ile Gly Ala Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val Asn Lys Gly Thr Gly Lys
305                 310                 315

<210> SEQ ID NO 26
<211> LENGTH: 315
<212> TYPE: PRT
<213> ORGANISM: Artificial Sequence
<220> FEATURE:
<223> OTHER INFORMATION: ChR2 mutant construct

<400> SEQUENCE: 26

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
```

-continued

```
                180                 185                 190
Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
        290                 295                 300

Glu Ala Gly Ala Val Asn Lys Gly Thr Gly Lys
305                 310                 315
```

IDENTIFICATION OF CHANNELRHODOPSIN-2 (CHR2) MUTATIONS AND METHODS OF USE

RELATED APPLICATIONS

This application is a national stage application, filed under 35 U.S.C § 371, of PCT/US2013/029171, filed on Mar. 5, 2013, which claims the benefit of U.S. Provisional Application No. 61/606,663 filed Mar. 5, 2012, the contents of each of which are incorporated by reference herein in their entireties.

GOVERNMENT SUPPORT

This invention was made with government support under EY017130 awarded by the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: RTRO_703N01US_Seq.txt, date recorded: Aug. 29, 2014, file size 98.2 kilobytes).

FIELD OF THE INVENTION

This invention relates generally to the field of molecular biology. Mutations in the Channelopsin-2 (Chop2) gene are identified. Compositions comprising a mutant Chop2 gene are used in therapeutic methods to improve and restore vision loss.

BACKGROUND OF THE INVENTION

The retina is composed of photoreceptors (or photoreceptor cells, rods and cones). Photoreceptors are highly specialized neurons that are responsible for phototransduction, or the conversion of light (in the form of electromagnetic radiation) into electrical and chemical signals that propagate a cascade of events within the visual system, ultimately generating a representation of our world.

Photoreceptor loss or degeneration severely compromises, if not completely inhibits, phototransduction of visual information within the retina. Loss of photoreceptor cells and/or loss of a photoreceptor cell function are the primary causes of diminished visual acuity, diminished light sensitivity, and blindness. There is a long-felt need in the art for compositions and method that restore photosensitivity of the retina of a subject experiencing vision loss.

SUMMARY OF THE INVENTION

The invention provides a solution for the long-felt need for a method of restoring and/or increasing the light sensitivity of photoreceptor cells by expression of advantageous mutations, and/or combinations thereof, of the Channelopsin-2 (Chop2) gene, and subsequently providing methods for Channelopsin-2 (Chop2)-based gene therapy.

Channelopsin-2 (Chop2)-based gene therapy offers a superior strategy for restoring retinal photosensitivity after photoreceptor degeneration. The protein product of the Chop2 gene, when bound to the light-isomerizable chromophore all-trans-retinal, forms a functional light-gated channel, called channelrhodopsin-2 (ChR2). Native ChR2 shows low light sensitivity. Recently, two mutant ChR2s, L132C and T159C, were reported to markedly increase their light sensitivity (Kleinlogel et al. (2011) Nat. Neurosci. 14:513-8; Berndt et al. (2011) Proc Natl Acad Sci USA. 108:7595-600; Prigge et al. (2012) J Biol. Chem. 287(38) 3104:12; the contents of each of which are incorporated herein in their entireties). The properties of these two ChR2 mutants (i.e., L132C and T159C) were examined and compared with a number of double mutants at these two sites to identify suitable candidates for therapeutic methods. Compositions comprising one or more of these mutations are provided to a subject in need thereof for the purpose of restoring vision. Specifically, desired mutations in the Chop2 gene are introduced to a cell and/or integrated into the genomic DNA of a cell to improve or restore vision. Desired mutations in the Chop2 gene that are introduced to a cell to improve or restore vision may also remain episomal, not having integrated into the genomic DNA.

Mutations at the L132 or T159 amino acid positions of Chop2 (and therefore, the resulting ChR2) markedly lower the threshold light intensity that is required to elicit the ChR2-mediated photocurrent. Double mutants at the amino acid positions L132 and T159 further increase the photocurrent at low light intensities, exceeding that of either of the corresponding single mutations. Retinal ganglion cells expressing the double mutants at the L132 and T159 positions can respond to light intensities that fall within the range of normal outdoor lighting conditions but should still maintain adequate, and high temporal resolution that are suitable for restoring useful vision. Thus, mutant Chop2 protein of the present invention that form mutant ChR2s having improved light sensitivity are used alone or in combination to restore or improve vision.

Specifically, the invention provides an isolated polypeptide molecule comprising or consisting of SEQ ID NO: 26 in which the amino acid at position 132 of SEQ ID NO: 26 is not leucine (L). In certain embodiments of the isolated polypeptide molecule, the amino acid at position 132 is cysteine (C) or alanine (A). When the amino acid at position 132 is cysteine (C), the polypeptide molecule may comprise or consist of SEQ ID NO: 13. When the amino acid at position 132 is alanine (A), the polypeptide molecule may comprise or consist of SEQ ID NO: 20.

The invention provides an isolated polypeptide molecule comprising or consisting of SEQ ID NO: 26 in which the amino acid at position 159 of SEQ ID NO: 26 is not a threonine (T). In certain embodiments of the isolated polypeptide molecule, the amino acid at position 159 is cysteine (C), serine (S), or alanine (A). When the amino acid at position 159 is cysteine (C), the polypeptide molecule may comprise or consist of SEQ ID NO: 14. When the amino acid at position 159 is serine (S), the polypeptide molecule may comprise or consist of SEQ ID NO: 17. When the amino acid at position 159 is alanine (A), the polypeptide molecule may comprise or consist of SEQ ID NO: 23.

The invention provides isolated polypeptide molecule comprising or consisting of SEQ ID NO: 26 in which the amino acid at position 132 of SEQ ID NO: 26 is not leucine (L) and the amino acid at position 159 is not threonine (T). In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is cysteine (C), and the amino acid at position 159 is cysteine (C). In a preferred embodiment of this isolated polypeptide molecule, the polypeptide molecule comprises or consists of SEQ ID NO: 16. The invention provides an isolated nucleic acid molecule that encodes for the isolated polypeptide comprising or consisting of SEQ ID NO: 16. Preferably, the isolated nucleic acid molecule that encodes for the isolated polypeptide comprising or consisting of SEQ ID NO: 16, is a nucleic acid molecule that comprises or consists of SEQ ID NO: 15.

In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is cysteine (C) and the amino acid at position 159 is serine(S). The isolated polypeptide molecule comprising or consisting of SEQ ID NO: 26 in which the amino acid at position 132 of SEQ ID NO: 26 is not leucine (L) and the amino acid at position 159 is not threonine (T), may comprise or consist of SEQ ID NO: 19. Alternatively, or in addition, the isolated polypeptide molecule comprising or consisting of SEQ ID NO: 26 in which the amino acid at position 132 of SEQ ID NO: 26 is not leucine (L) and the amino acid at position 159 is not threonine (T), wherein the amino acid at position 132 is cysteine (C) and wherein the amino acid at position 159 is serine(S) may comprise or consist of SEQ ID NO: 19. The invention provides an isolated nucleic acid molecule that encodes for the isolated polypeptide that comprises or consists of SEQ ID NO: 19. Preferably, the nucleic acid molecule comprises or consists of SEQ ID NO: 18.

In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is alanine (A) and the amino acid at position 159 is cysteine (C). The isolated polypeptide molecule comprising or consisting of SEQ ID NO: 26 in which the amino acid at position 132 of SEQ ID NO: 26 is not leucine (L) and the amino acid at position 159 is not threonine (T) may comprise or consist of SEQ ID NO: 22. Alternatively, or in addition, the isolated polypeptide molecule comprising or consisting of SEQ ID NO: 26 in which the amino acid at position 132 of SEQ ID NO: 26 is not leucine (L) and the amino acid at position 159 is not threonine (T), wherein the amino acid at position 132 is alanine (A) and wherein the amino acid at position 159 is cysteine (C) may comprise or consist of SEQ ID NO: 22. The invention provides an isolated nucleic acid molecule that encodes for the isolated polypeptide that comprises or consists of SEQ ID NO: 22. Preferably, this nucleic acid molecule comprises or consists of SEQ ID NO: 21.

In certain embodiments of the isolated polypeptide molecule comprising or consisting of SEQ ID NO: 26 in which the amino acid at position 132 of SEQ ID NO: 26 is not leucine (L) and the amino acid at position 159 is not threonine (T), the amino acid at position 132 is cysteine (C) and the amino acid at position 159 is alanine (A). The isolated polypeptide molecule comprising or consisting of SEQ ID NO: 26 in which the amino acid at position 132 of SEQ ID NO: 26 is not leucine (L) and the amino acid at position 159 is not threonine (T) may comprise or consist of SEQ ID NO: 25. Alternatively, or in addition, the isolated polypeptide molecule comprising or consisting of SEQ ID NO: 26 in which the amino acid at position 132 of SEQ ID NO: 26 is not leucine (L) and the amino acid at position 159 is not threonine (T), wherein the amino acid at position 132 is cysteine (C) and wherein the amino acid at position 159 is alanine (A) may comprise or consist of SEQ ID NO: 25. The invention provides an isolated nucleic acid molecule that encodes for the isolated polypeptide that comprises or consists of SEQ ID NO: 25. Preferably, this nucleic acid molecule comprises or consists of SEQ ID NO: 24.

The invention provides any one of the isolated polypeptide molecules described herein, wherein the polypeptide molecule encodes for a mutant Chop2 protein that forms a mutant ChR2, which elicits a current in response to a threshold intensity of light that is lower than the threshold of a wild type ChR2 protein. Moreover, the current conducts cations. Exemplary cations include, but are not limited to, $H^+$, $Na^+$, $K^+$, and $Ca^{2+}$ ions. The ChR2 wild type and mutant proteins described herein non-specifically conduct cations. Consequently, the current conducts one or more of the following: $H^+$, $Na^+$, $K^+$, and $Ca^{2+}$ ions.

The invention provides any one of the isolated polypeptide molecules described herein further comprising a pharmaceutically acceptable carrier. The invention also provides a composition comprising at least one isolated polynucleotide molecule described herein. The composition may further comprise a pharmaceutically-acceptable carrier.

The invention provides an isolated nucleic acid molecule that encodes for any of the isolated polypeptides described herein. Moreover, the isolated nucleic acid molecule may further include a pharmaceutically acceptable carrier. The invention also provides a composition comprising at least one isolated nucleic acid molecule described herein. The composition may further comprise a pharmaceutically-acceptable carrier.

The invention provides a cell, wherein the cell has been contacted with or comprises an isolated polypeptide molecule of the invention. Moreover, the invention provides a cell, wherein the cell has been contacted with or comprises an isolated nucleic acid molecule that encodes for an isolated polypeptide molecule of the invention. The invention provides, a composition comprising, consisting essentially of, or consisting of a cell that comprises an isolated polypeptide molecule of the invention or a nucleic acid molecule that encodes for an isolated polypeptide molecule of the invention. Cells of the invention may be contacted with the isolated polypeptide or an isolated nucleic acid encoding the polypeptide in vitro, ex vivo, in vivo, or in situ. In certain embodiments of the invention, the cell is a photoreceptor; a horizontal cell; a bipolar cell; an amacrine cell, and, especially, an AII amacrine cell; or a retinal ganglion cell, including a photosensitive retinal ganglion cell. Preferably, the cell is a retinal ganglion cell, a photosensitive retinal ganglion cell, a bipolar cell, an ON-type bipolar cell, a rod bipolar cell, or an AII amacrine cell. In certain aspects of the invention, the cell is a photoreceptor, a bipolar cell, a rod bipolar cell, an ON-type cone bipolar cell, a retinal ganglion cell, a photosensitive retinal ganglion cell, a horizontal cell, an amacrine cell, or an AII amacrine cell.

The invention provides a method of improving or restoring vision, comprising administering to a subject any one of the compositions described herein. The invention further provides a prophylactic method of preserving vision, comprising administering to a subject any one of the compositions described herein.

The methods described herein may also be applied to those subjects who are healthy, blind (in part or in total), and/or those subjects with retinal degeneration (characterized by a loss of rod and/or cone photoreceptor cells), but may be dependent upon the activity of photosensitive retinal ganglion cells for a determination of ambient light levels. For example, the methods described herein can be used to preserve, improve, or restore the activity of a photosensitive retinal ganglion cell that mediates the transduction of light information for synchronizing circadian rhythms to the 24-hour light/dark cycle, pupillary control and reflexes, and photic regulation of melatonin release.

In certain embodiments of the methods of the invention, the subject may have normal vision or impaired vision. Alternatively, or in addition, the subject may be at risk for developing an ocular disease that leads to impairment of vision. For example, the subject may have a family history of, ocular disease, including, macular degeneration and retinitis pigmentosa. The subject may be at risk for incurring an eye injury that causes damage to photosensitive cells in the retina. The subject may have a genetic marker or genetic/congenital condition that results in impaired vision, low vision, legal blindness, partial blindness, or complete blindness. Subjects may have a refractive defect that results in myopia (near-sightedness) or hyperopia (far-sightedness).

Compositions of methods of the invention may be administered to a subject either systemically or locally. A preferred route of local administration is intravitreal injection.

Other features and advantages of the invention will be apparent from and are encompassed by the following detailed description and claims.

DETAILED DESCRIPTION

Visual System

Figure 1:
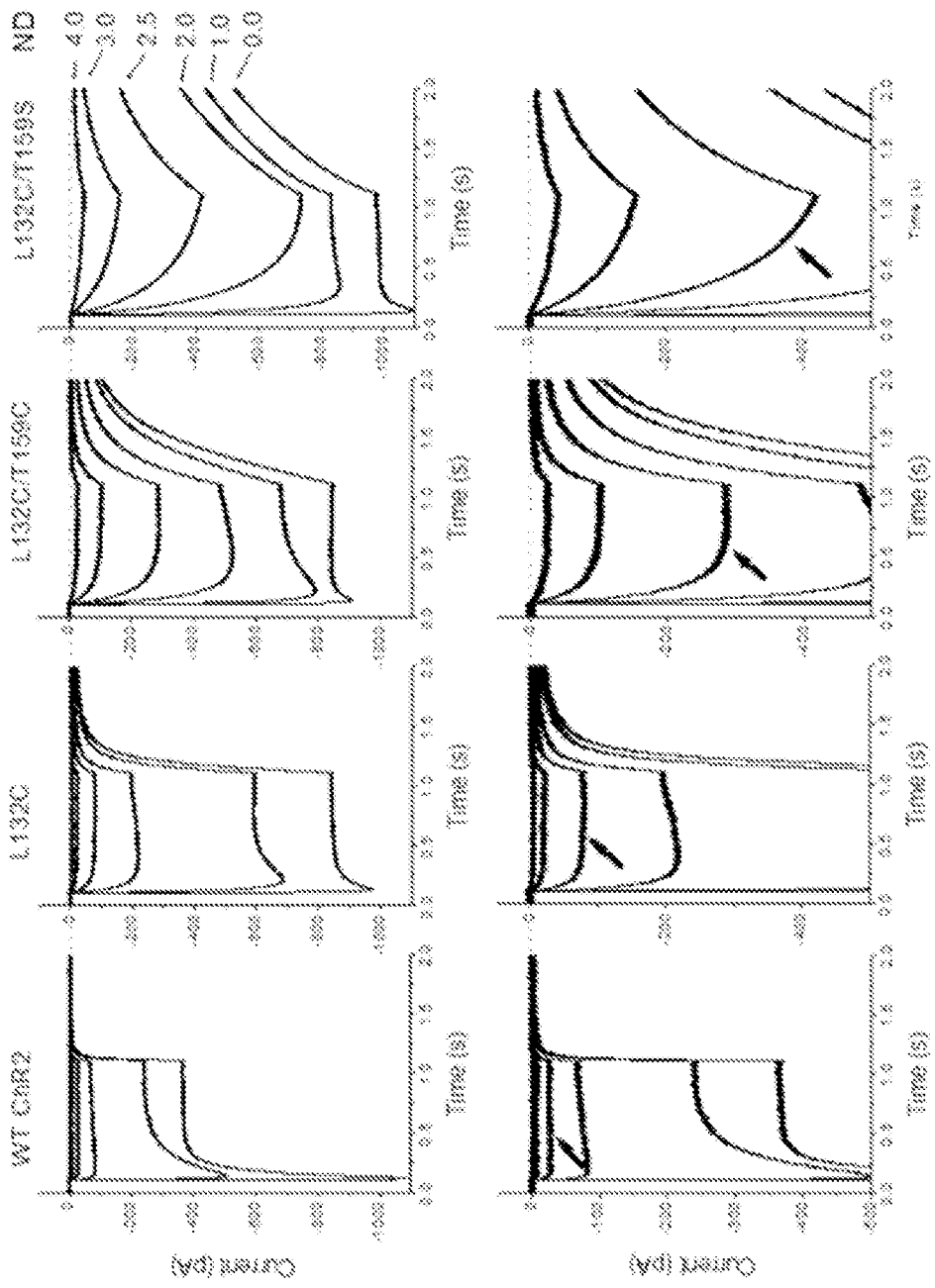
FIG. 1 shows representative recordings of the light-evoked currents from wild-type (WT) ChR2, L132C, L132C/T159C, and L132C/159S mutants in HEK cells for comparison of their light sensitivity (A). The light stimuli (photons/cm$^2$.s at 460 nm) were generated by a xenon arc lamp and attenuated by neutral density filters: ND4.0 ($2.8 \times 10^{14}$), ND3.0 ($1.4 \times 10^{15}$), ND2.5 ($4.8 \times 10^{15}$); ND2.0 ($1.6 \times 10^{16}$), ND1.0 ($1.3 \times 10^{17}$), ND0 ($1.2 \times 10^{18}$). (B) The same current traces are shown at a different current scale. The traces pointed by arrows are evoked by the same light intensity (ND2.5).

The central nervous system mediates vision (also referred to herein as sight) through specialized cells and unique methods of signal transduction present in the visual system. The principle responsibility of the visual system is to transform light, in the form of electromagnetic radiation, into a representation or image of the surrounding world. In addition to the "visual" function of this system, the visual system also regulates the pupillary light reflex (PLR), circadian photoentrainment to periodic light/dark cycles, and release of the hormone melatonin.

The cells of the retina are the first cells of the visual or nervous system to encounter light (electromagnetic radiation of varying wavelengths and intensities). Photons travel through the cornea, pupil, and lens before reaching the retina. The retina has a unique structure because the photoreceptor cells that directly absorb photons are located in the outer layer of the retina. Photons that traverse the lens first encounter an inner layer of retinal ganglion cells (a minority of which are photosensitive through the expression of the opsin, melanopsin) and an intermediate layer of bipolar cells before reaching the outer layer of photoreceptor cells (also known as rods and cones). Rod photoreceptors operate in dim illumination condition (scotopic vision) while cone photoreceptors operate in bright illumination conditions (photopic vision) responsible for color vision. Cone photoreceptors synapse directly onto ON- and OFF-type cone bipolar cells, which in turn, synapse directly onto ON- and OFF-type retinal ganglion cells. Rod photoreceptors synapse to rod bipolar cells (a unique type of bipolar cells, which is ON-type), which synapse to AII amacrine cells. The AII amacrine cells then relay the visual signals to ON-type cone bipolar cells through gap junction and to OFF-type cone bipolar cells as well as OFF ganglion cells through inhibitory glycinergic synapses. Retinal ganglion cells are responsible for relating visual information to neurons of the brain.

Phototransduction

Within the retina, photoreceptor cells absorb photon particles and transform the raw data of light frequency and wavelength into chemical and subsequently electrical signals that propagate this initial information throughout the visual and nervous systems. Specifically, an opsin protein located on the surface of a photoreceptor (rod, cone, and/or photosensitive retinal ganglion cell) absorbs a photon and initiates an intracellular signaling cascade, which results in the hyperpolarization of the photoreceptor. In the dark, the opsin proteins absorb no photons, the photoreceptors are depolarized. The visual signals of photoreceptors then relay through bipolar cells, amacrine cells, and ganglion cells to the high visual centers in the brain. Specifically, when rod and cone photoreceptors are depolarized (in the dark), they cause the depolarization of rod bipolar cells and ON-type cone bipolar cells, but the hyperpolarization of OFF-type cone bipolar cells, which in turn cause the depolarization of AII amacrine cells and the increase of the spiking of ON-type retinal ganglion cells and the decrease of the spiking of OFF-type retinal ganglion cells. The opposite happens (to rod, ON- and OFF-bipolar cells, AII amacrine and ON- and OFF-ganglion cells), when rod and cone photoreceptors are hyperpolarized (in response to light).

Light information is processed and refined significantly by the actions of photoreceptors, bipolar cells, horizontal cells, amacrine cells, and retinal ganglion cells. To add to the complexity of this system, photoreceptors are found in three main varieties, including rods, cones (of which three types respond most strongly to distinct wavelengths of light), and photosensitive retinal ganglion cells. Thus, a first layer of information processing occurs at the level of the photoreceptors which respond differentially to certain wavelengths and intensities of light. Bipolar cells of the retina receive information from both photoreceptor cells and horizontal cells. Horizontal cells of the retina receive information from multiple photoreceptor cells, and, therefore, integrate information between cell types and across distances in the retina. Bipolar cells further integrate information directly from photoreceptor cells and horizontal cells by producing mainly graded potentials to retinal ganglion cells, although some recent studies indicate that some bipolar cells can generate action potentials. Cone bipolar cells synapse on retinal ganglion cells and amacrine cells while rod bipolar cells synapse only to AII amacrine cells. Similar to horizontal cells, most amacrine cells integrate information laterally within the retina. Unlike horizontal cells, most amacrine cells are inhibitory (GABAergic) interneurons. Amacrine cells are also more specialized than horizontal cells, because each amacrine cell specifically synapses on a particular type of bipolar cell (one of the ten varieties of bipolar cell). Particularly, the AII amacrine cell is a critical relay neuron in the rod pathway (under scotopic vision when cone photoreceptors do not respond). The AII amacinre cells receive synaptic inputs from rod bipolar cells and then piggy-back the signals to cone pathway through ON- and OFF-cone bipolar cells to ON- and OFF-ganglion cells as described above. Therefore, expression of Chop2, and the resulting formation of ChR2, in rod bipolar cells or AII amacrine cells can create both ON and OFF responses in retinal ganglion cells. Furthermore, retinal ganglion cells integrate information from bipolar cells and from amacrine cells. Although retinal ganglion cells vary significantly with respect to size, connectivity, and responses to visual stimulation (e.g. visual fields), all retinal ganglion cells extend a long axon into the brain. Except for a minute portion of the retinal ganglion cells that transduce non-visual information regarding the pupillary light reflex and circadian entrainment, the totality of axons extending from the retinal ganglion cells form the optic nerve, optic chiasm, and optic tract of the central nervous system. Consequently, a significant amount of information processing occurs in the retina itself.

Photoreceptor cells express endogenous opsin proteins, such as rhodopsin. The mutant Chop2 proteins of the invention may be expressed in any cell type, and form functional ChR2 channels. Preferably, the cell is a retinal cell. Exemplary cells, include, but are not limited to, photoreceptor cells (e.g., rods, cones, and photosensitive retinal ganglion cells), horizontal cells, bipolar cells, amacrine cells, and retinal ganglion cells.

Channelopsin-2 (Chop2)

Channelopsin-2 (Chop2) was first isolated from the green algae, *Chlamydomonas reinhardtii*. Channelopsin-2 is a seven transmembrane domain protein that becomes photoswitchable (light sensitive) when bound to the chromophore all-trans-retinal. Chop2, when linked to a retinal molecule via Schiff base linkage forms a light-gated, nonspecific, inwardly rectifying, cation channel, called Channelrhodopsin-2 (Chop2 retinalidene, abbreviated ChR2).

As referred to herein, "channelopsin-2" or "Chop2" refers to the gene that encodes channelopsin-2, which then forms Channelrhodopsin-2 (ChR2) once bound to retinal. Gene constructs of the present invention refer primarily to channelopsin-2 (i.e., without the retinal), and all Chop2 variants disclosed herein form functional channelrhodopsin-2 variants. The methods disclosed herein may include delivering Chop2 to cells without exogenous retinal. It is understood that upon expression of Chop2 in cells (i.e., retinal neurons), endogenously available retinal binds to the wild-type Chop2 or the Chop2 mutants of the present invention to form functional light-gated channels, WT ChR2 or mutant ChR2. As such, Chop2 proteins, as referred to herein, can also be synonymous with ChR2.

As used herein, "channelrhodopsin-2" or "ChR2" refers to the retinal-bound functional light-sensitive channel. In one embodiment, the bound retinal may be provided exogenously. In a preferred embodiment, the bound retinal is provided from endogenous levels available in the cell. The present invention also encompasses the functional channelrhodopsin-2 channels formed by the polypeptides and polynucleotides encoding the Chop2 mutants described herein.

Upon illumination by the preferred dose of light radiation, ChR2 opens the pore of the channel, through which $H^+$, $Na^+$, $K^+$, and/or $Ca^{2+}$ ions flow into the cell from the extracellular space. Activation of the ChR2 channel typically causes a depolarization of the cell expressing the channel. Depolarized cells produce graded potentials and or action potentials to carry information from the Chop2/ChR2-expressing cell to other cells of the retina or brain.

The wild type form of ChR2 or mutant ChR2s with high temporal resolution have become a central focus of neuroscience research. When expressed in a mammalian neuron, ChR2 mediates light-controlled depolarization of in vitro or ex vivo cultures. Wild type ChR2s or mutant ChR2s with high temporal resolution (the latter usually display low light sensitivity) presents several challenges that must be addressed to enable their use for the purpose of vision restoration. For the purpose of vision restoration, the ChR2 with high light sensitivity rather than high temporal resolution is desired.

Wild type ChR2 proteins require illumination from high blue light intensities for full activation (i.e. $10^{18}$-$10^{19}$ photons $s^{-1}$ $cm^{-2}$ at a wavelength of 480 nm). Continuous illumination of this type can damage cells.

The kinetics of the wild type ChR2 protein is suboptimal for maximizing channel efficacy. Efficacy can be increased by modifying one or more amino acids of the wild type ChR2 protein either to prolong the open state of the channel or increase the unit conductance of the channel, or both. The single-channel conductance of wild-type ChR2 is small. Thus, neuronal activation in vivo would either require high expression of the wild type channel or very intense activation with the preferred wavelength of blue-light. A simpler solution may be found by altering the channel conductance or to prolong the channel open time. Either one of these mechanisms and, in particular, the combination of these mechanisms, enable lower and safer light intensities to be used to achieve the same level of cellular depolarization.

For example, mutant ChR2 proteins of the invention achieve greater light sensitivity through the prolongation of the channel open state. Consequently, each mutant ChR2 channel conducts a greater photocurrent than a wild type ChR2 channel when activated by the same light intensities. Therefore, the mutant channels are activated by light intensities that are lower than those required for activation of the wild type ChR2 channels. Quantitatively, detectable spiking activity of retinal ganglion cells expressing mutant ChR2 proteins can be elicited by a light intensity that is 1.5-2 log units lower than the light intensity required to elicit spiking activity from retinal ganglion cells expressing wild type ChR2. Thus, the light intensities required to activate the mutant ChR2 proteins are close to or fall within the range of normal outdoor lighting conditions.

The following sequences provide non-limiting examples of wild type and mutant Chop2 proteins, and polynucleotides encoding said WT and mutant Chop2 proteins of the invention, and forming WT and mutant ChR2s of the invention.

A wild type (WT) Chop2 of the invention may be encoded by the following *Chlamydomonas reinhardtii* chlamyopsin 4 light-gated ion channel (COP4) mRNA sequence (GenBank Accession No. XM_001701673, and SEQ ID NO: 1):

```
   1 gcagcaccat acttgacatc tgtcgccaag caagcattaa acatggatta tggaggcgcc
  61 ctgagtgccg ttgggcgcga gctgctattt gtaacgaacc cagtagtcgt caatggctct
 121 gtacttgtgc ctgaggacca gtgttactgc gcgggctgga ttgagtcgcg tggcacaaac
 181 ggtgcccaaa cggcgtcgaa cgtgctgcaa tggcttgctg ctggcttctc catcctactg
 241 cttatgtttt acgcctacca aacatggaag tcaacctgcg gctgggagga gatctatgtg
 301 tgcgctatcg agatggtcaa ggtgattctc gagttcttct tcgagtttaa gaacccgtcc
 361 atgctgtatc tagccacagg ccaccgcgtc cagtggttgc gttacgccga gtggcttctc
 421 acctgcccgg tcattctcat tcacctgtca aacctgacgg gcttgtccaa cgactacagc
 481 aggcgcacca tgggtctgct tgtgtctgat attggcacaa ttgtgtgggg cgccacttcc
 541 gccatggcca ccggatacgt caaggtcatc ttcttctgcc tgggtctgtg ttatggtgct
 601 aacacgttct ttcacgctgc caaggcctac atcgagggtt accacaccgt gccgaagggc
 661 cggtgtcgcc aggtggtgac tggcatggct tggctcttct tcgtatcatg gggtatgttc
 721 cccatcctgt tcatcctcgg ccccgagggc ttcggcgtcc tgagcgtgta cggctccacc
 781 gtcggccaca ccatcattga cctgatgtcg aagaactgct ggggtctgct cggccactac
 841 ctgcgcgtgc tgatccacga gcatatcctc atccacggcg acattcgcaa gaccaccaaa
 901 ttgaacattg gtggcactga gattgaggtc gagacgctgg tggaggacga ggccgaggct
 961 ggcgcggtca acaagggcac cggcaagtac gcctcccgcg agtccttcct ggtcatgcgc
1021 gacaagatga aggagaaggg cattgacgtg cgcgcctctc tggacaacag caaggaggtg
1081 gagcaggagc aggccgccag ggctgccatg atgatgatga acggcaatgg catgggtatg
1141 ggaatgggaa tgaacggcat gaacggaatg ggcggtatga acgggatggc tggcggcgcc
1201 aagcccggcc tggagctcac tccgcagcta cagcccggcc gcgtcatcct ggcggtgccg
1261 gacatcagca tggttgactt cttccgcgag cagtttgctc agctatcggt gacgtacgag
1321 ctggtgccgg ccctgggcgc tgacaacaca ctggcgctgg ttacgcaggc gcagaacctg
1381 ggcggcgtgg actttgtgtt gattcacccc gagttcctgc gcgaccgctc tagcaccagc
1441 atcctgagcc gcctgcgcgg cgcgggccag cgtgtggctg cgttcggctg ggcgcagctg
1501 gggcccatgc gtgacctgat cgagtccgca aacctggacg ctggctgga gggcccctcg
1561 ttcggacagg gcatcctgcc ggcccacatc gttgccctgg tggccaagat gcagcagatg
1621 cgcaagatgc agcagatgca gcagattggc atgatgaccg gcggcatgaa cggcatgggc
1681 ggcggtatgg gcggcggcat gaacggcatg gcggcggca acggcatgaa caacatgggc
1741 aacggcatgg gcggcggcat gggcaacggc atgggcggca atggcatgaa cggaatgggt
1801 ggcggcaacg gcatgaacaa catgggcggc aacggaatgg ccggcaacgg aatgggcggc
1861 ggcatgggcg gcaacggtat gggtggctcc atgaacggca tgagctccgg cgtggtggcc
1921 aacgtgacgc cctccgccgc cggcggcatg gcggcatga tgaacggcgg catggctgcg
1981 ccccagtcgc ccggcatgaa cggcggccgc ctgggtacca cccgctctt caacgccgcg
2041 ccctcaccgc tcagctcgca gctcggtgcc gaggcaggca tgggcagcat gggaggcatg
2101 ggcggaatga gcggaatggg aggcatgggt ggaatggggg gcatgggcgg cgccggcgcc
2161 gccacgacgc aggctgcggg cggcaacgcg gaggcggaga tgctgcagaa tctcatgaac
```

-continued

```
2221 gagatcaatc gcctgaagcg cgagcttggc gagtaaaagg ctggaggccg gtactgcgat 2281 acctgcgagc tcgcgcgcct gactcgtcgt acacacggct caggagcacg cgcgcgtgga 2341 cttctcaacc tgtgtgcaac gtatctagag cggcctgtgc gcgaccgtcc gtgagcattc 2401 cggtgcgatc ttcccgcctt cgcaccgcaa gttcccttcc tggccctgct gcgcctgacg 2461 catcgtccga acggaagggc ggcttgatca gtaaagcatt gaagactgaa gtcgtgcgac 2521 cgtagtgcta tggctctgca cgtaagtggg cgctgccctg cttactacgc attgcccaag 2581 actgcttcct tttggtggcc gaggccctgg tcccacatca ttcatttgca taacgtactg 2641 tttagttaca tacgctttgc ttaacctcga caattgcaac atgggctgag agtccgtacg 2701 gcggctatgg acgaaggtgt tatcggatgt gattaggaat ctcggttgaa aggcttcgag 2761 aaagtgagct tcatctgtgg cttctgttgg ggtcatcaag aagaacgacg gtaaggcaaa 2821 cgaggtaaaa gtggcacgtc tttgtgcaca acgggcccgt ggagagtggg ggagtgcatg 2881 tgtgcggtcc taacacgcga gtgcaaagcg ggcttttctg gagctgggtt acggtctggc 2941 tcggcaactg ctctgtgttt taaccacagc ttcggaagtc tgggtatgtt ttgttggcag 3001 aaacatttgg gtaacttgag ggtgattcgt ctggagtcgg acaacatggc tgccgtccgt 3061 gtgcagggac ggtaatcaat gagctggagc tgtgatgctc accacacgtt gcatacccct 3121 gcttacaaaa acactttgat gtcgtggcca aactatgcgt gagcaaagag ttaaagaggc 3181 atgagtgcat ggttgcggac gtgcgcaaca attgcatcaa gtatttgacg ccttcaagcc 3241 aacaagtgcg cgcgcggcaa cttgattaac acgccggacg cagtggtggg ggcgtgtaca 3301 gtgtttatga gctgccattc tgcgatccgt agtgttaggt tgcgtgtgac gccgcgcggc 3361 tgtgggccct tacatggaga gttgggtgct tcaccacacg gttggcgccg ctgaagggtg 3421 tgctatgttt tggtaaagcc ggggccctga agaccgcaac cgtagaaccg tactgaaagg 3481 gtgtcagccc ggggtaactg gatgccctgg gacatagcta ttaatgttga agtgaagccg 3541 tcaagccgag tgccgtgcgc cgctgtatca ccaaggcccg tccta
```

A wild type (WT) ChR2 of the invention may be encoded by the following *Chlamydomonas reinhardtii* chlamyopsin 4 light-gated ion channel (COP4) amino acid sequence (GenBank Accession No. XP_001701725, and SEQ ID NO: 2):

```
  1 mdyggalsav grellfvtnp vvvngsvlvp edqcycagwi esrgtngaqt asnvlqwlaa 61 gfsilllmfy ayqtwkstcg weeiyvcaie mvkvilefff efknpsmlyl atghrvqwlr 121 yaewlltcpv ilihlsnltg lsndysrrtm gllvsdigti vwgatsamat gyvkviffcl 181 glcygantff haakayiegy htvpkgrcrq vvtgmawlff vswgmfpilf ilgpegfgvl 241 svygstvght iidlmskncw gllghylrvl ihehililhgd irkttklnig gteievetlv 301 edeaeagavn kgtgkyasre sflvmrdkmk ekgidvrasl dnskeveqeq aaraammmmn 361 gngmgmgmgm ngmngmggmn gmaggakpgl eltpqlqpgr vilavpdism vdffreqfaq 421 lsvtyelvpa lgadntlalv tqaqnlggvd fvlihpeflr drsstsilsr lrgagqrvaa 481 fgwaqlgpmr dliesanldg wlegpsfgqg ilpahivalv akmqqmrkmq qmqqigmmtg 541 gmngmgggmg ggmngmgggn gmnnmgngmg ggmgngmggn gmngmgggng mnnmggngma 601 gngmgggmgg ngmggsmngm ssgvvanvtp saaggmggmm nggmaapqsp gmnggrlgtn 661 plfnaapspl ssqlgaeagm gsmggmggms gmggmggmgg mggagaattq aaggnaeaem 721 lqnlmneinr lkrelge
```

A wild type (WT) Chop2 of the invention may be encoded by the following *Chlamydomonas reinhardtii* retinal binding protein (cop4) gene sequence (GenBank Accession No. AF461397, and SEQ ID NO: 3):

```
   1 gcatctgtcg ccaagcaagc attaaacatg gattatggag gcgccctgag tgccgttggg
  61 cgcgagctgc tatttgtaac gaacccagta gtcgtcaatg gctctgtact tgtgcctgag
 121 gaccagtgtt actgcgcggg ctggattgag tcgcgtggca caaacggtgc ccaaacggcg
 181 tcgaacgtgc tgcaatggct tgctgctggc ttctccatcc tactgcttat gttttacgcc
 241 taccaaacat ggaagtcaac ctgcggctgg gaggagatct atgtgtgcgc tatcgagatg
 301 gtcaaggtga ttctcgagtt cttcttcgag tttaagaacc cgtccatgct gtatctagcc
 361 acaggccacc gcgtccagtg gttgcgttac gccgagtggc ttctcacctg cccggtcatt
 421 ctcattcacc tgtcaaacct gacgggcttg tccaacgact acagcaggcg caccatgggt
 481 ctgcttgtgt ctgatattgg cacaattgtg tggggcgcca cttccgccat ggccaccgga
 541 tacgtcaagg tcatcttctt ctgcctgggt ctgtgttatg gtgctaacac gttctttcac
 601 gctgccaagg cctacatcga gggttaccac accgtgccga agggccggtg tcgccaggtg
 661 gtgactggca tggcttggct cttcttcgta tcatggggta tgttccccat cctgttcatc
 721 ctcggccccg agggcttcgg cgtcctgagc gtgtacggct ccaccgtcgg ccacaccatc
 781 attgacctga tgtcgaagaa ctgctggggt ctgctcggcc actacctgcg cgtgctgatc
 841 cacgagcata tcctcatcca cggcgacatt cgcaagacca ccaaattgaa cattggtggc
 901 actgagattg aggtcgagac gctggtggag gacgaggccg aggctggcgc ggtcaacaag
 961 ggcaccggca gtacgcctc ccgcgagtcc ttcctggtca tgcgcgacaa gatgaaggag
1021 aagggcattg acgtgcgcgc ctctctggac aacagcaagg aggtggagca ggagcaggcc
1081 gccaggctg ccatgatgat gatgaacggc aatggcatgg gtatgggaat gggaatgaac
1141 ggcatgaacg gaatgggcgg tatgaacggg atggctggcg gcgccaagcc cggcctggag
1201 ctcactccgc agctacagcc cggccgcgtc atcctggcgg tgccggacat cagcatggtt
1261 gacttcttcc gcgagcagtt tgctcagcta tcggtgacgt acgagctggt gccggccctg
1321 ggcgctgaca acacactggc gctggttacg caggcgcaga acctgggcgg cgtggacttt
1381 gtgttgattc accccgagtt cctgcgcgac cgctctagca ccagcatcct gagccgcctg
1441 cgcggcgcgg gccagcgtgt ggctgcgttc ggctgggcgc agctggggcc catgcgtgac
1501 ctgatcgagt ccgcaaacct ggacggctgg ctggagggcc cctcgttcgg acagggcatc
1561 ctgccggccc acatcgttgc cctggtggcc aagatgcagc agatgcgcaa gatgcagcag
1621 atgcagcaga ttggcatgat gaccggcggc atgaacggca tgggcggcgg tatgggcggc
1681 ggcatgaacg gcatgggcgg cggcaacggc atgaacaaca tgggcaacgg catgggcggc
1741 ggcatgggca acgcatggg cggcaatggc atgaacggaa tgggtggcgg caacggcatg
1801 aacaacatgg gcggcaacgg aatggccggc aacggaatgg gcggcggcat gggcggcaac
1861 ggtatgggtg gctccatgaa cggcatgagc tccggcgtgg tggccaacgt gacgccctcc
1921 gccgccggcg gcatgggcgg catgatgaac ggcggcatgg ctgcgcccca gtcgcccggc
1981 atgaacggcg gccgcctggg taccaacccg ctcttcaacg ccgcgccctc accgctcagc
2041 tcgcagctcg gtgccgaggc aggcatgggc agcatgggag gcatgggcgg aatgagcgga
2101 atgggaggca tgggtggaat gggggggcatg ggcggcgccg gcgccgccac gacgcaggct
2161 gcgggcggca acgcggaggc ggagatgctg cagaatctca tgaacgagat caatcgcctg
2221 aagcgcgagc ttggcgagta a
```

A wild type (WT) Chop2 of the invention may be encoded by the following *Chlamydomonas reinhardtii* retinal binding protein (cop4) amino acid sequence (GenBank Accession No. AAM15777, and SEQ ID NO: 4):

```
  1 mdyggalsav grellfvtnp vvvngsvlvp edqcycagwi esrgtngaqt asnvlqwlaa
 61 gfsilllmfy ayqtwkstcg weeiyvcaie mvkvilefff efknpsmlyl atghrvqwlr
121 yaewlltcpv ilihlsnltg lsndysrrtm gllvsdigti vwgatsamat gyvkviffcl
181 glcygantff haakayiegy htvpkgrcrq vvtgmawlff vswgmfpilf ilgpegfgvl
241 svygstvght iidlmskncw gllghylrvl ihehilihgd irkttklnig gteievetiv
301 edeaeagavn kgtgkyasre sflvmrdkmk ekgidvrasl dnskeveqeq aaraammmmn
361 gngmgmgmgm ngmngmggmn gmaggakpgl eltpqlqpgr vilavpdism vdffreqfaq
421 lsvtyelvpa lgadntlalv tqaqnlggvd fvlihpeflr drsstsilsr lrgagqrvaa
481 fgwaqlgpmr dliesanldg wlegpsfgqg ilpahivalv akmqqmrkmq qmqqigmmtg
541 gmngmgggmg ggmngmgggn gmnnmgngmg ggmgngmggn gmngmgggng mnnmggngma
601 gngmgggmgg ngmggsmngm ssgvvanvtp saaggmggmm nggmaapqsp gmnggrlgtn
661 plfnaapspl ssqlgaeagm gsmggmggms gmggmggmgg mggagaattq aaggnaeaem
721 lqnlmneinr lkrelge
```

A wild type (WT) Chop2 of the invention may be encoded by the following *Chlamydomonas reinhardtii* sensory opsin B (CSOB) mRNA sequence (GenBank Accession No. AF508966, and SEQ ID NO: 5):

```
   1 ttgacatctg tcgccaagca agcattaaac atggattatg gaggcgccct gagtgccgtt
  61 gggcgcgagc tgctatttgt aacgaaccca gtagtcgtca atggctctgt acttgtgcct
 121 gaggaccagt gttactgcgc gggctggatt gagtcgcgtg gcacaaacgg tgcccaaacg
 181 gcgtcgaacg tgctgcaatg gcttgctgct ggcttctcca tcctactgct tatgttttac
 241 gcctaccaaa catggaagtc aacctgcggc tgggaggaga tctatgtgtg cgctatcgag
 301 atggtcaagg tgattctcga gttcttcttc gagtttaaga cccgtccat gctgtatcta
 361 gccacaggcc accgcgtcca gtggttgcgt tacgccgagt ggcttctcac ctgcccggtc
 421 attctcattc acctgtcaaa cctgacgggc ttgtccaacg actacagcag gcgcaccatg
 481 ggtctgcttg tgtctgatat tggcacaatt gtgtgggcg ccacttccgc catggccacc
 541 ggatacgtca aggtcatctt cttctgcctg gtctgtgtt atggtgctaa cacgttcttt
 601 cacgctgcca aggcctacat cgagggttac cacaccgtgc cgaagggccg tgtcgccag
 661 gtggtgactg gcatggcttg gctcttcttc gtatcatggg gtatgttccc catcctgttc
 721 atcctcggcc ccgagggctt cggcgtcctg agcgtgtacg gctccaccgt cggccacacc
 781 atcattgacc tgatgtcgaa gaactgctgg ggtctgctcg gccactacct gcgcgtgctg
 841 atccacgagc atatcctcat ccacggcgac attcgcaaga ccaccaaatt gaacattggt
 901 ggcactgaga ttgaggtcga gacgctggtg gaggacgagg ccgaggctgg cgcggtcaac
 961 aagggcaccg gcaagtacgc ctcccgcgag tccttcctgg tcatgcgcga caagatgaag
1021 gagaagggca ttgacgtgcg cgcctctctg gacaacagca aggaggtgga gcaggagcag
1081 gccgccaggg ctgccatgat gatgatgaac ggcaatggca tgggtatggg aatgggaatg
1141 aacggcatga acggaatggg cggtatgaac gggatggctg gcggcgccaa gcccggcctg
1201 gagctcactc cgcagctaca gcccggccgc gtcatcctgg cggtgccgga catcagcatg
```

-continued

```
1261 gttgacttct tccgcgagca gtttgctcag ctatcggtga cgtacgagct ggtgccggcc
1321 ctgggcgctg acaacacact ggcgctggtt acgcaggcgc agaacctggg cggcgtggac
1381 tttgtgttga ttcaccccga gttcctgcgc gaccgctcta gcaccagcat cctgagccgc
1441 ctgcgcggcg cgggccagcg tgtggctgcg ttcggctggg cgcagctggg gcccatgcgt
1501 gacctgatcg agtccgcaaa cctggacggc tggctggagg gccctcgtt cggacagggc
1561 atcctgccgg cccacatcgt tgccctggtg gccaagatgc agcagatgcg caagatgcag
1621 cagatgcagc agattggcat gatgaccggc ggcatgaacg gcatgggcgg cggtatgggc
1681 ggcggcatga acggcatggg cggcggcaac ggcatgaaca acatgggcaa cggcatgggc
1741 ggcggcatgg gcaacggcat gggcggcaat ggcatgaacg gaatggggtgg cggcaacggc
1801 atgaacaaca tgggcggcaa cggaatggcc ggcaacggaa tgggcggcgg catgggcggc
1861 aacggtatgg gtggctccat gaacggcatg agctccggcg tggtggccaa cgtgacgccc
1921 tccgccgccg gcggcatggg cggcatgatg aacggcggca tggctgcgcc ccagtcgccc
1981 ggcatgaacg gcgccgcct gggtaccaac ccgctcttca cgccgcgcc ctcaccgctc
2041 agctcgcagc tcggtgccga ggcaggcatg gcagcatgg gaggcatggg cggaatgagc
2101 ggaatgggag gcatgggtgg aatgggggc atgggcggcg ccggcgccgc cacgacgcag
2161 gctgcgggcg gcaacgcgga ggcggagatg ctgcagaatc tcatgaacga gatcaatcgc
2221 ctgaagcgcg agcttggcga gtaaaaggct ggaggccggt actgcgatac ctgcgagctc
2281 gcgcgcctga ctcgtcgtac acacggctca ggagcacgcg cgcgtggact tctcaacctg
2341 tgtgcaacgt atctagagcg gcctgtgcgc gaccgtccgt gagcattccg gtgcgatctt
2401 cccgccttcg caccgcaagt tcccttcctg gccctgctgc gcctgacgca tcgtccgaac
2461 ggaagggcg cttgatcagt aaagcattga agactgaagt cgtgcgaccg tagtgctatg
2521 gctctgcacg taagtgggcg ctgccctgct tactacgcat gcccaagac tgcttccttt
2581 tggtggccga ggcctggtc ccacatcatt catttgcata acgtactgtt tagttacata
2641 cgctttgctt aacctcgaca attgcaacat gggctgagag tccgtacggc ggctatggac
2701 gaaggtgtta tcggatgtga ttaggaatct cggttgaaag gcttcgagaa agtgagcttc
2761 ttctgtggct tctgttgggg tcatcaagaa gaacgacggt aaggcaaacg aggtaaaagt
2821 ggcacgtctt tgtgcacaac gggcccgtgg agagtggggg agtgcatgtg tgcggtccta
2881 acacgcgagt gcaaagcggg ctttctgga gctgggttac ggtctggctc ggcaactgct
2941 ctgtgtttta accacagctt cggaagtctg ggtatgtttt gttggcagaa acatttgggt
3001 aacttgaggg tgattcgtct ggagtcggac aacatggctg ccgtccgtgt gcagggacgg
3061 taatcaatga agctgaagct gtgatgctca ccacacgttg catacccctg cttacaaaaa
3121 cactttgatg tcgtggccaa actatgcgtg agcaaagagt taaagaggca tgagtgcatg
3181 gttgcggacg tgcgcaacaa ttgcatcaag tatttgacgc cttcaagcca acaagtgcgc
3241 gcgcggcaac ttgattaaca cgccggacgc agtggtgggg gcgtgtacag tgtttatgag
3301 ctgccattct gcgatccgta tgttaggtt gcgtgtgacg ccgcgcggct gtgggccctt
3361 acatggagag ttgggtgctt caccacacg ttggcgccgc tgaagggtgt gctatgtttt
3421 ggtaaagccg gggccctgaa gaccgcaacc gtagaaccgt actgaaaggg tgtcagcccg
3481 gggtaactgg atgccctggg acatagctat taatgttgaa gtgaagccgt caagccgagt
3541 gccgtgcgcc gctgtatcac caaggcccgt ccaaaaaaaa aaaaaaaaaa aaaaaaaaa
```

A wild type (WT) Chop2 of the invention may be encoded by the following *Chlamydomonas reinhardtii* sensory opsin B (CSOB) amino acid sequence (GenBank Accession No. AAM44040, and SEQ ID NO: 6):

```
 61   gfsilllmfy ayqtwkstcg weeiyvcaie mvkvilefff efknpsmlyl atghrvqwlr
121   yaewlltcpv ilihlsnltg lsndysrrtm gllvsdigti vwgatsamat gyvkviffcl
181   glcygantff haakayiegy htvpkgrcrq vvtgmawlff vswgmfpilf ilgpegfgvl
241   svygstvght iidlmskncw gllghylrvl ihehilihgd irkttklnig gteievetlv
301   edeaeagavn kgtgkyasre sflvmrdkmk ekgidvrasl dnskeveqeq aaraammmmn
361   gngmgmgmgm ngmngmggmn gmaggakpgl eltpqlqpgr vilavpdism vdffreqfaq
421   lsvtyelvpa lgadntlalv tqaqnlggvd fvlihpeflr drsstsilsr lrgagqrvaa
481   fgwaqlgpmr dliesanldg wlegpsfgqg ilpahivalv akmqqmrkmq qmqqigmmtg
541   gmngmgggmg ggmngmgggn gmnnmgngmg ggmgngmggn gmngmgggng mnnmggngma
601   gngmgggmgg ngmggsmngm ssgvvanvtp saaggmggmm nggmaapqsp gmnggrlgtn
661   plfnaapspl ssqlgaeagm gsmggmggms gmggmggmgg mggagaattq aaggnaeaem
721   lqnlmneinr lkrelge
```

A wild type (WT) Chop2 of the invention may be encoded by the following *Chlamydomonas reinhardtii* acop2 mRNA for archaeal-type opsin 2 nucleic acid sequence (GenBank Accession No. AB058891, and SEQ ID NO: 7):

```
   1 catctgtcgc caagcaagca ttaaacatgg attatggagg cgccctgagt gccgttgggc
  61 gcgagctgct atttgtaacg aacccagtag tcgtcaatgg ctctgtactt gtgcctgagg
 121 accagtgtta ctgcgcgggc tggattgagt cgcgtggcac aaacggtgcc caaacgcgt
 181 cgaacgtgct gcaatggctt gctgctggct tctccatcct actgcttatg ttttacgcct
 241 accaaacatg gaagtcaacc tgcggctggg aggagatcta tgtgtgcgct atcgagatgg
 301 tcaaggtgat tctcgagttc ttcttcgagt ttaagaaccc gtccatgctg tatctagcca
 361 caggccaccg cgtccagtgg ttgcgttacg ccgagtggct tctcacctgc ccggtcattc
 421 tcattcacct gtcaaacctg acgggcttgt ccaacgacta cagcaggcgc accatgggtc
 481 tgcttgtgtc tgatattggc acaattgtgt ggggcgccac ttccgccatg gccaccggat
 541 acgtcaaggt catcttcttc tgcctgggtc tgtgttatgg tgctaacacg ttctttcacg
 601 ctgccaaggc ctacatcgag ggttaccaca ccgtgccgaa gggccggtgt cgccaggtgg
 661 tgactggcat ggcttggctc ttcttcgtat catggggtat gttccccatc ctgttcatcc
 721 tcggccccga gggcttcggc gtcctgagcg tgtacggctc caccgtcggc cacaccatca
 781 ttgacctgat gtcgaagaac tgctggggtc tgctcggcca ctacctgcgc gtgctgatcc
 841 acgagcatat cctcatccac ggcgacattc gcaagaccac caaattgaac attggtggca
 901 ctgagattga ggtcgagacg ctggtggagg acgaggccga ggctggcgcg gtcaacaagg
 961 gcaccggcaa gtacgcctcc cgcgagtcct tcctggtcat gcgcgacaag atgaaggaga
1021 agggcattga cgtgcgcgcc tctctggaca acagcaagga ggtggagcag gagcaggccg
1081 ccagggctgc catgatgatg atgaacggca atggcatggg tatgggaatg gaatgaacg
1141 gcatgaacgg aatgggcggt atgaacggga tggctggcgg cgccaagccc ggcctggagc
1201 tcactccgca gctacagccc ggccgcgtca tcctggcggt gccggacatc agcatggttg
1261 acttcttccg cgagcagttt gctcagctat cggtgacgta cgagctggtg ccggccctgg
```

```
-continued
1321 gcgctgacaa cacactggcg ctggttacgc aggcgcagaa cctgggcggc gtggactttg 1381 tgttgattca ccccgagttc ctgcgcgacc gctctagcac cagcatcctg agccgcctgc 1441 gcggcgcggg ccagcgtgtg gctgcgttcg gctgggcgca gctggggccc atgcgtgacc 1501 tgatcgagtc cgcaaacctg gacggctggc tggagggccc ctcgttcgga cagggcatcc 1561 tgccggccca catcgttgcc ctggtggcca agatgcagca gatgcgcaag atgcagcaga 1621 tgcagcagat tggcatgatg accggcggca tgaacggcat gggcggcggt atgggcggcg 1681 gcatgaacgg catgggcggc ggcaacggca tgaacaacat gggcaacggc atgggcggcg 1741 gcatgggcaa cggcatgggc ggcaatggca tgaacggaat gggtggcggc aacggcatga 1801 acaacatggg cggcaacgga atggccggca acggaatggg cggcggcatg ggcggcaacg 1861 gtatgggtgg ctccatgaac ggcatgagct ccggcgtggt ggccaacgtg acgccctccg 1921 ccgccggcgg catgggcggc atgatgaacg gcggcatggc tgcgccccag tcgcccggca 1981 tgaacgccgg ccgcctgggt accaacccgc tcttcaacgc cgcgccctca ccgctcagct 2041 cgcagctcgg tgccgaggca ggcatgggca gcatgggagg catgggcgga atgagcggaa 2101 tgggaggcat gggtggaatg gggggcatgg gcggcgccgg cgccgccacg acgcaggctg 2161 cgggcggcaa cgcggaggcg gagatgctgc agaatctcat gaacgagatc aatcgcctga 2221 agcgcgagct tggcgagtaa aaggctggag gccggtactg cgatacctgc gagctcgcgc 2281 gcctgactcg tcgtacacac ggctcaggag cacgcgcgcg tggacttctc aacctgtgtg 2341 caacgtatct agagcggcct gtgcgcgacc gtccgtgagc attccggtgc gatcttcccg 2401 ccttcgcacc gcaagttccc ttcctggccc tgctgcgcct gacgcatc
```

A wild type (WT) Chop2 of the invention may be encoded by the following *Chlamydomonas reinhardtii* acop2 mRNA for archaeal-type opsin 2 amino acid sequence (GenBank Accession No. BAB68567, and SEQ ID NO: 8):

```
  1 mdyggalsav grellfvtnp vvvngsvlvp edqcycagwi esrgtngaqt asnvlqwlaa 61 gfsilllmfy ayqtwkstcg weeiyvcaie mvkvilefff efknpsmlyl atghrvqwlr 121 yaewlltcpv ilihlsnltg lsndysrrtm gllvsdigti vwgatsamat gyvkviffcl 181 glcygantff haakayiegy htvpkgrcrq vvtgmawlff vswgmfpilf ilgpegfgvl 241 svygstvght iidlmskncw gllghylrvl ihehilihgd irkttklnig gteievetlv 301 edeaeagavn kgtgkyasre sflvmrdkmk ekgidvrasl dnskeveqeq aaraammmmn 361 gngmgmgmgm ngmngmggmn gmaggakpgl eltpqlqpgr vilavpdism vdffreqfaq 421 lsvtyelvpa lgadntlalv tqaqnlggvd fvlihpeflr drsstsilsr lrgagqrvaa 481 fgwaqlgpmr dliesanldg wlegpsfgqg ilpahivalv akmqqmrkmq qmqqigmmtg 541 gmngmgggmg ggmngmgggn gmnnmgngmg ggmgngmggn gmngmgggng mnnmggngma 601 gngmgggmgg ngmggsmngm ssgvvanvtp saaggmggmm nggmaapqsp gmnggrlgtn 661 plfnaapspl ssqlgaeagm gsmggmggms gmggmggmgg mggagaattq aaggnaeaem 721 lqnlmneinr lkrelge
``` cysteine or an alanine. In some preferred embodiments, the amino acid at position 159 is mutated from a threonine to an alanine, a cysteine, or a serine. In all embodiments, the Chop2 mutants form a functional ChR2 channel.

ChR2 Mutants

The present invention provides Chop2 mutants wherein one or more amino acids are mutated. In some embodiments, the Chop2 is the full-length polypeptide, such as SEQ ID NOs: 2, 4, 6, and 8, with at least one amino acid mutation. In some embodiments, the mutation is at amino acid 132 and/or amino acid 159. In some preferred embodiments, the amino acid at position 132 is mutated from a leucine to a The present invention also encompasses Chop2 proteins and nucleic acids that encode a biologically active fragment or a conservative amino acid substitution or other mutation variant of Chop2. Non-limiting examples of useful fragments include polypeptides encoding amino acids 1-315 of the wild-type Chop2, i.e., SEQ ID NO: 26, wherein at least one amino acid is mutated or conservatively substituted, for example at amino acid positions 132 and/or 159. Smaller fragments of wild-type Chop2, wherein at least one amino acid is mutated or conservatively substituted (i.e., at amino acid positions 132 and/or 159) may also be useful in the present invention. Accordingly, Chop2 polypeptides and nucleic acids of the present invention further include, but are not limited to, biologically active fragments encoding amino acids 1-315, 1-310, 1-300, 1-275, 1-250, 1-225, 1-200, 1-175, or 1-160 of the wild-type Chop2, wherein at least one amino acid is mutated or conservatively substituted, for example at amino acid positions 132 and/or 159. In other embodiments, the Chop2 polypeptides and nucleic acids of the present invention can be up to, or about, 315 amino acids long, 310 amino acids long, 300 amino acids long, 275 amino acids long, 250 amino acids long, 225 amino acids long, 200 amino acids long, 175 amino acids long, or 160 amino acids long.

A single mutant Chop2 of the invention may be encoded by the following Synthetic construct hVChR1-mKate-betahChR2(L132C) gene sequence (GenBank Accession No. JN836746, and SEQ ID NO: 9) with the following annotations, GFP sequence is in bold, L132C Chop2 sequence is underlined:

```
   1 atggattacc ctgtggcccg gtccctgatt gtaagatacc ccaccgatct gggcaatgga
  61 accgtgtgca tgcccagagg acaatgctac tgcgaggggt ggctgaggag ccggggcact
 121 agtatcgaaa aaccatcgc tatcaccctc cagtgggtag tgttcgctct gtccgtagcc
 181 tgtctcggct ggtatgcata ccaagcctgg agggctacct gtgggtggga ggaagtatac
 241 gtggccctga tcgagatgat gaagtccatc atcgaggctt tccatgagtt cgactcccca
 301 gccacactct ggctcagcag tgggaatggc gtagtgtgga tgagatatgg agagtggctg
 361 ctgacctgtc ccgtcctgct cattcatctg tccaatctga ccgggctgaa agatgactac
 421 tccaagagaa caatgggact gctggtgagt gacgtggggt gtattgtgtg gggagccacc
 481 tccgccatgt gcactggatg gaccaagatc ctcttttcc tgatttccct ctcctatggg
 541 atgtatacat acttccacgc cgctaaggtg tatattgagg ccttccacac tgtacctaaa
 601 ggcatctgta gggagctcgt gcgggtgatg gcatggacct tctttgtggc ctggggatg
 661 ttccccgtgc tgttcctcct cggcactgag ggatttggcc acattagtcc ttacgggtcc
 721 gcaattggac actccatcct ggatctgatt gccaagaata tgtgggggt gctgggaaat
 781 tatctgcggg taaagatcca cgagcatatc ctgctgtatg gcgatatcag aaagaagcag
 841 aaaatcacca ttgctggaca ggaaatggag gtggagacac tggtagcaga ggaggaggac
 901 gggaccgcgg tcgccaccat ggtgtctaag ggcgaagagc tgattaagga gaacatgcac
 961 atgaagctgt acatggaggg caccgtgaac aaccaccact tcaagtgcac atccgagggc
1021 gaaggcaagc cctacgaggg cacccagacc atgagaatca aggtggtcga gggcggccct
1081 ctccccttcg ccttcgacat cctggctacc agcttcatgt acggcagcaa aaccttcatc
1141 aaccacaccc agggcatccc cgacttcttt aagcagtcct tccctgaggg cttcacatgg
1201 gagagagtca ccacatacga agacgggggc gtgctgaccg ctacccagga caccagcctc
1261 caggacggct gcctcatcta caacgtcaag atcagagggg tgaacttccc atccaacggc
1321 cctgtgatgc agaagaaaac actcggctgg gaggcctcca ccgagatgct gtacccgct
1381 gacggcggcc tggaaggcag agccgacatg gccctgaagc tcgtgggcgg gggccacctg
1441 atctgcaact tgaagaccac atacagatcc aagaaacccg ctaagaacct caagatgccc
1501 ggcgtctact atgtggacag aagactggaa agaatcaagg aggccgacaa agagacctac
1561 gtcgagcagc acgaggtggc tgtggccaga tactgcgacc tccctagcaa actggggcac
1621 aaacttaatt gcctgcagga gaagaagtca tgcagccagc gcatggccga attccggcaa
1681 tactgttgga acccggacac tgggcagatg ctgggccgca ccccagcccg tgggtgtgg
1741 atcagcctgt actatgcagc tttctacgtg gtcatgactg gctctttgc cttgtgcatc
1801 tatgtgctga tgcagaccat tgatccctac accccccgact accaggacca gttaaagtca
1861 ccgggggtaa ccttgagacc ggatgtgtat ggggaaagag ggctgcagat ttcctacaac
1921 atctctgaaa acagctctag acaggcccag atcaccggac gtccggagac tgagacattg
```

-continued

```
1981 ccaccggtgg actacggggg ggccctgagc gctgtgggca gagaactcct gttcgtgaca 2041 aatccagtcg tggtgaacgg ctccgtactc gtacccgagg atcagtgcta ttgcgcagga 2101 tggatcgaga gcagaggcac aaacggcgca cagactgcat ccaacgtgct ccagtggttg 2161 gccgcaggct tttccattct cctgctcatg ttttacgcct accagacttg gaagtccaca 2221 tgtggctggg aggaaatcta cgtgtgtgca atcgaaatgg tgaaggtgat cctggagttt 2281 ttcttcgaat ttaaaaaccc aagcatgctg tacctggcta ctggccacag agtgcagtgg 2341 ctgcggtatg ccgaatggct gctgacttgc ccagtgattt gcatccacct gtccaacctg 2401 actgggctgt ctaacgatta cagtaggaga acaatgggac tgctcgtatc cgacatcggc 2461 actatcgtat ggggcgcaac tagtgccatg gccactggat acgtgaaagt gatcttcttc 2521 tgcctgggac tctgctacgg agcaaacaca ttttttcatg ccgcaaaagc atatatcgag 2581 gggtatcata ccgtcccaaa gggccggtgt agacaagtgg tgactggcat ggcttggctg 2641 ttcttcgtgt cctggggat gtttcccatc ctctttatcc tgggcccaga aggcttcggg 2701 gtgctgagtg tgtatggcag taccgtagga cacactatca ttgacctgat gagcaaaaac 2761 tgctggggc tgctcggcca ctacctgaga gtactcatcc acgagcatat cctgattcat 2821 ggcgatatcc ggaaaactac caagctcaat atcgggggca ccgagattga agtggagaca 2881 ctcgtggagg acgaggccga ggccggagca gtgaacaaag gcactggcaa gtatgcctcc 2941 agagaatcct ttctggtgat gcgggacaaa atgaaggaga aaggcattga tgtacggtgc 3001 agtaatgcca aagccgtcga gactgatgtg tag
```

A single mutant ChR2 of the invention may be encoded by the following Synthetic construct hVChR1-mKate-betahChR2(L132C) amino acid sequence (GenBank Accession No. AER29839, and SEQ ID NO: 10) with the following annotations, GFP sequence is in bold, L132C Chop2 [35] sequence is underlined:

```
  1 mdypvarsli vryptdlgng tvcmprgqcy cegwlrsrgt siektiaitl qwvvfalsva 61 clgwyayqaw ratcgweevy valiemmksi ieafhefdsp atlwlssgng vvwmrygewl 121 ltcpvllihl snltglkddy skrtmgllvs dvgcivwgat samctgwtki lfflislsyg 181 mytyfhaakv yieafhtvpk gicrelvrvm awtffvawgm fpvlfllgte gfghispygs 241 aighsildli aknmwgvlgn ylrvkihehi llygdirkkq kitiagqeme vetlvaeeed 301 gtavatmvsk geelikenmh mklymegtvn nhhfkctseg egkpyegtqt mrikvveggp 361 lpfafdilat sfmygsktfi nhtqgipdff kqsfpegftw ervttyedgg vltatqdtsl 421 qdgcliynvk irgvnfpsng pvmqkktlgw eastemlypa dgglegradm alklvggghl 481 icnlkttyrs kkpaknlkmp gvyyvdrrle rikeadkety veqhevavar ycdlpsklgh 541 klnclqekks csqrmaefrq ycwnpdtgqm lgrtparwvv islyyaafyv vmtglfalci 601 yvlmqtidpy tpdyqdqlks pgvtlrpdvy gerglqisyn isenssrqaq itgrpetetl 661 ppvdyqgals avqrellfvt npvvvnqsvl vpedqcycaq wiesrqtnga qtasnvlqwl 721 aagfsilllm fyayqtwkst cgweeiyvca iemvkvilef ffefknpsml ylatghrvqw 781 lryaewlltc pvicihlsnl tglsndysrr tmgllvsdig tivwgatsam atqyvkviff 841 clglcygant ffhaakayie gyhtvpkgrc rqvvtgmawl ffvswqmfpi lfilgpegfg 901 vlsvygstvg htiidlmskn cwgllghylr vlihehilih gdirkttkln iggteievet 961 lvedeaeaga vnkgtgkyas resflvmrdk mkekgidvrc snakavetdv
```

A single mutant Chop2 of the invention may be encoded by the following Synthetic construct hVChR1-mKate-betahChR2(L132C) gene sequence (GenBank Accession No. 1N836745, and SEQ ID NO: 11) with the following annotations, GFP sequence is in bold, L132C Chop2 sequence is underlined:

```
   1 atggattacc ctgtggcccg gtccctgatt gtaagatacc ccaccgatct gggcaatgga
  61 accgtgtgca tgcccagagg acaatgctac tgcgaggggt ggctgaggag ccggggcact
 121 agtatcgaaa aaaccatcgc tatcaccctc cagtgggtag tgttcgctct gtccgtagcc
 181 tgtctcggct ggtatgcata ccaagcctgg agggctacct gtgggtggga ggaagtatac
 241 gtggccctga tcgagatgat gaagtccatc atcgaggctt ccatgagtt cgactcccca
 301 gccacactct ggctcagcag tgggaatggc gtagtgtgga tgagatatgg agagtggctg
 361 ctgacctgtc ccgtcctgct cattcatctg tccaatctga ccgggctgaa agatgactac
 421 tccaagagaa caatgggact gctggtgagt gacgtgggt gtattgtgtg gggagccacc
 481 tccgccatgt gcactggatg gaccaagatc ctcttttcc tgatttccct ctcctatggg
 541 atgtatacat acttccacgc cgctaaggtg tatattgagg ccttccacac tgtacctaaa
 601 ggcatctgta gggagctcgt gcgggtgatg gcatggacct tctttgtggc ctgggggatg
 661 ttccccgtgc tgttcctcct cggcactgag ggatttggcc acattagtcc ttacgggtcc
 721 gcaattggac actccatcct ggatctgatt gccaagaata tgtgggggt gctgggaaat
 781 tatctgcggg taaagatcca cgagcatatc ctgctgtatg cgatatcag aaagaagcag
 841 aaaatcacca ttgctggaca ggaaatggag gtggagacac tggtagcaga ggaggaggac
 901 gggaccgcgg tcgccaccat ggtgtctaag ggcgaagagc
```
tgattaagga gaacatgcac atgaagctgt acatggaggg caccgtgaac aaccaccact caagtgcac atccgagggc gaaggcaagc cctacgaggg cacccagacc atgagaatca aggtggtcga gggcggccct ctccccttcg ccttcgacat cctggctacc agcttcatgt acggcagcaa aaccttcatc aaccacaccc agggcatccc cgacttcttt aagcagtcct ccctgagg cttcacatgg gagagagtca ccacatacga agacgggggc gtgctgaccg ctacccagga caccagcctc caggacggct gcctcatcta caacgtcaag atcagagggg tgaacttccc atccaacggc cctgtgatgc agaagaaaac actcggctgg gaggcctcca ccgagatgct gtacccgct gacggcggcc tggaaggcag agccgacatg gccctgaagc tcgtgggcgg gggccacctg atctgcaact tgaagaccac atacagatcc aagaaacccg ctaagaacct caagatgccc ggcgtctact atgtggacag aagactggaa agaatcaagg aggccgacaa agagacctac gtcgagcagc acgaggtggc tgtggccaga tactgcgacc tccctagcaa actgggcac

```
1621 aaacttaatt gcctgcagga gaagaagtca tgcagccagc gcatggccga attccggcaa
1681 tactgttgga acccggacac tgggcagatg ctggccgcaa ccccagccg gtgggtgtgg
1741 atcagcctgt actatgcagc tttctacgtg gtcatgactg gctctttgc cttgtgcatc
1801 tatgtgctga tgcagaccat tgatcccta cccccgact accaggacca gttaaagtca
1861 ccggggtaa ccttgagacc ggatgtgtat ggggaaagag ggctgcagat tcctacaac
1921 atctctgaaa acagctctag acaggcccag atcaccggac gtccggagac tgagacattg
1981 ccaccggtgg actacggggg ggccctgagc gctgtgggca gagaactcct gttcgtgaca
```
aatccagtcg tggtgaacgg ctccgtactc gtacccgagg atcagtgcta ttgcgcagga tggatcgaga gcagaggcac aaacggcgca cagactgcat ccaacgtgct ccagtggttg gccgcaggct tttccattct cctgctcatg tttacgcct accagacttg gaagtccaca -continued

```
2221 tgtggctggg aggaaatcta cgtgtgtgca atcgaaatgg tgaaggtgat cctggagttt 2281 ttcttcgaat ttaaaaaccc aagcatgctg tacctggcta ctggccacag agtgcagtgg 2341 ctgcggtatg ccgaatggct gctgacttgc ccagtgattc tgatccacct gtccaacctg 2401 actgggctgt ctaacgatta cagtaggaga acaatgggac tgctcgtatc cgacatcggc 2461 actatcgtat ggggcgcaac tagtgccatg gccactggat acgtgaaagt gatcttcttc 2521 tgcctgggac tctgctacgg agcaaacaca ttttttcatg ccgcaaaagc atatatcgag 2581 gggtatcata ccgtcccaaa gggccggtgt agacaagtgg tgactggcat ggcttggctg 2641 ttcttcgtgt cctgggggat gtttcccatc ctctttatcc tgggcccaga aggcttcggg 2701 gtgctgagtg tgtatggcag taccgtagga cacactatca ttgacctgat gagcaaaaac 2761 tgctggggc tgctcggcca ctacctgaga gtactcatcc acgagcatat cctgattcat 2821 ggcgatatcc ggaaaactac caagctcaat atcgggggca ccgagattga agtggagaca 2881 ctcgtggagg acgaggccga ggccggagca gtgaacaaag gcactggcaa gtatgcctcc 2941 agagaatcct ttctggtgat gcgggacaaa atgaaggaga aaggcattga tgtacggtgc 3001 agtaatgcca aagccgtcga gactgatgtg tag
```

A single mutant Chop2 of the invention may be encoded by the following Synthetic construct hVChR1-mKate-betahChR2(L132C) amino acid sequence (GenBank Accession No. AER29838, and SEQ ID NO: 12) with the following annotations, GFP sequence is in bold, L132C Chop2 sequence is underlined:

```
  1 mdypvarsli vryptdlgng tvcmprgqcy cegwlrsrgt siektiaitl qwvvfalsva 61 clgwyayqaw ratcgweevy valiemmksi ieafhefdsp atlwlssgng vvwmrygewl 121 ltcpvllihl snltglkddy skrtmgllvs dvgcivwgat samctgwtki lfflislsyg 181 mytyfhaakv yieafhtvpk gicrelvrvm awtffvawgm fpvlfllgte gfghispygs 241 aighsildli aknmwgvlgn ylrvkihehi llygdirkkq kitiagqeme vetlvaeeed 301 gtavatmvsk geelikenmh mklymegtvn nhhfkctseg egkpyegtqt mrikvveggp 361 lpfafdilat sfmygsktfi nhtqgipdff kqsfpegftw ervttyedgg vltatqdtsl 421 qdgcliynvk irgvnfpsng pvmqkktlgw eastemlypa dgglegradm alklvggghl 481 icnlkttyrs kkpaknlkmp gvyyvdrrle rikeadkety veqhevavar ycdlpsklgh 541 klnclqekks csqrmaefrq ycwnpdtgqm lgrtparwvv islyyaafyv vmtglfalci 601 yvlmqtidpy tpdyqdqlks pgvtlrpdvy gerglqisyn isenssrqaq itgrpetetl 661 ppvdyggals avgrellfvt npvvvngsvl vpedqcycag wiesrgtnga qtasnvlqwl 721 aaqfsilllm fyayqtwkst cqweeiyvca iemvkvilef ffefknpsml ylatqhrvqw 781 lryaewlltc pvilihlsnl tqlsndysrr tmgllvsdiq tivwqatsam atqyvkviff 841 clglcygant ffhaakayie gyhtvpkgrc rqvvtgmawl ffvswqmfpi lfilgpegfg 901 vlsvygstvg htiidlmskn cwgllqhylr vlihehilih qdirkttkln iggteievet 961 lvedeaeaga vnkgtgkyas resflvmrdk mkekgidvrc snakavetdv
```

A L132C single mutant Chop2 of the invention may be encoded by the following amino acid sequence (positions 132 underlined and bolded, SEQ ID NO: 13):

```
  1 MDYGGALSAV GRELLFVTNP VVVNGSVLVP EDQCYAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV IC̲IHLSNLTG LSNDYSRRTM GLLVSDIGTI VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK
```

A T159C single mutant Chop2 of the invention may be encoded by the following amino acid sequence (positions 159 underlined and bolded, SEQ ID NO: 14):

```
  1 MDYGGALSAV GRELLFVTNP VVVNGSVLVP EDQCYAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV ILIHLSNLTG LSNDYSRRTM GLLVSDIGC̲I VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK
```

A L132C/T159C double mutant Chop2 of the invention may be encoded by the following nucleotide sequence (SEQ ID NO: 15):

```
  1 atggactacg gggggctct gtctgctgtc gggagggaac tgctgtttgt gactaaccct 61 gtcgtcgtga acgggagtgt gctggtccct gaggaccagt gctactgtgc cggctggatc 121 gaatcacgcg gaaccaacgg ggcccagaca gctagcaatg tgctgcagtg gctggccgct 181 gggtttagta tcctgctgct gatgttctac gcctatcaga cttggaagtc aacctgcggc 241 tgggaggaaa tctacgtgtg cgctattgag atggtgaaag tgatcctgga gttcttcttc 301 gagttcaaga acccaagcat gctgtacctg gctactggac accgagtgca gtggctgaga 361 tatgcagaat ggctgctgac atgccccgtc atctgcattc acctgtccaa cctgacaggc 421 ctgagcaatg actactccag gagaactatg ggactgctgg tgtccgacat cggctgcatt 481 gtctggggag caacttctgc tatggcaacc ggatacgtga aggtcatctt tttctgcctg 541 gggctgtgct atggcgcaaa taccttttc cacgcagcca aggcctacat tgagggtat 601 cataccgtgc caaaaggccg tgccgacag tggtcacag aatggcttg gctgtttttc 661 gtctcttggg aatgtttcc catcctgttc attctggggc tgaagggtt cggcgtgctg 721 tctgtctacg gaagtacagt ggggcatact atcattgacc tgatgtccaa aaactgttgg 781 ggcctgctgg acactatct gagagtgctg atccacgagc atatcctgat tcatggcgat 841 attcggaaga ccacaaaact gaatatcggc ggaaccgaga ttgaagtgga aacactggtg 901 gaagacgagg ctgaggctgg ggctgtgaac aaggggactg gcaaa
```

A L132C/T159C double mutant Chop2 of the invention may be encoded by the following amino acid sequence (positions 132 and 159 underlined and bolded, SEQ ID NO: 16):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ICIHLSNLTG LSNDYSRRTM GLLVSDIGCI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A T159S single mutant Chop2 of the invention may be encoded by the following amino acid sequence (positions 159 underlined and bolded, SEQ ID NO: 17):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ILIHLSNLTG LSNDYSRRTM GLLVSDIGSI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A L132C/T159S double mutant Chop2 of the invention may be encoded by the following nucleotide sequence (SEQ ID NO: 18):

```
  1 atggactacg gggggctct gtctgctgtc gggagggaac tgctgtttgt gactaaccct
 61 gtcgtcgtga acgggagtgt gctggtccct gaggaccagt gctactgtgc cggctggatc
121 gaatcacgcg gaaccaacgg ggcccagaca gctagcaatg tgctgcagtg gctggccgct
181 gggtttagta tcctgctgct gatgttctac gcctatcaga cttggaagtc aacctgcggc
241 tgggaggaaa tctacgtgtg cgctattgag atggtgaaag tgatcctgga gttcttcttc
301 gagttcaaga acccaagcat gctgtacctg gctactggac accgagtgca gtggctgaga
361 tatgcagaat ggctgctgac atgccccgtc atctgcattc acctgtccaa cctgacaggc
421 ctgagcaatg actactccag gagaactatg ggactgctgg tgtccgacat cggcagcatt
481 gtctggggag caacttctgc tatggcaacc ggatacgtga aggtcatctt tttctgcctg
541 gggctgtgct atggcgcaaa tacctttttc cacgcagcca aggcctacat tgaggggtat
601 cataccgtgc caaaaggccg gtgccgacag gtggtcacag aatggcttg gctgtttttc
661 gtctcttggg gaatgtttcc catcctgttc attctgggc ctgaagggtt cggcgtgctg
721 tctgtctacg gaagtacagt ggggcatact atcattgacc tgatgtccaa aaactgttgg
781 ggcctgctgg gacactatct gagagtgctg atccacgagc atatcctgat tcatggcgat
841 attcggaaga ccacaaaact gaatatcggc ggaaccgaga ttgaagtgga aacactggtg
901 gaagacgagg ctgaggctgg ggctgtgaac aaggggactg gcaaa
```

A L132C/T159S double mutant Chop2 of the invention may be encoded by the following amino acid sequence (positions 132 and 159 underlined and bolded, SEQ ID NO: 19):

```
  1 MDYGGALSAV GRELLFVTNP VVVNGSVLVP EDQCYCAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV ICIHLSNLTG LSNDYSRRTM GLLVSDIGSI VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK
```

A L132A single mutant Chop2 of the invention may be encoded by the following amino acid sequence (position 132 underlined and bolded, SEQ ID NO: 20):

```
  1 MDYGGALSAV GRELLFVTNP VVVNGSVLVP EDQCYCAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV IAIHLSNLTG LSNDYSRRTM GLLVSDIGTI VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK
```

A L132A/T159C double mutant Chop2 of the invention may be encoded by the following nucleotide sequence (SEQ ID NO: 21):

```
  1 ATGGACTACG GGGGGCTCT GTCTGCTGTC GGGAGGGAAC TGCTGTTTGT GACTAACCCT

61 GTCGTCGTGA ACGGGAGTGT GCTGGTCCCT GAGGACCAGT GCTACTGTGC CGGCTGGATC

121 GAATCACGCG GAACCAACGG GGCCCAGACA GCTAGCAATG TGCTGCAGTG GCTGGCCGCT

181 GGGTTTAGTA TCCTGCTGCT GATGTTCTAC GCCTATCAGA CTTGGAAGTC AACCTGCGGC

241 TGGGAGGAAA TCTACGTGTG CGCTATTGAG ATGGTGAAAG TGATCCTGGA GTTCTTCTTC

301 GAGTTCAAGA ACCCAAGCAT GCTGTACCTG GCTACTGGAC ACCGAGTGCA GTGGCTGAGA

361 TATGCAGAAT GGCTGCTGAC ATGCCCCGTC ATCGCCATTC ACCTGTCCAA CCTGACAGGC

421 CTGAGCAATG ACTACTCCAG GAGAACTATG GGACTGCTGG TGTCCGACAT CGGCTGCATT

481 GTCTGGGGAG CAACTTCTGC TATGGCAACC GGATACGTGA AGGTCATCTT TTTCTGCCTG

541 GGGCTGTGCT ATGGCGCAAA TACCTTTTTC CACGCAGCCA AGGCCTACAT TGAGGGGTAT

601 CATACCGTGC CAAAAGGCCG GTGCCGACAG GTGGTCACAG GAATGGCTTG GCTGTTTTTC

661 GTCTCTTGGG GAATGTTTCC CATCCTGTTC ATTCTGGGGC CTGAAGGGTT CGGCGTGCTG

721 TCTGTCTACG GAAGTACAGT GGGGCATACT ATCATTGACC TGATGTCCAA AAACTGTTGG

781 GGCCTGCTGG GACACTATCT GAGAGTGCTG ATCCACGAGC ATATCCTGAT TCATGGCGAT

841 ATTCGGAAGA CCACAAAACT GAATATCGGC GGAACCGAGA TTGAAGTGGA AACACTGGTG

901 GAAGACGAGG CTGAGGCTGG GGCTGTGAAC AAGGGGACTG GCAAA
```

A L132A/T159C double mutant Chop2 of the invention may be encoded by the following amino acid sequence (positions 132 and 159 underlined and bolded, SEQ ID NO: 22):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV IAIHLSNLTG LSNDYSRRTM GLLVSDIGCI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
```

A T159A single mutant Chop2 of the invention may be encoded by the following amino acid sequence (position 159 underlined and bolded, SEQ ID NO: 23):

```
  1 MDYGGALSAV GRELLFVTNP VVVNGSVLVP EDQCYCAGWI ESRGTNGAQT ASNVLQWLAA
 61 GFSILLLMFY AYQTWKSTCG WEEIYVCAIE MVKVILEFFF EFKNPSMLYL ATGHRVQWLR
121 YAEWLLTCPV ILIHLSNLTG LSNDYSRRTM GLLVSDIGAI VWGATSAMAT GYVKVIFFCL
181 GLCYGANTFF HAAKAYIEGY HTVPKGRCRQ VVTGMAWLFF VSWGMFPILF ILGPEGFGVL
241 SVYGSTVGHT IIDLMSKNCW GLLGHYLRVL IHEHILIHGD IRKTTKLNIG GTEIEVETLV
301 EDEAEAGAVN KGTGK
                                                                  30
```

A L132C/T159A double mutant Chop2 of the invention may be encoded by the following nucleotide sequence (SEQ ID NO: 24):

```
  1 atggactacg gggggctct gtctgctgtc gggagggaac tgctgtttgt gactaaccct
 61 gtcgtcgtga acgggagtgt gctggtccct gaggaccagt gctactgtgc cggctggatc
121 gaatcacgcg gaaccaacgg ggcccagaca gctagcaatg tgctgcagtg gctggccgct
181 gggtttagta tcctgctgct gatgttctac gcctatcaga cttggaagtc aacctgcggc
241 tgggaggaaa tctacgtgtg cgctattgag atggtgaaag tgatcctgga gttcttcttc
301 gagttcaaga acccaagcat gctgtacctg gctactggac accgagtgca gtggctgaga
361 tatgcagaat ggctgctgac atgccccgtc atctgcattc acctgtccaa cctgacaggc
421 ctgagcaatg actactccag gagaactatg ggactgctgg tgtccgacat cggcgccatt
481 gtctggggag caacttctgc tatggcaacc ggatacgtga aggtcatctt tttctgcctg
541 gggctgtgct atggcgcaaa taccttttc cacgcagcca aggcctacat tgaggggtat
601 cataccgtgc caaaaggccg tgccgacag gtggtcacag aatggcttg gctgttttc
661 gtctcttggg gaatgtttcc catcctgttc attctgggc ctgaagggtt cggcgtgctg
721 tctgtctacg gaagtacagt ggggcatact atcattgacc tgatgtccaa aaactgttgg
781 ggcctgctgg gacactatct gagagtgctg atccacgagc atatcctgat tcatggcgat
841 attcggaaga ccacaaaact gaatatcggc ggaaccgaga ttgaagtgga aacactggtg
901 gaagacgagg ctgaggctgg ggctgtgaac aagggggactg gcaaa
```

A L132C/T159A double mutant Chop2 of the invention may be encoded by the following amino acid sequence (positions 132 and 159 underlined and bolded, SEQ ID NO: 25):

```
  1 MDYGGALSAV GRELLFVTNP VVVNGSVLVP EDQCYCAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV ICIHLSNLTG LSNDYSRRTM GLLVSDIGAI VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK
```

A wild type (WT) Chop2 of the invention may be encoded by the following amino acid sequence (SEQ ID NO: 26):

```
  1 MDYGGALSAV GRELLFVTNP VVVNGSVLVP EDQCYCAGWI ESRGTNGAQT ASNVLQWLAA

61 GFSILLLMFY AYQTWKSTCG WEEIYVCAIE MVKVILEFFF EFKNPSMLYL ATGHRVQWLR

121 YAEWLLTCPV ILIHLSNLTG LSNDYSRRTM GLLVSDIGTI VWGATSAMAT GYVKVIFFCL

181 GLCYGANTFF HAAKAYIEGY HTVPKGRCRQ VVTGMAWLFF VSWGMFPILF ILGPEGFGVL

241 SVYGSTVGHT IIDLMSKNCW GLLGHYLRVL IHEHILIHGD IRKTTKLNIG GTEIEVETLV

301 EDEAEAGAVN KGTGK
```

Mutant ChR2 proteins of the invention also demonstrate slower channel kinetics. Higher light sensitivity was found to correlate with slower channel kinetics, indicating a trade-off between light sensitivity and channel kinetics. Chop2 proteins that form the ChR2 proteins of the present invention may also comprise additional mutations or modifications that may improve channel kinetics, or increase the deactivation rate, of the ChR2. Particularly preferred ChR2 mutants balance the threshold of light sensitivity with channel kinetics.

Compositions and Kits

Compositions and kits of the invention comprise at least one nucleic acid molecule or polypeptide molecule that encodes a mutant Chop2 protein, and the resulting ChR2, of the invention. The at least one nucleic acid molecule or polypeptide molecule that encodes a mutant Chop2 protein of the invention may further include a pharmaceutically-acceptable carrier. Kits of the invention further include instructions for administering a composition of the invention to a subject.

Therapeutic Uses

Mutations were made on a codon optimized Chop2-GFP fusion protein to create single and double mutations at the L132 (Leucine 132) and T159 (threonine 159) sites. The functional properties of each mutant ChR2, or a combination thereof, were first examined in HEK cells. AAV2 virus vectors carrying mutant Chop2-GFP constructs driven by CAG promoter were made and injected intravitreally into the eyes of adult mice. Mutant Chop2-mediated light responses were examined by using multi-electrode array recordings from whole-mount retinas.

Single mutant ChR2, i.e., L132 and T159C, markedly lower the threshold light intensity that is required to evoke a ChR2-mediated photocurrent. Moreover, several double mutant ChR2 variants, including L132C/T159C, L132A/T159C, and L132C/T159S, were found to further increase the photocurrent above the results of any single mutant ChR2 at low light intensities. The double mutants exhibited a slower off-rate, which is likely to contribute to the increased photocurrent at the low light intensities. Spiking activity of retinal ganglion cells mediated by the L132C/T159C double mutant was observed at the light intensity of $10^{13}$ photon/cm$^2$/s and at the wavelength of 473 nm. This light level is about 1.5 to 2 log units lower than the light level that is required to elicit the spiking activity with wild-type ChR2. The spike firing of retinal ganglion cells expressing L132C/T159C could follow a light flicker frequency of up to 15 Hz. Ongoing studies are evaluating the long-term expression and safety of mutant ChR2s of the invention in retinal neurons.

Furthermore, expression of the mutant Chop2 proteins, and the resulting ChR2 proteins, of the present invention was not found to cause neurotoxicity of up to two months after viral injection in mice, demonstrating the safety of the present invention for therapeutic use.

Vectors for use in the present invention can include various viral vectors, such as plasmids and recombinant viruses, i.e., recombinant adeno-associated virus (rAAV), recombinant adenoviruses, recombinant retroviruses, recombinant lentiviruses, and other viruses known in the art.

In some embodiments, the expression of the Chop2 proteins of the present invention is driven by a constitutive promoter, i.e., CAG promoter, CMV promoter, LTR. In other embodiments, the promoter is an inducible or a cell-specific promoter. Cell type-specific promoters that enable Chop2 protein expression in specific subpopulations of cells, i.e., retinal neuron cells or degenerating cells, may be preferred. These cells may include, but are not limited to, a retinal ganglion cell, a photoreceptor cell, a bipolar cell, a rod bipolar cell, an ON-type cone bipolar cell, a retinal ganglion cell, a photosensitive retinal ganglion cell, a horizontal cell, an amacrine cell, or an AII amacrine cell. Cell type-specific promoters are well known in the art. Particularly preferred cell type-specific promoters include, but are not limited to mGluR6, NK-3, and Pcp2(L7).

In some embodiments, use of different opsin genes in addition to the mutant Chop2 proteins of the present invention and targeted gene expression may further increase light sensitivity or improve vision. Visual information is processed through the retina through two pathways: an ON pathway which signals the light ON, and an OFF pathway which signals the light OFF. The existence of the ON and OFF pathway is important for the enhancement of contrast sensitivity. The visual signal in the ON pathway is relay from ON-cone bipolar cells to ON ganglion cells. Both ON-cone bipolar cells and ON-ganglion cells are depolarized in response to light. On the other hand, the visual signal in the OFF pathway is carried from OFF-cone bipolar cells to OFF ganglion cells. Both OFF-cone bipolar cells and OFF-ganglion cells are hypopolarized in response to light. Rod bipolar cells, which are responsible for the ability to see in dim light (scotopic vision), are ON bipolar cells (depolarized in response to light). Rod bipolar cells relay the vision signal through AII amacrine cells (an ON type retinal cells) to ON an OFF cone bipolar cells.

Accordingly, a dual rhodopsin system can be used to recapitulate the ON and OFF pathways integral to visual processing and acuity. Briefly, a Chop2 protein of the present invention can be specifically targeted to ON type retinal neurons (i.e., ON type ganglion cells and/or ON type bipolar cells), while a hypopolarizing light sensor (i.e., halorhodopsin or other chloride pump known in the art) can be targeted to OFF type retinal neurons (i.e. OFF type ganglion cells and/or OFF type bipolar cells) to create ON and OFF pathways. The specific targeting to preferred cell subpopulations can be achieved through the use of different cell type-specific promoters. For example, Chop2 expression may be driven by the mGluR6 promoter for targeted expression in ON-type retinal neurons (i.e., ON type ganglion cells and/or ON type bipolar cells) while a hypopolarizing channel, such as halorhodopsin, expression is driven by the NK-3 promoter for targeted expression in OFF-type retinal neurons (i.e., OFF type ganglion cells and/or OFF type bipolar cells).

An alternative approach to restore ON and OFF pathways in the retina is achieved by, expressing a depolarizing light sensor, such as ChR2, to rod bipolar cells or AII amacrine. In this approach, the depolarization of rod bipolar cells or AII amacrine cells can lead to the ON and OFF responses at the levels of cone bipolar cells and the downstream retinal ganglion cells. Thus, the ON and OFF pathways that are inherent in the retina are maintained.

The present invention can be formulated to a pharmaceutical composition or medicament suitable for administration into a subject or patient. Suitable routes of administration include, for example, intravitreal, intraocular, or subretinal injection.

Such formulations comprise a pharmaceutically and/or physiologically acceptable vehicle, diluent, carrier or excipient, such as buffered saline or other buffers, e.g., HEPES, to maintain physiologic pH. For a discussion of such components and their formulation, see, generally, Gennaro, A E., *Remington: The Science and Practice of Pharmacy*, Lippincott Williams & Wilkins Publishers; 2003 or latest edition). See also, WO00/15822. If the preparation is to be stored for long periods, it may be frozen, for example, in the presence of glycerol.

The pharmaceutical composition described above is administered to a subject having a visual or blinding disease by any appropriate route, preferably by intravitreal or subretinal injection, depending on the retinal layer being targeted.

Disclosures from Bennett and colleagues (cited herein) concern targeting of retinal pigment epithelium—the most distal layer from the vitreal space. According to the present invention, the Chop2 construct or polypeptide is targeted to retinal cells, i.e., retinal ganglion cells or bipolar cells. Such cells are known to be reasonably well-accessible to intravitreal injection as disclosed herein. Intravitreal and/or subretinal injection can provide the necessary access to the bipolar cells, especially in circumstances in which the photoreceptor cell layer is absent due to degeneration—which is the case in certain forms of degeneration that the present invention is intended to overcome.

To test for the vector's ability to express the Chop2 mutants of the present invention, specifically in mammalian retinal neurons, by AAV-mediated delivery, a combination of a preferred promoter sequence linked to a reporter gene such as LacZ or GFP linked to a SV40 poly A sequence can be inserted into a plasmid and packaged into rAAV virus particles, concentrated, tested for contaminating adenovirus and titered for rAAV using an infectious center assay. The right eyes of a number of test subjects, preferably inbred mice, can be injected sub-retinally with about 1 µl of the rAAV preparation (e.g., greater than about $10^{10}$ infectious units ml). Two weeks later, the right (test) and left (control) eyes of half the animals may be removed, fixed and stained with an appropriate substrate or antibody or other substance to reveal the presence of the reporter gene. A majority of the test retinas in injected eyes will exhibited a focal stained region, e.g., blue for LacZ/Xgal, or green for GFP consistent with a subretinal bleb of the injected virus creating a localized retinal detachment. All control eyes may be negative for the reporter gene product. Reporter gene expression examined in mice sacrificed at later periods is detected for at least 10 weeks post-injection, which suggests persistent expression of the reporter transgene.

In one embodiment, the Chop2 constructs are packaged in adenoviral vectors for transgene delivery. An effective amount of rAAV virions carrying a nucleic acid sequence encoding the Chop2 DNA under the control of the promoter of choice, preferably a constitutive CMV promoter or a cell-specific promoter such as mGluR6, is preferably in the range of between about $10^{10}$ to about $10^{13}$ rAAV infectious units in a volume of between about 150 and about 800 µl per injection. The rAAV infectious units can be measured according to McLaughlin, S K et al., 1988, *J Virol* 62:1963. More preferably, the effective amount is between about $10^{10}$ and about $10^{12}$ rAAV infectious units and the injection volume is preferably between about 250 and about 500 µl. Other dosages and volumes, preferably within these ranges but possibly outside them, may be selected by the treating professional, taking into account the physical state of the subject (preferably a human), who is being treated, including, age, weight, general health, and the nature and severity of the particular ocular disorder.

It may also be desirable to administer additional doses ("boosters") of the present nucleic acid(s) or rAAV compositions. For example, depending upon the duration of the transgene expression within the ocular target cell, a second treatment may be administered after 6 months or yearly, and may be similarly repeated. Neutralizing antibodies to AAV are not expected to be generated in view of the routes and doses used, thereby permitting repeat treatment rounds.

The need for such additional doses can be monitored by the treating professional using, for example, well-known electrophysiological and other retinal and visual function tests and visual behavior tests. The treating professional will be able to select the appropriate tests applying routine skill in the art. It may be desirable to inject larger volumes of the composition in either single or multiple doses to further improve the relevant outcome parameters.

Ocular Disorders

The ocular disorders for which the present Chop2 proteins, and the resulting ChR2 proteins, are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders. These disorders include genetically pre-disposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. (Trabulsi, E I, ed., *Genetic Diseases of the Eye*, Oxford University Press, NY, 1998).

In particular, the Chop2 and ChR2 proteins of the present invention useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by the Chop2 and ChR2 proteins of the present invention. Thus, the particular ocular disorder treated by the present invention may include the above-mentioned disorders and a number of diseases which have yet to be so characterized.

Optogenetics

The emerging field of optogenetics involves the combination of genetic and optical methods to control specific events in targeted cells of a living tissue. Optogenetics may be used within freely moving mammals and other animals. Moreover, the temporal precision (millisecond-timescale) of optogenetic methods are sufficient to function within intact biological systems.

The instant invention provides Chop2-gene therapy to retinal tissues of the eye, by introducing into retinal cells a nucleic acid or polypeptide encoding for at least one mutant form of Chop2. Mutant Chop2/ChR2 proteins of the invention are specifically adapted to be light-activated at lower thresholds of light intensities than their wild type counterparts. Accordingly, the mutant Chop2/ChR2 proteins of the invention can be used to activate cells of the retina and visual system using less damaging sources of illumination. The mutant Chop2/ChR2 proteins also conduct larger photocurrents upon activation, resulting in a more robust or efficacious response from the mutant Chop2/ChR2-expressing cells.

For example, mutant Chop2 proteins of the invention are administered to a subject through local, intravitreous or subretinal, injection of a nucleic acid molecule encoding a mutant Chop2, a mutant Chop2 polypeptide molecule, or a cell expressing a mutant Chop2/ChR2. Retinal cells of the subject express the mutant Chop2 proteins within the plasma membrane. When the transfected or transformed retinal cells encounter light radiation, the transfected or transformed retinal cells transduce an improved or restored signal.

These methods may be used in subjects of normal and/or impaired vision. Chop2/ChR2 mutants of the invention may preserve, improve, or restore vision. Moreover, Chop2/ChR2 mutants of the invention are used to preserve, improve, or restore the transduction of non-visual information from photosensitive retinal ganglion cells to the brain.

The term "vision" as used herein is defined as the ability of an organism to usefully detect light as a stimulus for differentiation or action. Vision is intended to encompass the following:
1. Light detection or perception—the ability to discern whether or not light is present;
2. Light projection—the ability to discern the direction from which a light stimulus is coming;
3. Resolution—the ability to detect differing brightness levels (i.e., contrast) in a grating or letter target; and
4. Recognition—the ability to recognize the shape of a visual target by reference to the differing contrast levels within the target.

Thus, "vision" includes the ability to simply detect the presence of light. The polypeptides and polynucleotides encoding mutant Chop2 of the present invention can be used to improve or restore vision, wherein the improvement or restoration in vision includes, for example, increases in light detection or perception, increase in light sensitivity or photosensitivity in response to a light stimulus, increase in the ability to discern the direction from which a light stimulus is coming, increase in the ability to detect differing brightness levels, increase in the ability to recognize the shape of a visual target, and increases in visual evoked potential or transmission from the retina to the cortex. As such, improvement or restoration of vision may or may not include full restoration of sight, i.e., wherein the vision of the patient treated with the present invention is restored to the degree to the vision of a non-affected individual. The visual recovery described in the animal studies described below may, in human terms, place the person on the low end of vision function by increasing one aspect of vision (i.e., light sensitivity, or visual evoked potential) without restoring full sight. Nevertheless, placement at such a level would be a significant benefit because these individuals could be trained in mobility and potentially in low order resolution tasks which would provide them with a greatly improved level of visual independence compared to total blindness. Even basic light perception can be used by visually impaired individuals, whose vision is improved using the present compositions and methods, to accomplish specific daily tasks and improve general mobility, capability, and quality of life.

The degree of restoration of vision can be determined through the measurement of vision before, and preferably after, administering a vector comprising, for example, DNA encoding Chop2. Vision can be measured using any of a number of methods well-known in the art or methods not yet established. Vision, as improved or restored by the present invention, can be measured by any of the following visual responses:
1. a light detection response by the subject after exposure to a light stimulus—in which evidence is sought for a reliable response of an indication or movement in the general direction of the light by the subject individual when the light it is turned on;
2. a light projection response by the subject after exposure to a light stimulus in which evidence is sought for a reliable response of indication or movement in the specific direction of the light by the individual when the light is turned on;
3. light resolution by the subject of a light vs. dark patterned visual stimulus, which measures the subject's capability of resolving light vs dark patterned visual stimuli as evidenced by:
   a. the presence of demonstrable reliable optokinetically produced nystagmoid eye movements and/or related head or body movements that demonstrate tracking of the target (see above) and/or
   b. the presence of a reliable ability to discriminate a pattern visual stimulus and to indicate such discrimination by verbal or non-verbal means, including, for example pointing, or pressing a bar or a button; or
4. electrical recording of a visual cortex response to a light flash stimulus or a pattern visual stimulus, which is an endpoint of electrical transmission from a restored retina to the visual cortex, also referred to as the visual evoked potential (VEP). Measurement may be by electrical recording on the scalp surface at the region of the visual cortex, on the cortical surface, and/or recording within cells of the visual cortex.

Thus, improvement or restoration of vision, according to the present invention, can include, but is not limited to: increases in amplitude or kinetics of photocurrents or electrical response in response to light stimulus in the retinal cells, increases in light sensitivity (i.e., lowering the threshold light intensity required for initiating a photocurrent or electrical response in response to light stimulus, thereby requiring less or lower light to evoke a photocurrent) of the retinal cells, increases in number or amplitude of light-evoked spiking or spike firings, increases in light responses to the visual cortex, which includes increasing in visual evoked potential transmitted from the retina or retinal cells to the visual cortex or the brain.

Both in vitro and in vivo studies to assess the various parameters of the present invention may be used, including recognized animal models of blinding human ocular disorders. Large animal models of human retinopathy, e.g., childhood blindness, are useful. The examples provided herein allow one of skill in the art to readily anticipate that this method may be similarly used in treating a range of retinal diseases.

While earlier studies by others have demonstrated that retinal degeneration can be retarded by gene therapy techniques, the present invention demonstrates a definite physiological recovery of function, which is expected to generate or improve various parameters of vision, including behavioral parameters.

Behavioral measures can be obtained using known animal models and tests, for example performance in a water maze, wherein a subject in whom vision has been preserved or restored to varying extents will swim toward light (Hayes, J M et al., 1993, *Behav Genet.* 23:395-403).

In models in which blindness is induced during adult life or congenital blindness develops slowly enough that the individual experiences vision before losing it, training of the subject in various tests may be done. In this way, when these tests are re-administered after visual loss to test the efficacy of the present compositions and methods for their vision-restorative effects, animals do not have to learn the tasks de novo while in a blind state. Other behavioral tests do not require learning and rely on the instinctiveness of certain behaviors. An example is the optokinetic nystagmus test (Balkema G W et al., 1984, *Invest Ophthalmol Vis Sci.* 25:795-800; Mitchiner J C et al., 1976, *Vision Res.* 16:1169-71).

The present invention may also be used in combination with other forms of vision therapy known in the art to improve or restore vision. For example, the use of visual prostheses, which include retinal implants, cortical implants, lateral geniculate nucleus implants, or optic nerve implants. Thus, in addition to genetic modification of surviving retinal neurons using the present methods, the subject being treated may be provided with a visual prosthesis before, at the same time as, or after the molecular method is employed. The effectiveness of visual prosthetics can be improved with training of the individual, thus enhancing the potential impact of the Chop2 transformation of patient cells as contemplated herein. Training methods, such as habituation training characterized by training the subject to recognize (i) varying levels of light and/or pattern stimulation, and/or (ii) environmental stimulation from a common light source or object as would be understood by one skilled in the art; and orientation and mobility training characterized by training the subject to detect visually local objects and move among said objects more effectively than without the training. In fact, any visual stimulation techniques that are typically used in the field of low vision rehabilitation are applicable here.

EXAMPLES

Example 1: Generation of Labeled Mutant Chop2 Constructs

Mutations were made on a codon optimized Chop2-GFP fusion protein to create single and double mutations at the L132 (Leucine 132) and T159 (Threonine 159) sites. Several mutants were generated, for example, single mutants such as L132A, L132C, T159A, T159C, and T 159S, and double mutants such as L132C/T159C, L132C/T159S, L132A/T159C, and L132C/T159A. Chop2-GFP transgenes were cloned into a rAAV vector under the control of a CAG promoter using methods known in the art.

Example 2: In Vitro Analysis of Mutant Chop2 Constructs

The functional properties of each mutant Chop2, or a combination thereof, were first examined in HEK cells. Chop2 constructs were delivered to HEK cells by adenoviral infection, for example. Upon expression of the WT or mutant Chop2, functional WT and mutant ChR2 channels were formed. Measurements of the light sensitivity and other properties of the ChR2 channels were assessed as described herein. The light stimuli (photons/cm$^2$.s at 460 nm) were generated by a xenon arc lamp and attenuated by neutral density filters: ND4.0 ($2.8 \times 10^{14}$), ND3.0 ($1.4 \times 10^{15}$), ND2.5 ($4.8 \times 10^{15}$); ND2.0 ($1.6 \times 10^{16}$), ND1.0 ($1.3 \times 10^{17}$), ND0 ($1.2 \times 10^{18}$). Light evoked currents were measured from wild-type ChR2, T159C, L132C, L132C/T159C, and L132C/T159S. Patch clamp recordings were performed using methods known in the art.

Representative recordings from this experiment comparing light sensitivity between the Chop2 constructs demonstrated that mutations at L132 alone or in combination with mutation at T159 show increased photocurrent in comparison to WT (FIGS. 1A and 1B). FIG. 1B shows the same current traces at a different scale to illustrate the difference in amplitude of the photocurrents between WT ChR2 and ChR2 mutants more clearly. FIG. 1B specifically compares the current traces resulting from light stimulation using the neutral density filter (ND 2.5), equivalent to $4.8 \times 10^{15}$ photos/cm$^2$/s; the traces are designated by the arrows. The amplitude of the photocurrent of the L132C mutant is larger than that of WT; the amplitude of the photocurrent of double mutant L132C/T159C is larger than that of L132C; and the amplitude of the photocurrent of the L132C/T159S mutant larger than L132/T159C. The current traces of the ChR2 mutants, particularly double mutants L132C/T159C and L132C/T159S, also show slower deactivation kinetics when compared to WT and L132C.

Figure 2:
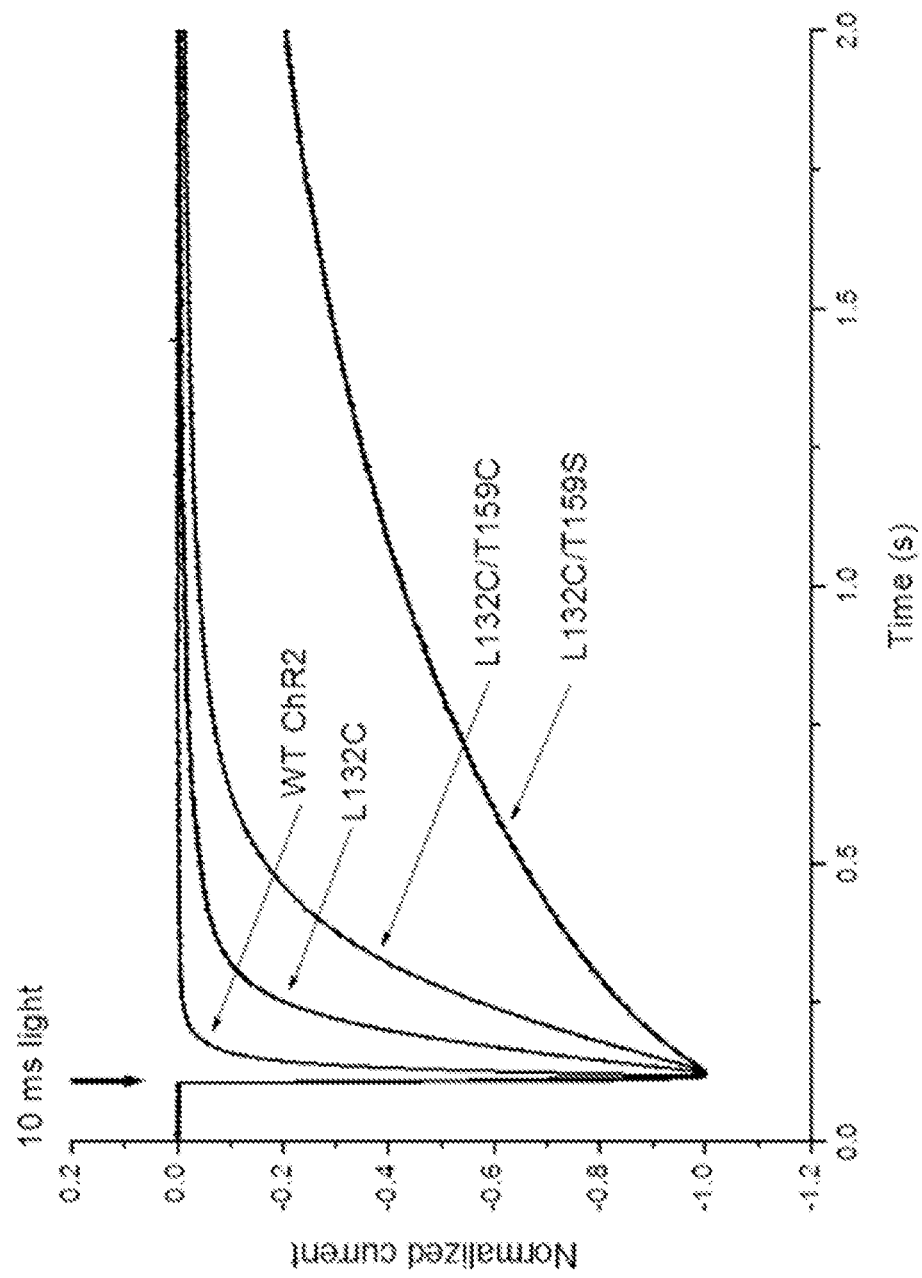
FIG. 2 shows representative recordings of the light-evoked currents from wild-type (WT) ChR2, T159C, L132C, L132C/T159C, and L132C/T159S mutants to a 10 ms light pulse ($1.2 \times 10^{18}$ photons/cm$^2$/s at 460 nm) in HEK cells for comparison of their deactivation time course (decay time course after light off).

FIG. 2 shows the representative recordings of light-evoked currents from WT ChR2, L132C, L132C/T159C, and L132C/T159S after stimulation by a 10 ms light pulse ($1.2 \times 10^{18}$ photons/cm$^2$/s at 460 nm wavelength) to compare the deactivation time course, or decay time course after the light is off. Mutant ChR2 show longer deactivation time courses, with the double mutant L132C/T159S having the longest. Higher light sensitivity, as demonstrated by L132C/T159C and L132C/T159S, may be correlated with slower channel kinetics.

Example 3: In Vivo Ocular Administration and Analysis of Mutant Chop2 Constructs AAV2 virus vectors carrying mutant Chop2-GFP constructs driven by CAG promoter were made and injected intravitreally into the eyes of C57BL/6J adult mice. Adult mice were anesthetized by IP injection of ketamine (100 mg/kg) and xylazine (10 mg/kg). Under a dissecting microscope, an incision was made by scissors through the eyelid to expose the sclera. A small perforation was made in the sclera region posterior to the lens with a needle and viral vector suspension of 0.8-1.5 µl at the concentration of approximately $10^{11}$ genomic particles/ml was injected into intravitreal space through the hole with a Hamilton syringe with a 32-gauge blunt-ended needle. For each animal, usually only one eye was injected with viral vectors carrying a Chop2 construct, and the other eye was uninjected or injected with control viral vectors carrying GFP alone. Upon expression of the WT or mutant Chop2 of the present invention, functional WT or mutant ChR2 channels were formed utilizing endogenous retinal, and the properties of these ChR2 proteins were assessed as described herein.

ChR2-mediated light responses were examined by using multi-electrode array recordings from whole-mount retinas. Light stimuli (photons/cm$^2$/s) was generated by a 473 nm blue laser and attenuated by neutral density filters: ND0 ($6.3 \times 10^{16}$), ND1.0 ($7.4 \times 10^{15}$), ND1.5 ($2.7 \times 10^{15}$), ND2.0 ($7.3 \times 10^{14}$), ND2.5 ($3.2 \times 10^{14}$), ND3.0 ($8.5 \times 10^{13}$), ND3.5 ($3.8 \times 10^{13}$), and ND4.0 ($9.5 \times 10^{12}$).

The multielectrode array recordings were based on the procedures reported by Tian and Copenhagen (2003). Briefly, the retina was dissected and placed photoreceptor side down on a nitrocellulose filter paper strip (Millipore Corp., Bedford, Mass.). The mounted retina was placed in the MEA-60 multielectrode array recording chamber of 30 µm diameter electrodes spaced 200 µm apart (Multi Channel System MCS GmbH, Reutlingen, Germany), with the ganglion cell layer facing the recording electrodes. The retina was continuously perfused in oxygenated extracellular solution at 34° C. during all experiments. The extracellular solution contained (in mM): NaCl, 124; KCl, 2.5; CaCl$_2$, 2; MgCl$_2$, 2; NaH$_2$PO$_4$, 1.25; NaHCO$_3$, 26; and glucose, 22 (pH 7.35 with 95% O$_2$ and 5% CO$_2$). Recordings were usually started 60 min after the retina was positioned in the recording chamber. The interval between onsets of each light stimulus was 10-15 s. The signals were filtered between 200 Hz (low cut off) and 20 kHz (high cut off). The responses from individual neurons were analyzed using Offline Sorter software (Plexon, Inc., Dallas, Tex.).

Figure 3:
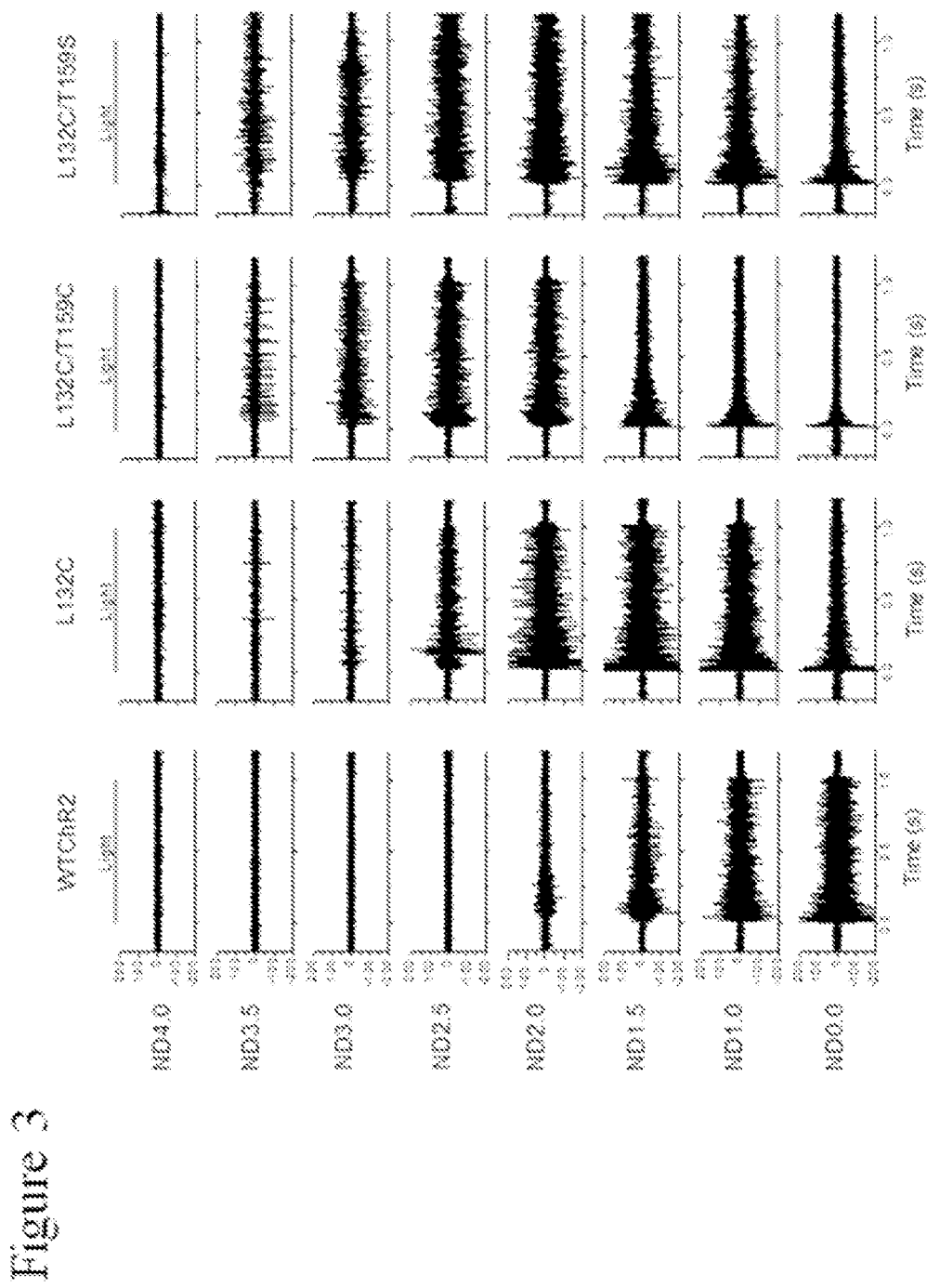
FIG. 3 shows representative multichannel array recordings of WT ChR2, L132C, L132C/T159C, and L132C/T159S mediated spiking activities from retinal ganglion cells in retinal whole-mounts for comparison of their light sensitivity. Light stimuli (photons/cm$^2$/s) was generated by a 473 nm blue laser and attenuated by neutral density filters: ND0 ($6.3 \times 10^{16}$), ND1.0 ($7.4 \times 10^{15}$), ND1.5 ($2.7 \times 10^{15}$), ND2.0 ($7.3 \times 10^{14}$), ND2.5 ($3.2 \times 10^{14}$), ND3.0 ($8.5 \times 10^{13}$), ND3.5 ($3.8 \times 10^{13}$), and ND4.0 ($9.5 \times 10^{12}$).
Figure 4A:
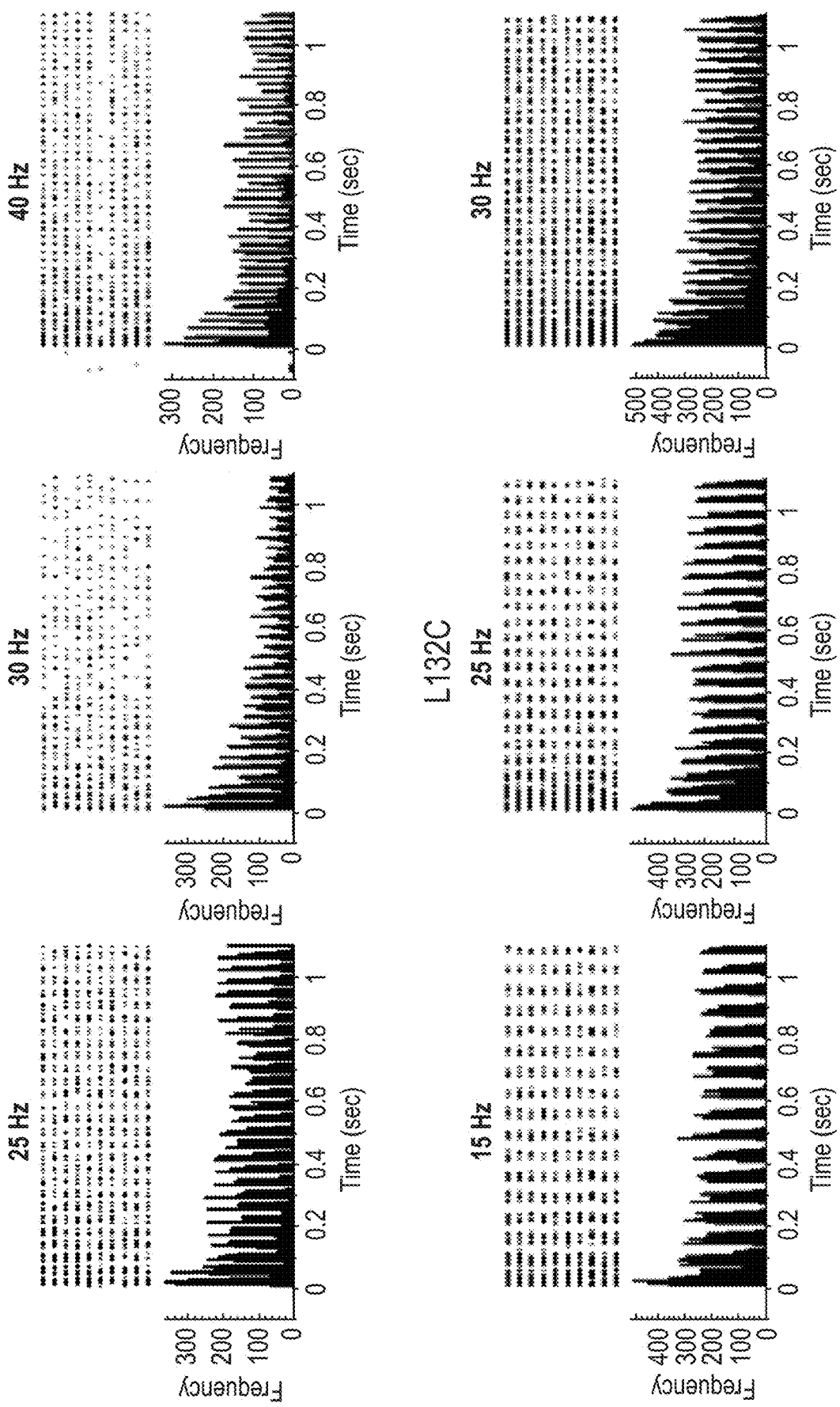
FIG. 4 shows representative multichannel array recordings of WT ChR2, L132C, L132C/T159C, and L132C/T159S mediated spiking activities from retinal ganglion cells in retinal whole-mounts for comparison of their temporal dynamics. In each panel, the raster plots of 10 consecutive light-elicited spikes originated from a single neuron (top) and the averaged spike rate histograms (bottom) are shown. Light pulses at different frequency was generated by a 473 nm blue laser with intensities about one log unit above the threshold intensity of each mutant. Recordings of WT ChR2 and L132C are shown in (A), and recordings of L132C/T159C and L132C/T159S are shown in (B).
Figure 4B:
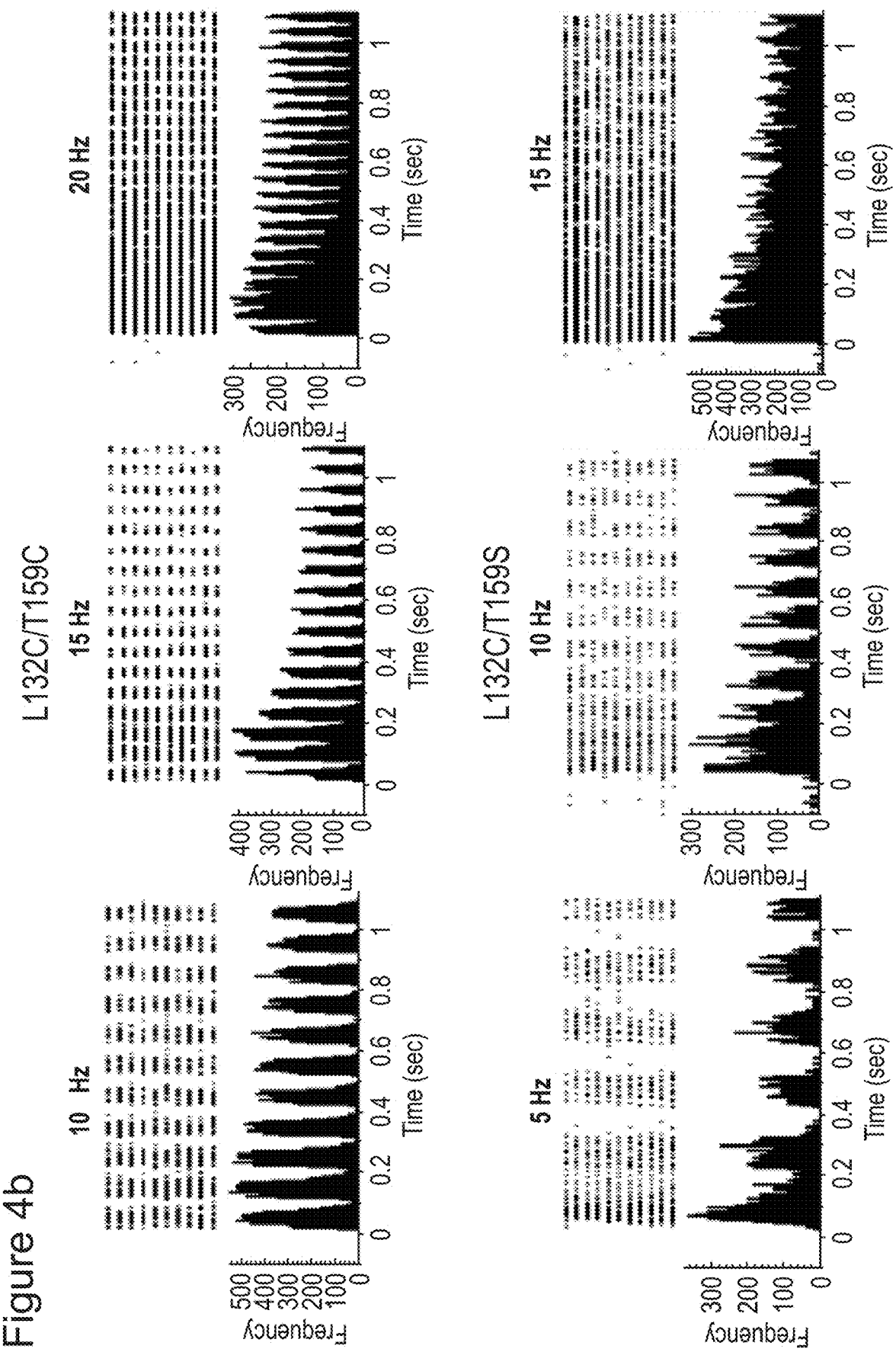

Single mutant Chop2/ChR2 mutants, i.e., L132 and T159C, markedly lower the threshold light intensity that is required to evoke a ChR2-mediated photocurrent. Moreover, several double mutants, including L132C/T159C, L132A/T159C, and L132C/T159S, were found to further increase the photocurrent at low light intensities. Different neutral density filters were used to attenuate the light stimuli to differentiate the light-evoked responses of the Chop2 constructs in low light. Spiking activity of retinal ganglion cells mediated by the mutants of the present invention was observed at the light intensities about 1.5 to 2 log units lower than the light level that is required to elicit the spiking activity with wild-type ChR2 (FIG. 3). Specifically, WT ChR2 exhibited did not exhibit any spiking activity in response to light stimuli with neutral density filter 2.5 ($3.2 \times 10^{14}$ photons/cm$^2$/s) while ChR2 mutants (L132C, L132C/T159C, and L132C/T159S) demonstrate spiking activity. In fact, the ChR2 mutants still exhibited spiking activity in response to light with neutral density filters 3.0 and 3.5. Therefore, ChR2 mutants of the present invention possess higher light sensitivity and, thus, a markedly lower threshold light intensity that is required to elicit a ChR2-mediated photocurrent. Moreover, ChR2 double mutants possess a higher light sensitivity than single mutants, i.e. L132C. In addition, the spike firing of retinal ganglion cells expressing L132C/T159C and L132/T159S could follow a light flicker frequency of up to 15 Hz and 5 Hz, respectively (FIG. 4).

The L132C/T159A mutant shows high light sensitivity, probably the most light sensitive among these mutants, but it also shows extremely slow off-rate (the channel continue open for many sends after light off). Interestingly, it can be turned off more quickly using a light with long-wavelengths, such as yellow light. The L132C/T159A mutant (encoded by SEQ ID NOs: 24 and 25) demonstrates significant potential.

Given the trade-off between light sensitivity and channel kinetics, Chop2/ChR2 mutants that demonstrate a balance between light sensitivity and channel kinetics, such as L132C/T159C or L132C/T159S, may be suitable for the application of vision restoration.

Example 4: Analysis of Mutant Chop2 Constructs in Mouse Models of Disease

Mouse models of degenerative ocular diseases are known in the art. For example, homozygous rd1 (rd1/rd1) mice are a commonly used photoreceptor degeneration model. Rd1 mice carry a null mutation in a cyclic GMP phosphodiesterase, PDE6, similar to some forms of retinitis pigmentosa in humans. Other well-established mouse models of ocular disease that may be of particular interest to demonstrate ChR2 mutant safety and efficacy include rds (also known as Prph$^{Rd2}$), rd3, rd4, rd5, rd6, rd7, rd8, rd9, Pde6b$^{rd10}$, or cpfl1 mice.

The Chop2-GFP constructs of the present invention can be injected intravitreally into the eyes of newborn (P1) or adult mice at 2-12 months of age. GFP signal can be observed in the Chop2-GFP-injected retinas, to determine the levels of ChR2 expression or expression in particular populations of cells, such as the retinal ganglion cells.

Mutant Chop2-GFP expression can be monitored for a predetermined amount of time, i.e. 3-6 months, or 1 year after viral injection. Patch-clamp and multichannel array recordings can be performed using the methods known in the art and described herein to measure the light-evoked responses of mutant Chop2-GFP-expressing cells in vivo.

Additional techniques and tests are well-established in the art to test for the restoration of light sensitivity or vision. Visual evoked potentials from the Chop2-GFP expressing cells or visual cortex can be examined, as described in PCT publication WO 2007/131180. Other tests include behavioral assessments of the visual acuity in the mice, i.e., virtual optomotor test and visual water maze.

Example 5: Analysis of Long-Term Expression and Safety of Administration of Mutant Chop2 Constructs to Retinal Neurons Neurotoxicity was assessed in C57BL/6J adult mice injected with Chop2 constructs of the present invention. The expression safety of Chop2 mutants in the retina was assessed by immunostaining and cell counting after exposure to strong blue light for two weeks. None of the mice were found to exhibit symptoms of neurotoxicity for up to two months after injection.

Additional ongoing studies are evaluating the long-term expression and safety of Chop2/ChR2 mutants of the invention in retinal neurons.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated polypeptide molecule comprising SEQ ID NO: 26 in which the amino acid at position 132 is cysteine (C), wherein the amino acid at position 159 is serine (S), and wherein, in a retinal cell, the polypeptide confers light sensitivity at a light flicker frequency between 5 Hz-15 Hz and a slower off rate of the channel when compared to a Wild Type (WT) polypeptide comprising SEQ ID NO: 26.

2. A method comprising administering to a subject a composition comprising the polypeptide of claim 1, wherein the method results in increased light sensitivity, lowered threshold light intensity required to elicit a photocurrent and/or increased visual evoked potential in the visual cortex, each of which is relative to a subject that has normal or impaired vision.

3. The method of claim 2, wherein the subject has normal vision.

4. The method of claim 2, wherein the subject has impaired vision.

5. The method of claim 2, wherein the subject is suffering from an ocular disease.

6. The method of claim 5, wherein the ocular disease is macular degeneration or retinitis pigmentosa.

7. The method of claim 2, wherein the composition is administered by intravitreal or subretinal injection.

* * * * *